(12) United States Patent
Van Den Ackerveken et al.

(10) Patent No.: US 8,796,511 B2
(45) Date of Patent: Aug. 5, 2014

(54) DISEASE RESISTANT PLANTS

(71) Applicant: Enza Zaden Beheer B.V., Enkhuizen (NL)

(72) Inventors: Augustinus Franciscus Johannes Maria Van Den Ackerveken, Houten (NL); Mireille Maria Augusta Van Damme, Amsterdam (NL)

(73) Assignee: Enza Zaden Beheer B.V., Enkhuizen (NL)

( * ) Notice: Subject to any disclaimer, the term of this patent is extended or adjusted under 35 U.S.C. 154(b) by 0 days.

(21) Appl. No.: 13/969,951

(22) Filed: Aug. 19, 2013

(65) Prior Publication Data

US 2013/0333069 A1    Dec. 12, 2013

Related U.S. Application Data

(62) Division of application No. 13/713,332, filed on Dec. 13, 2012, now Pat. No. 8,575,432, which is a division of application No. 13/545,853, filed on Jul. 10, 2012, now Pat. No. 8,354,570, which is a division of application No. 12/092,253, filed as application No. PCT/EP2006/010535 on Nov. 1, 2006, now Pat. No. 8,237,019.

(51) Int. Cl.
| | |
|---|---|
| *A01H 5/00* | (2006.01) |
| *A01H 1/00* | (2006.01) |
| *C12N 15/09* | (2006.01) |
| *C12N 15/82* | (2006.01) |

(52) U.S. Cl.
USPC ........... 800/301; 800/279; 800/276; 800/298; 800/320.1; 800/320.2; 800/317

(58) Field of Classification Search
USPC .......... 800/278, 279, 276, 301, 302; 435/419, 435/418, 468
See application file for complete search history.

(56) References Cited

FOREIGN PATENT DOCUMENTS

| | | |
|---|---|---|
| WO | 0070016 A2 | 11/2000 |
| WO | 02088301 A2 | 11/2002 |

OTHER PUBLICATIONS

Van der Meer et al. Euphytica (1990), 47:29-31.*
Aubert et al. Transport, compartmentation, and metabolism of homoserine in higher plant cells. Plant Physiol. vol. 116 (1998) pp. 547-557.
Lee et al. Identification of the gene encoding homoserine kinase from Arabidopsis thaliana and characterization of the recombinant enzyme derived from the gene. Arch. Biochem Biophys vol. 372, No. 1 (1999) pp. 135-142.
Lee et al. Methionine and threonine synthesis are limited by homoserine availability and not the activity of homoserine kinase in Arabidopsis thaliana. The Plant Journal vol. 41 (2005) pp. 685-696.
Van Damme et al. Identification of Arabidopsis loci required for susceptibility to the downy mildew pathogen *Hyaloperonospora parasitica*. Mol. Plant-Microbe Interact. vol. 18, No. 6 (2005) pp. 583-592.

* cited by examiner

*Primary Examiner* — Medina A Ibrahim
(74) *Attorney, Agent, or Firm* — The Webb Law Firm

(57) ABSTRACT

The present invention relates to a plant, which is resistant to a pathogen of viral, bacterial, fungal or oomycete origin, wherein the plant has an increased homoserine level as compared to a plant that is not resistant to the said pathogen, in particular organisms of the phylum Oomycota. The invention further relates to a method for obtaining a plant, which is resistant to a pathogen of viral, bacterial, fungal or oomycete origin, comprising increasing the endogenous homoserine level in the plant.

6 Claims, 14 Drawing Sheets

Fig. 1

```
Arabidopsis_thaliana    ---MASLCFQSPS---KPISYFQPKS-----NPSPPLFAKVSVFRCRASVQTLVA-----   44
Citrus_sinensis         ----MAICFSSAV---KPANHFTVFF-----NPAP----KKPIFKCSCSLPTVTT-----   39
Populus_trichocarpa_1   ---MAICCFPSPL---KPMTPATPLT-----NLKPK---RPDILRCNFSLPTITT-----   41
Populus_trichocarpa_2   ---MAIC-FLSPL---KPITPTTSLTT----NLNPK---KPNILRCNFSLPIITT-----   41
Solanum_tuberosum_2     ----MAVLCQSP---LNLKLITSSSSS-----SRNRTANP----SFRLNLSAHSR-----   39
Vitis_vinifera          ----MAICFHSP---SKPTCISPSSNH-----YRPNLHAR----SFRCNFSKTLT-----   39
Lactuca_sativa          ----MAIRHYQPPFASTSSSISSTDLF-----KPPKLYLSS---SVRCNISVASK-----   43
Solanum_tuberosum_1     ----MAITYQSP---MKLNFITSNGFS-----NPPSLYPINTHFSFGFNLSSVSSKTQT-   47
Solanum_lycopersicum    ----MAITFQSP---MKLSFITSNGFS-----NPPSLYPINTHFSFGFNLSSVSSKTQT-   47
Nicotiana_benthamiana   ---MAAICYQSP---VKLNFTTSNAFSNPIPNNPPPLYPIKTRFSSGFNLSAVPSKTQTT   54
Ipomoea_nil             -----------------ASISSTRHP-----NPPLCLPALNISRCGPLFSAVTSSTLA-   36
Glycine_max             ----MATSTCFLC--PSTASLKGRARF------RIR---IRCSSS----VSVNIR-----   36
Phaseolus_vulgaris      ----MATAMSFLC--PSPATFKGTEMP------IAR---FRCCSSNTNSVSLNTR-----   40
Cucumis_sativus         ----MAMLSYQPP--LKSLTIPPVSLS------NPKPVLFRCSLSLPSRTAVTS------   42
Spinacia_oleracea       ----MAICAQSP---FKPVNLSPHSPS----PTHKSPFICKLSLSSHSTHSPLTT-----   44
Pinus_taeda             MESVFAQTKNHCFYLEPDLGLINSCFGLSRFRTKFSRGHLPHVFNVRCNAQQVSLKP---   57
Zea_mays                ----MAPAATSTAS-APSSFHSTGRHR----ARVGARPSLVSLRVRAANPNVT------   46
Oryza_sativa            ---MAAAAAAAAAP--SPAPCFPSTRH-----TLPGLVSVRVSRRVKVA--VAI------   44

K (dmr1-2)
                                        ▼
Arabidopsis_thaliana    ----VEPEPVFVSVKTFAPATVANLGPGFDFLGCAVDG----LGDHVTLRVDPSVRAGEV   96
Citrus_sinensis         ----TEPEPVFTSVKTFAPATVANLGPCFDFLGCAVDG----LGDYVSLKVDPSVHPGEV   91
Populus_trichocarpa_1   ----TEPEPVFTSVRSFAPATVANLGPGFDFLGCAVDG----LGDFVSLRVDPSVHPGEL   93
Populus_trichocarpa_2   ----TEPEPVFTSVRSFAPATVANLGPGFDFLGCAVDG----LGDFVSLRVDPSVHPGEL   93
Solanum_tuberosum_2     ----SEPSPVFTSVKSFAPATVANLGPGFDFLGCAVDG----IGDFVTLRLDPNVHPGEV   91
Vitis_vinifera          ----ADPQPVFTSVKSFAPATVANLGPGFDFLGAAVDG----IGDFVSLRVDPDVRPGEI   91
Lactuca_sativa          --LEPEPHPVFTSVKSFAPATVANLGPGFDFLGCAIDG----IGDYVTLTVDPQVQPGRL   97
Solanum_tuberosum_1     HITIPEPEPVFTSVKSFAPATVANLGPGFDFLGCAVDG----IGDFVTLRVDPNVKAGEV  103
Solanum_lycopersicum    HITIPEPEPVFTSVKSFAPATVANLGPGFDFLGCAVDG----VGDFVTLRVDPNVKAGEV  103
Nicotiana_benthamiana   HITIPEPEPVFASVKSFAPATVANLGPGFDFLGCAVDG----IGDFITLRVDSKVKPGEV  110
Ipomoea_nil             ---VSDPEPVYASVKSFAPATVANLGPGFDFLGCAVDG----IGDFVTVRVDPDVPPGQV   89
Glycine_max             ----REPEPVTTLVKAFAPATVANLGPGFDFLGCAVDG----LGDIVSVKVDPQVHPGEl   88
Phaseolus_vulgaris      ----TEPQPVTTFVKAFAPATVANLGPGFDFLGCAVDG----IGDIVSVRVDPEVRPGEl   92
Cucumis_sativus         ----VEPQPVFSSVKAFAPATVANLGPGFDFLGCAVDG----IGDYVSLSVDSNVHPGEV   94
Spinacia_oleracea       -----EPTPLLTSVTTFAPATVANLGPGFDFLGCAVDG----LGDFVSLSVDPSVHPGQL   95
Pinus_taeda             -VIQFEATPILQSVKAFAPATIANLGPGFDFLGCAVEG----LGDHVTVEVNEDVEPGKI  112
Zea_mays                ----ADPAPAFQSVTTFAPATVANLGPGFDFLGCAVADASLSLGDTVTATLDPSLPPATV  100
Oryza_sativa            ----ADPAPAFNSVTAFAPATVANLGPGFDFLGCAVADASLSLGDTVTATLDPSLPPGTV   98
                            :    *   ** :*****:***** *****.*:  .    :**  ::   ::  .: ..:

Arabidopsis_thaliana    SISEITGTTT-----KLSTNPLRNCAGIAAIATMKMLGIRSVGLSLDLHKGLPLGSGLGS  151
Citrus_sinensis         SISEVIGPS------KLSKNPLWNCAGIAAISAMKMLGVRSVGLSLSLEKGLPLGSGLGS  145
Populus_trichocarpa_1   SISDISGPK------KLSKNPLYNCAGIAAIATMKMLNIRSVGLSLSLEKGLPLGSGLGS  147
Populus_trichocarpa_2   SISDISGTK------NLSKNPLNNCAG1AAIATMKMLNIRSVGLSLSLEKGLPLGSGLGS  147
Solanum_tuberosum_2     SISDISGAG-----KKLRRNPRWNCAGIAAISVMKMLNIRSVGLTLSLHKGLPLGSCLGS  146
Vitis_vinifera          SIVDIDGVGNS--AKKLSKNPLWNCAGIAAISVMKMLGVRSVGLSLSLEKGLPLGSGLGS  149
Lactuca_sativa          SIAEINGVDKS--SKRLSRNPLWNCAGIAAISVMKMLKIRSVGLSLSINTCLPLRGGLGS  155
Solanum_tuberosum_1     SISDISGAG-----NRLSKDPLSNCAGIAAISVMKMLN1QSVGLSISLEKGLPLGSGLGS  158
Solanum_lycopersicum    SISDISGAG-----NRLSKDPLSNCAGIAAISVMKMLNIQSVGLSISLEKGLPLGSGLGS  158
Nicotiana_benthamiana   SISDISGAG-----GKLSKDPLSNCAGIAAISVMKMLNIQSVGLSISLEKGLPLGSGLGS  165
Ipomoea_nil             SISEISGAG-----NKLSKNPLWNCAGIAAIVMKMLRIQSVGLSLSLEKGLPLGSGLGS   144
Glycine_max             CISDISGHAP----NKLSKNPLWNCAGIAAIEVMKMLSIRSVGLSLSLEKGLPLGSGLGS  144
Phaseolus_vulgaris      RISDITGHAP----NKLSTNPLWNCAGIAAIEVMKMLAIRSVGLSLSLQKGLPLGSGLGS  148
Cucumis_sativus         AISDITGNNT----NKLSKNPLYNCAGIAAIEVMKMLGIRSVGLSLSLEKGLPLGSGLGS  150
Spinacia_oleracea       SISSISGDAS----SKLSKDPLLNCAGISALAAMKLLNIRSVGLSLSLOKGLPLGSGLGS  151
Pinus_taeda             VISFIDGDN-----NRLSLNPMKNCAGIAAKATMELLGVRSVGLSLGLHKGLPLGSGLGS  167
Zea_mays                SIASVTSPSRPNLAERLSRDPLRNCAGVAAIAALRALGVRSHAVSIHLTKGLPLGSGLGS  160
Oryza_sativa            AIASVTSPSRPTLADRLSRDPLRNCAGVAAIAALRALDVKSHAVSIHLTKGLPLGSGLGS  158
                        *    :  .    .*  :* ****::*    .:. * ::*  .:::  :    ***  .  ***

D (dmr1-5)                      R (dmr1-4)
                                    ▼                              ▼
Arabidopsis_thaliana    SAASAAAAAVAVNEIFGRKLGSDQLVLAGLESEAKVSGYHADNIAPAIMGGFVLIRNYEP  211
Citrus_sinensis         SAASAAAAAVAVNEMFGNKLLPDELVLAGLESEAKVSGYHADNIAPAIMGGFVLIRSYEP  205
Populus_trichocarpa_1   SAASAAAAAVAVNELFGRKLEVKDLVLAGLESEAKVSGYHADNIAPAIMGGFVLIRSYDP  207
Populus_trichocarpa_2   SAASAAAAAVAVNEMFGRKLEVKDLVLAGLESEAKVSGYHADNIAPAIMGGFVLIRSYDP  207
Solanum_tuberosum_2     SAASAAAAAVAVNELFGRPLTLTDLVLAGLDSESKVSGYHADNVAPALMGGFVLRSYHP   206
Vitis_vinifera          SAASAAAAAVAVNEIFGRKLGVDDLVLAGLDSEAKVSGYHANNVAPALMGGFVL1RSYDP  209
Lactuca_sativa          SAASAAAAAVAVNEIFGGKLHDSDLILAGLEAEAKLSGYHADNIAPAIMGGFVLIRSYDP  215
Solanum_tuberosum_1     SAASAAAAAVAVNBIFGRKLSVDDLVLAGLESETKVSGYHADNIAPSIMGGFVLVRSYDP  218
Solanum_lycopersicum    SAASAAAAAVAVNEIFGRKLSVDDLVLAGLESETKVSGYHADNIAPSIMGGFVLIRSYDP  218
Nicotiana_benthamiana   SAASAAAAAVAVNELFGGKLSVSDLVLAGLESETKVSGYHADNIAPAIMGGFVLIRSYDP  225
Ipomoea_nil             SAASAAAAAVAVNELFGSRLSVSDLVFAGLESESKVSGYHADNVAFSIMGGFVLIRSYDP  204
```

Fig. 1 cont.

```
Glycine_max          SAASAAAAAVAVNELFGKKLSVEELVLASLKSEEKVSGYHADNVAFSIMGGFVLIGSYSP  204
Phaseolus_vulgaris   SAASAAAAAVAVNEMFGKRLSVEDLVVASLKSEEKVSGYHADNVAPAIMGGFVLIQSYEP  208
Cucumis_sativus      SAASAAAAAIAVNGLFGGKLGVEELVLAGLKSEEKVSGYHADNVAFAIMGGFILIRNYEP  210
Spinacia_oleracea    SAASAAAAAVAVNSLFGSPLSPLDLVHAGLESESKVSGYHADNIAPAIMGGFILIRSYEP  211
Pinus_taeda          SAASAAAAAVAVNGLFGNKLTKSDLVLAGLESEAAVSGYHADNVAPSLMGGFVLVRSYSP  227
Zea_mays             SAASAAAAAKAVDALFGSRLGRDDLVLAGLESEKAVSGFHADNIAPAILGGFVLVRSYDP  220
Oryza_sativa         SAASAAAAAKAVDALFGSLLHQDDLVLAGLESEKAVSGFHADNIAPAILGGFVLVRSYDP  218
                     ********* **: :**   *   :*: *.*.:*  :*::**:*:.**:::***:*: .* *

I (dmr1-3)                V (dmr1-1)
                                          ▼                         ▼
Arabidopsis_thaliana LDLKPLRFPSDKDLFFVLVSPDFEAPTKKMRAALPTEIPMVHHVWNSSQAAALVAAVLEG  271
Citrus_sinensis      LDLMRLNFPEKKQLLFVLVTPEFEAPTKKMRAALPAEVGMPHHIWNCSQAGALVAAVLNG  265
Populus_trichocarpa_1 LELMSLQFPVEKDLIFVLVSPDFEAPTKKMRAALPAEIGMPHHVWNCSQAGAFVASVLQG  267
Populus_trichocarpa_2 LELMSLQFPVEKDLIFVLVSPDFEAPTKKMRAALPAEIGMSHHVWNCSQAGALVASVLQG  267
Solanum_tuberosum_2  LELIQLNFPHEKDLFFVLANPEFEAPTKKMREALPQEITMSHHIWNCSQAGALVASVLLG  266
Vitis_vinifera       LELIPLTFPSDKELFFVLVNPEFEAPTKKMRAALPSEIGMSDHVWNCSQAAALVASILQG  269
Lactuca_sativa       LELISLKFPPEKNLFFVLVNPEFQAQTKKMRAVLPTEITMSDHVWNCSQAAALVAGVLQG  275
Solanum_tuberosum_1  LELISLKFPPFEKDLFFVLVNPEFEAPTKKMRAVLPSEVTMSHHIWNCSQAGALVAAILQG  278
Solanum_lycopersicum LELIPLKFPPFEKDLFFVLVNPEFEAPTKKMRAVLPSEVTMSHHIWNCSQAGALVAAILQG  278
Nicotiana_benthamiana LELIELKFPLEKDLFFVLVNPEFEAPTKKMRAALPNEVTMSHHIWNSSQAGALVAAILQG  285
Ipomoea_nil          LELIQLKFPQEKSLFFVLVNPEFEAPTKKMRAALPAEITMSSHVWNCSQAGALVASVLQG  264
Glycine_max          LELMPLKFPAEKELYFVLVTPEIEAPTKKMRAALPTEIGMPHHVWNCSQAGALVASVLQG  264
Phaseolus_vulgaris   LRLIELKFPAEKELYFVLVSPEFEAPTKKMRAALPGEIAMAHHVWNCSQAGALVAAVLQG  268
Cucumis_sativus      LELIRLKFPVEKELFFVLVSPEFEAPTKKMRAALPAEVGMPHHVWNSSQAGALVAAVLQG  270
Spinacia_oleracea    LDLMKLEFPETNDLYFVLVSPEFEAPTKKMRAALPKEIGMPHHIWNSSQAAALVAAVLMG  271
Pinus_taeda          LDLIHLPFPSEKELFFVLVTPAFEAPTKEMRAVLPKNITMKDHIQNCSQAAALVAAILQG  287
Zea_mays             FHLVPLSFPPALRLHFVLVTPDFEAPTSKMRAALPRQVDVQQHVRNSSQAAALVAAVLQG  280
Oryza_sativa         FHLIPLSSPPALRLHFVLVTPDFEAPTSKMRAALPKQVAVHQHVRNSSQAAALVAAVLQG  278
                      : *   *   *    *** ..* :** *.:** .** :: :  *: *.***.*:**.:* *

Arabidopsis_thaliana DAVMLGKALSSDKIVEPTRAPLIPGMEAVKKAALEAGAFGCTISGAGPTAVAVIDSEEKG  331
Citrus_sinensis      DPVGLGKALSSDKIVEPNRAPLIPGMEAVKKVAVEAGAYGCTISGAGPTAVAVVDNEEKG  325
Populus_trichocarpa_1 DLVGLGKALSSDKIVEPKRAPLIPGMEAVKKAALEAGAFGCTISGAGPTAVAVVDSEERG  327
Populus_trichocarpa_2 DLVGLGKALSSDKIVEPKRAPLIPGMVGVKKAALEAGAFGCTISGAGPTAVAVVGSEDRG  327
Solanum_tuberosum_2  DVSGFGKALSSDKIVEPRRTPLIPGMEGVKKAAMEAGAFGCTIRGAGPTVVAVTDNEETG  326
Vitis_vinifera       DLRGLGKALSSDRIVEPRRAPLIPGMEAVKKAALEAGAFGCTISGAGPTAVAITDEEKG  329
Lactuca_sativa       DLVGFGKALSSDRIVEPRRAPLLPGMEDVKKAAMEAGAYGCTISGAGPTVVAVTDDEDRG  335
Solanum_tuberosum_1  DSRGLGKALSSDKIVEPRRGPLIPGMEGVKKAALKAGAFGCTISGAGPTLVAVTDDEERG  338
Solanum_lycopersicum DSRGLGKALSSDKIVEPRRGPLIPGMEGVKKAALKAGAFGCTISGAGPTLVAVTDDEERG  338
Nicotiana_benthamiana DSRGLGKALSSDKIVEPKRGPLIPGMEGVKKAALEAGAFGCTISGAGPTLVAVTDGEERG  345
Ipomoea_nil          DLPGLGKALSSDKIVEPRRAPLIPGMEAVKKAAIQAGAFGCTISGAGPTAVAVTDDEEKG  324
Glycine_max          DVVGLGKALSSDKIVEPRRAPLIPGMEAVKKAAIQAGAFGCTISGAGPTAVAVIDDEQTG  324
Phaseolus_vulgaris   DVVGLGKALSSDKIVEPRRAPLIPGMEAVKKAALQAGAFGCTISGAGPTAVAVIDDELAG  328
Cucumis_sativus      DTMGLGKALSSDKIVEPRRSPLIPGMDGVKKAAIAAGAFGCTISGAGPTAVAVIDNEEKG  330
Spinacia_oleracea    DVEGIGKAMSSDKVVEPRRAPLIPGMMAVKKAAIEGGAFGCTISGAGPTAVAVTDREEKG  331
Pinus_taeda          DPCLLGAALSSDSIVEPRRGPFIPGMMAVKAAALETGAFGCTISGAGPTAVAITDTAEKG  347
Zea_mays             DAGLIGSAMSSDGIVEPTRAPLIPGMAAVKAAALQAGALGCTISGAGPTVVAVIQGEERG  340
Oryza_sativa         DATLIGSAMSSDGIVEPTRAPLIPGMAAVKAAALEAGALGCTISGAGPTAVAVIDGEEKG  338
                     *  :* *:*** :*** * *:;*** ** .*: ** **** *:*** **:          *

Arabidopsis_thaliana QVIGEKMVEAFWKVGHLKSVASVKKLDNVGARLVNSVSR----370
Citrus_sinensis      KVIGEKMVEAFWKEGNLKAVSMVKRLDRVGARLVG5VRAPR--366
Populus_trichocarpa_1 VEIGERMVETFWKEGKLKAVASVKRLDRVGARLVGSVPR----366
Populus_trichocarpa_2 MEVGERMVEAFWKEGNLKAVAMVKRLDRVGARLVGSVPR----366
Solanum_tuberosum_2  REIGQRMVEVFLEHGKLKALAMVKKLDRIGARLVSSQPI----365
Vitis_vinifera       REIGERMVEAFLEEGKLKAVAMVKQLDRVGARLMSSILR----368
Lactuca_sativa       REIGEKMVEAFVEKGKLKALAMVKKLDRVGARVISRISSQ---375
Solanum_tuberosum_1  REIGERMVDAFMKEGNLKALAMVKKLDRVGARLVSSNS-----376
Solanum_lycopersicum REIGERMVEAFMKEGNLKALAMVKKLDRVGARLVSSNS-----376
Nicotiana_benthamiana REIGERMVEAFMKEGKLKALAMVKQLDRVGARLVSSNPR----384
Ipomea_nil           MEIGKRMVEAFIQEGNLKALAMVKRLDRVGARLVSKNGSICN-366
Glycine_max          HLIAKHMIDAFLHVGNLKASAMVKQLDRLGARRIPN-------360
Phaseolus_vulgaris   NAIAEHMIHAFLHHGNLKASAKVLQLDRLGARRILD ------364
Cucumis_sativus      KEIGERMVMAFLKEGNLKATASVKRLDRVGARLIGSTPLDRVL373
Spinacia_oleracea    REIGERMVEAFWKEGGLKAAAVIQKLDRVGARVVSSVPR----370
Pinus_taeda          KAIAVAMVDMFQKKGQLEATASVQKLDRIGARVV---------381
Zea_mays             EEVARKMVDAFWSAGKLKATATVAQLDTLGARVIATSSLN---380
Oryza_sativa         EEVGRRMVEAFANAGNLKATATVAQLDRVGARVISTSTLE---378
                     :.  *:  *  *  *:::  :  :  :** :***  :
```

Fig. 8

```
   1 CTCATTACTT GTTCATCAAT GGCAAGTCTT TGTTTCCAAT CTCCTTCCAA
  51 ACCCATTTCC TATTTCCAAC CCAAATCCAA TCCATCGCCG CCGTTATTCG
 101 CCAAAGTCTC CGTCTTTCGA TGCAGAGCTT CCGTACAAAC CCTCGTCGCC
 151 GTTGAGCCGG AGCCAGTTTT CGTCTCCGTC AAGACTTTTG CGCCAGCCAC
 201 CGTCGCTAAT TTAGGACCAG GGTTTGATTT CTTAGGATGC GCCGTCGATG
 251 GTCTCGGAGA CCATGTGACT CTCCGTGTAG ATCCCTCTGT ACGAGCCGGT
 301 GAGGTCTCAA TCTCGGAGAT CACCGGAACG ACAACAAAAC TCAGCACAAA
 351 TCCTCTCCGG AACTGCGCCG GAATCGCTGC TATTGCTACA ATGAAGATGT
 401 TAGGGATCAG ATCGGTTGGT TTATCATTAG ATTTGCATAA AGGTCTTCCT
 451 TTAGGTAGCG GTTTAGGTTC TAGTGCAGCT AGCGCCGCCG CAGCTGCTGT
 501 GGCGGTTAAT GAGATCTTTG GTCGGAAATT AGGGAGTGAT CAATTGGTAT
 551 TAGCCGGTTT AGAATCGGAA GCGAAAGTCT CCGGTTATCA CGCTGATAAT
 601 ATCGCACCAG CGATCATGGG TGGATTCGTT TTGATTCGAA ACTACGAACC
 651 ACTTGATTTG AAACCATTGA AGTTCCCATC TGATAAAGAT CTCTTCTTTG
 701 TTCTAGTAAG CCCTGAGTTT GAAGCTCCAA CTAAGAAAAT GAGAGCTGCA
 751 TTGCCTACAG AGATTCCAAT GGTTCATCAT GTTTGGAACA GTAGCCAAGC
 801 AGCTGCTTTA GTCGCTGCTG TGTTAGAAGG TGACGCAGTG ATGCTTGGGA
 851 AGGCATTGTC GTCGGATAAG ATTGTGGAGC CAACTAGAGC GCCTTTGATT
 901 CCGGGGATGG AAGCTGTGAA GAAGGCAGCT TTGGAAGCTG GAGCGTTTGG
 951 ATGTACAATT AGCGGAGCTG GACCAACAGC AGTTGCGGTG ATTGATTCGG
1001 AGGAGAAGGG TCAAGTGATT GGAGAGAAGA TGGTGGAAGC GTTTTGGAAA
1051 GTTGGTCATT TGAAATCTGT TGCTTCTGTG AAGAAGCTTG ATAAGGTTGG
1101 TGCTAGGCTT GTCAACAGCG TCTCCAGATG ATCTTTTAAT GATGTTTGAT
1151 TATGCTAAGA TTGGAACAAA TCTTCCTTTG TACTGTAATT TCTAGATGAT
1201 AATAAAGTTG TTTGTTTTCT ACACT
```

SEQ ID NO: 99

Fig. 9

```
  1 MASLCFQSPS KPISYFQPKS NPSPPLFAKV SVFRCRASVQ TLVAVEPEPV
 51 FVSVKTFAPA TVANLGPGFD FLGCAVDGLG DHVTLRVDPS VRAGEVSISE
101 ITGTTTKLST NPLRNCAGIA AIATMKMLGI RSVGLSLDLH KGLPLGSGLG
151 SSAASAAAAA VAVNEIFGRK LGSDQLVLAG LESEAKVSGY HADNIAPAIM
201 GGFVLIRNYE PLDLKPLRFP SDKDLFFVLV SPDFEAPTKK MRAALPTEIP
251 MVHHVWNSSQ AAALVAAVLE GDAVMLGKAL SSDKIVEPTR APLIPGMEAV
301 KKAALEAGAF GCTISGAGPT AVAVIDSEEK GQVIGEKMVE AFWKVGHLKS
351 VASVKKLDNV GARLVNSVSR
```

SEQ ID NO: 100

Fig. 10

>Lactuca sativa HSK CDS
ATGGCAATTCGCCATTATCAACCTCCATTCGCCTCCACTTCTTCTTCTATCTCTAGTACA
GATTTATTCAAACCCCCTAAACTTTATCTTTCATCGTCTGTCCGGTGCAACATCTCCGTC
GCTTCCAAACTGGAACCCGAACCTCATCCAGTTTTCACCTCCGTTAAGTCATTCGCCCCC
GCCACCGTAGCCAACCTCGGGCCTGGTTTCGACTTCCTCGGCTGCGCAATCGACGGCATC
GGAGATTACGTTACCCTCACAGTCGACCCCCAAGTCCAACCCGGCAGATTATCAATTGCA
GAAATCAACGGCGTTGACAAGTCTTCCAAGAGGCTCAGCAGAAACCCTCTATGGAATTGC
GCCGGAATTGCTGCAATCTCCGTCATGAAGATGCTCAAGATCCGATCCGTTGGTCTCTCT
TTATCCATCAATACATGTCTCCCCCTTCGAGGCGGCCTAGGCTCCAGCGCCGCTAGCGCT
GCCGCCGCCGCCGTTGCGGTTAATGAGATTTTCGGAGGGAAGTTACATGATTCCGATTTG
ATACTCGCGGGGCTCGAAGCTGAAGCGAAGTTATCCGGTTATCACGCCGATAACATTGCT
CCGGCGATCATGGGCGGGTTTGTGTTGATCAGAAGCTACGATCCATTAGAGTTGATCTCC
TTGAAGTTTCCACCGGAAAAGAATCTGTTTTTCGTGTTGGTGAATCCTGAATTCCAAGCA
CAAACGAAGAAGATGAGGGCGGTTCTACCGACGGAGATAACAATGTCGGATCATGTATGG
AATTGTAGTCAGGCGGCGGCGTTGGTGGCAGGCGTATTGCAGGGGGATTTGGTGGGGTTT
GGGAAGGCATTGTCATCGGATAGAATAGTGGAGCCACGGCGGGCGCCATTGCTTCCGGGA
ATGGAAGATGTGAAGAAGGCAGCAATGGAAGCAGGGGCATATGGGTGTACGATAAGTGGG
TCAGGGCCGACGGTGGTGGCGGTGACGGATGATGAAGATAGAGGGAGGGAGATCGGGGAG
AAGATGGTGGAAGCTTTTGTAGAGAAGGGAAAGTTGAAAGCTTTGGCTATGGTGAAGAAA
CTGGACAGAGTTGGTGCTAGAGTTATCAGTCGTATCTCCAGCCAATGA

SEQ ID NO: 101

>Lactuca sativa HSK protein
MAIRHYQPPFASTSSSISSTDLFKPPKLYLSSSVRCNISVASKLEPEPHPV
FTSVKSFAPATVANLGPGFDFLGCAIDGIGDYVTLTVDPQVQPGRLSIAEINGVDKSSKR
LSRNPLWNCAGIAAISVMKMLKIRSVGLSLSINTCLPLRGGLGSSAASAAAAAVAVNEIF
GGKLHDSDLILAGLEAEAKLSGYHADNIAPAIMGGFVLIRSYDPLELISLKFPPEKNLFF
VLVNPEFQAQTKKMRAVLPTEITMSDHVWNCSQAAALVAGVLQGDLVGFGKALSSDRIVE
PRRAPLLPGMEDVKKAAMEAGAYGCTISGSGPTVVAVTDDEDRGREIGEKMVEAFVEKGK
LKALAMVKKLDRVGARVISRISSQ*

SEQ ID NO: 102

Fig. 11

>Vitis vinifera HSK CDS
ATGGCGATTTGCTTCCACTCCCCCTCAAAACCCACTTGCATTTCTCCCTCATCAAACCATTACAGACCCAATCTT
CATGCTCGGTCCTTCAGATGCAACTTCTCTAAAACATTAACTGCTGATCCTCAACCAGTTTTCACCTCTGTGAAG
TCCTTCGCACCCGCAACCGTTGCTAACCTCGGTCCCGGTTTCGATTTCCTCGGTGCTGCTGTTGATGGTATAGGC
GATTTCGTCTCCCTTCGCGTGGATCCTGATGTTCGGCCCGGGGAGATTTCGATTGTCGATATCGATGGTGTTGGG
AATAGCGCCAAGAAGCTCAGTAAAAATCCCCTCTGGAACTGCGCCGGCATTGCCGCTATCTCCGTCATGAAAATG
CTCGGAGTCCGATCGGTGGGGCTGTCCCTTTCCCTCGAGAAGGGGTTGCCATTGGGAAGTGGACTTGGGTCGAGC
GCTGCCAGTGCCGCCGCGGCTGCTGTGGCGGTGAATGAGATTTTTGGGCGGAAATTGGGAGTTGATGACCTTGTC
CTTGCTGGGCTTGACTCGGAAGCTAAAGTTTCGGGTTATCACGCGAACAATGTqGCGCCGGCTCTTATGGGAGGA
TTCGTGTTGATTCGGAGTTATGATCCTTTGGAGTTGATTCCTTTGACGTTTCCGAGCGACAAGGAGTTGTTTTTT
GTGTTGGTGAATCCGGAATTTGAAGCTCCCACCAAGAAAATGCGGGCGGCATTGCCGTCGGAGATCGGGATGTCT
GATCACGTGTGGAATTGTAGCCAGGCCGCTGCATTGGTAGCCTCGATTTTGCAAGGAGA~TTGAGGGGGTTGGGC
AAGGCATTGTCCTCCGACAGAATTGTGGAGCCAAGGAGGGCACCCTTGATCCCTGGGATGGAAGGAGTGAAAAAG
GCTGCTCTTGAGGCTGGTGCATTTGGCTGTACAATTAGTGGAGCAGGGCCGACTGCAGTTGCAATTACAGATGAC
GAAGAGAAGGGAAGGGAGATTGGAGAACGGATGGTAGAAGCTTTCTTGGAGGAAGGGAAGTTGAAGGCTGTAGCA
ATGGTGAAGCAACTCGATAGGGTTGGTGCTAGGCTTATGAGTAGCATCCTCAGATGA

SEQ ID NO: 103

>Vitis vinifera HSK protein MAICFHSPSKPTCISPSSNHYRPNLHARSFRCNFS
KTLTADPQPVFTSVKSFAPATVANLGPGFDFLGAAVDGIGDFVSLRVDPDVRPGEISIVD
IDGVGNSAKKLSKNPLWNCAGlAAISVMKMLGVRSVGLSLSLEKGLPLGSGLGSSAASAA
AAAVAVNEIFGRKLGVDDLVLAGLDSEAKVSGYHANNVAPALMGGFVLIRSYDPLELIPL
TFPSDKELFFVLVNPEFEAPTKKMRAALPSEIGMSDHVWNCSQAAALVASILQGDLRGLG
KALSSDRIVEPRRAPLIPGMEGVKKAALEAGAFGCTISGAGPTAVAITDDEEKGREIGER
MVEAFLEEGKLKAVAMVKQLDRVGARLMSSILR*

SEQ ID NO: 104

Fig. 12

>Cucumis sativus HSK CDS
ATGGCTATGCTCTCCTATCAACCGCCATTGAAGTCGTTGACCATTCCTCCAGTTTCTTTATCTAACCCTAAACCT
GTTCTCTTCAGGTGCAGTTTGTCTCTTCCATCTAGAACCGCCGTCACTTCCGTCGAACCTCAACCCGTTTTCTCT
TCCGTCAAGGCGTTTGCTCCTGCAACCGTCGCTAATTTAGGTCCTGGGTTTGATTTCCTTGGCTGCGCTGTTGAT
GGCTTGGGAGATTATGTCTCTCTTAGTGTTGATTCCAATGTTCATCCAGGTGAAGTTGCGATTTCTGATATTACA
GGGAATAACACGAATAAACTTAGTAAAAATCCTCTCTATAATTGTGCTGGTATTGCTGCTATTGAAGTTATGAAA
ATGCTAGGGATCCGATCTGTTGGTCTTTCTCTTTCGCTTGAGAAAGGTTTGCCGTTAGGGAGTGGATTGGGATCT
AGTGCTGCGAGTGCAGCTGCTGCGGCGATTGCTGTTAATGGATTGTTCGGTGGGAAATTAGGAGTAGAGGAATTG
GTTCTCGCGGGGTTGAAATCGGAAGAGAAGGTTTCTGGGTACCATGCGGATAA1GTCGCACCGGCTATCATGGGG
GGTTTCATTCTGATTCGAAATTACGAACCCTTGGAATTGATTCGTTTGAAATTCCCCGTCGAGAAGGAGCTGTTC
TTCGTGTTGGTCAGCCCGGAATTCGAAGCACCGACGAAGAAAATGCGGGCTGCGTTACCTGCTGAAGTTGGGATG
CCACACCATGTGTGGAATTCCAGCCAAGCCGGGGCGTTGGTGGCTGCGGTGCTGCAGGGT~ACACGATGGGATTG
GGGAAAGCATTGTCATCAGACAAAATTGTGGAACCAAGGCGTTCGCCGTTGATTCCAGGTATGGATGGTGTTAAG
AAGGCAGCCATTGCTGCTGGGGCATTTGGGTGCACGATAAGCGGAGCAGGGCCAACAGCGGTGGCGGTGATCGAT
AACGAAGAGAAGGGGAAGGAGATTGGTGAGAGGATGGTTATGGCATTTCTGAAGGAAGGAAATTTGAAAGCTACG
GCATCTGTAAAGAGACTAGATCGAGTTGGTGCAAGGCTTATTGGATCAACTCCTTTAGATAGAGTTTTATGA

SEQ ID NO: 105

>Cucumis sativus HSK protein
MAMLSYQPPLKSLTIPPVSLSNPKPVLFRCSLSLPSRTAVTSVEPQPVFSSVKAFAPA
TVANLGPGFDFLGCAVDGLGDYVSLSVDSNVHPGEVAISDITGNNTNKLSKNPLYNCAGI
AAIEVMKMLGIRSVGLSLSLEKGLPLGSGLGSSAASAAAAAIAVNGLFGGKLGVEELVLA
GLKSEEKVSGYHADNVAPAIMGGFILIRNYEPLELIRLKFPVEKELFFVLVSPEFEAPTK
KMRAALPAEVGMPHHVWNSSQAGALVAAVLQGDTMGLGKALSSDKIVEPRRSPLIPGMDG
VKKAAIAAGAFGCTISGAGPTAVAVIDNEEKGKEIGERMVMAFLKEGNLKATASVKRLDR VGARLIGSTPLDRVL*

SEQ ID NO: 106

Fig. 13

>Spinacia oleracea HSK CDS
ATGGCAATCTGCGCACAATCTCCATTCAAACCCGTCAATCTATCACCTCACTCCCCTTCTCCCACCCACAAATCC
CCATTCATCTGTAAACTTTCTCTCTCCTCCCACTCAACCCACTCACCTCTCACCACTGAACCAACACCACTCCTC
ACCTCCGTCACCACCTTCGCCCCCGCTACCGTCGCCAACCTCGGCCCAGGGTTCGACTTCCTCGGTTGCGCTGTC
GATGGCCTCGGTGACTTCGTTTCTCTTTCCGTTGACCCCTCCGTTCATCCCGGTCAACTCTCCATCTCCTCCATT
TCCGGCGACGCTTCTTCCAAACTCTCCAAAGATCCCCTTCTTAACTGCGCCGGTATCTCTGCCCTAGCCGCCATG
AAGCTCCTTAACATTCGCTCCGTCGGCCTTTCTCTATCTCTCCAAAAAGGGCTCCCACTTGGCTCCGGTCTCGGA
TCTTCAGCAGCTTCCGCTGCTGCTGCCGCTGTTGCTGTGAACTCCCTATTTGGCTCCCCTCTCTCTCCACTCGAC
CTCGTACACGCTGGACTTGAGTCAGAATCTAAAGTTTCCGGTTACCACGCTGACAACATTGCACCGGCGATAATG
GGTGGTTTTATCTTAATCAGGAGTTATGAGCCATTGGATTTGATGAAATTGGAGTTCCCTGAGACTAATGATTTG
TATTTCGTATTGGTTAGTCCGGAATTTGAAGCCCCAACGAAGAAGATGAGGGCGGCATTGCCGAAGGAGATCGGG
ATGCCGCACCACATATGGAATTCTAGCCAAGCGGCAGCATTGGTGGCGGCAGTTTTGATGGGTGACGTAGAAGGG
ATAGGAAAGGCAATGTCTTCCGATAAAGTGGTGGAGCCAAGGCGGGCACCATTGATTGCCGGGATGATGGCGGTG
AAGAAGGCGGCTATTGAAGGGGGAGCGTTCGGGTGTACAATTAGCGGGGCAGGGCCTACGGCTGTGGCAGTAACG
GATAGGGAGGAGAAGGGAAGAGAGATCGGAGAGAGAATGGTGGAAGCGTTTTGGAAGGAAGGAGGGTTAAAGGCT
GCCGCTGTGATTCAAAAGCTAGATAGAGTTGGTGCTAGAGTTGTTAGCAGTGTTCCCAGATGA

SEQ ID NO: 107

>Spinacia oleracea HSK protein MAICAQSPFKPVNLSPHSPSPTHKSPFICKLSLSSHSTH
SPLTTEPTPLLTSVTTFAPATVANLGPGFDFLGCAVDGLGDFVSLSVDPSVHPGQLSISS
ISGDASSKLSKDPLLNCAGISALAAMKLLNIRSVGLSLSLQKGLPLGSGLGSSAASAAAA
AVAVNSLFGSPLSPLDLVHAGLESESKVSGYHADNIAPAIMGGFILIRSYEPLDLMKLEF
PETNDLYFVLVSPEFEAPTKKMRAALPKEIGMPHHIWNSSQAAALVAAVLMGDVEGIGKA
MSSDKVVEPRRAPLIPGMMAVKKAAIEGGAFGCTISGAGPTAVAVTDREEKGREIGERMV
EAFWKEGGLKAAAVIQKLDRVGARVVSSVPR*

SEQ ID NO: 108

Fig. 14

>Solanum lycopersicum HSK CDS
ATGGCTATAACCTTTCAATCTCCCATGAAACTCAGCTTCATCACTTCTAATGGCTTCTCAAATCCTCC
TTCTCTTTATCCCATCAATACCCATTTCTCATTTGGATTCAATCTCTCATCTGTCTCCTCCAAAACCC
AAACCCATATCACCATACCCGAACCCGAACCCGTATTCACCTCCGTCAAGTCGTTTGCTCCGGCCACT
GTTGCTAATCTAGGTCCGGGTTTTGATTTCCTCGGATGCGCCGTTGATGGAGTCGGAGATTTTGTCAC
TCTTCGGGTTGACCCAAATGTTAAAGCTGGGGAGGTTTCGATTTCTGATATCTCCGGTGCTGGAAATA
GGCTTAGTAAAGACCCTTTATCGAACTGTGCTGGAATAGCTGCTATTTCTGTTATGAAGATGTTGAAT
ATACAGTCTGTTGGTTTATCGATTTCGCTTGAAAAAGGGTTGCCGTTGGGTAGTGGACTTGGGTCTAG
TGCTGCTAGTGCTGCGGCGGCGGCGGTGGCTGTGAATGAGATTTTTGGACGGAAGTTGAGTGTTGATG
ATCTTGTGCTTGCTGGGTTGGAATCGGAAACGAAGGTTTCGGGTTATCATGCTG~TAATATAGCACCT
TCGATTATGGGTGGTTTTGTGTTGATAAGAAGTTATGATCCGTTGGAATTGATCCCATTGAAGTTTCC
ATTTGAAAAAGATTTGTTTTTTGTGCTTGTGAATCCCGAATTCGAAGCTCCAACGAAGAAGATGAGGG
CGGTATTGCCATCGGAGGTGACAATGTCGCATCATATATGGAATTGTAGTCAGGCTGGGGCGTTGGTG
GCTGCGATATTGCAGGGGGATTCGAGGGGTTTAGGGAAGGCGTTGTCGTCTGATAAGATTGTGGAGCC
GAGGAGAGGGCCGTTGATTCCTGGGATGGAGGGAGTGAAGAAGGCGGCGTTGAAGGCTGGGGCATTTG
GTTGCACGATAAGCGGAGCTGGACCTACTTTGGTCGCGGTGACGGATGATGAAGAGAGAGGGAGGGAG
ATTGGGGAGAGAATGGTGGAGGCGTTTATGAAGGAAGGGAACTTGAAGGCTTTGGCTATGGTGAAGAA
GCTTGATCGAGTTGGTGCCCGCCTTGTTAGTAGCAATTCATGA

SEQ ID NO: 109

> Solanum lycopersicum HSK protein
MAITFQSPMKLSFITSNGFSNPPSLYPINTHFSFGFNLSSVSSKTQTHITIPEPEPVFTS
VKSFAPATVANLGPGFDFLGCAVDGVGDFVTLRVDPNVKAGEVSISDISGAGNRLSKDPL
SNCAG1AAISVMKMLNIQSVGLSISLEKGLPLGSGLGSSAASAAAAAVAVNEIFGRKLSV
DDLVLAGLESETKVSGYHADNIAPSIMGGFVLIRSYDPLELIPLKFPFEKDLFFVLVNPE
FEAPTKKMRAVLPSEVTMSHHIWNCSQAGALVAAILQGDSRGLGKALSSDKIVEPRRGPL
IPGMEGVKKAALKAGAFGCTISGAGPTLVAVTDDEERGREIGERMVEAFMKEGNLKALAM
VKKLDRVGARLVSSNS*

SEQ ID NO: 110

DISEASE RESISTANT PLANTS

CROSS-REFERENCE TO RELATED APPLICATIONS

This application is a divisional application of U.S. patent application Ser. No. 13/713,332, filed Dec. 13, 2012, and issued as U.S. Pat. No. 8,575,432, which is a divisional application of U.S. patent application Ser. No. 13/545,853, filed Jul. 10, 2012, and issued as U.S. Pat. No. 8,354,570, which is a divisional application of U.S. patent application Ser. No. 12/092,253, filed Dec. 19, 2008, and issued as U.S. Pat. No. 8,237,019, which is a U.S. National Phase application filed under 35 U.S.C. §371 claiming priority to PCT Application No. PCT/EP2006/010535, filed Nov. 1, 2006 and which claims priority to PCT Application No. PCT/EP2005/011718, filed Nov. 1, 2005, each of which is incorporated herein by reference in their entirety.

The Sequence Listing associated with this application is filed in electronic format via EFS-Web and is hereby incorporated by reference into the specification in its entirety. The name of the text file containing the Sequence Listing is 132482_ST25.txt. The size of the text file is 90,740 bytes, and the text file was created on Aug. 14, 2013.

BACKGROUND OF THE INVENTION

The present invention relates to disease resistant plants, in particular plants resistant to organisms of the phylum Oomycota, the oomycetes. The invention further relates to plant genes conferring disease resistance and methods of obtaining such disease resistant plants for providing protection to Oomycota pathogens.

Resistance of plants to pathogens has been extensively studied, for both pathogen specific and broad resistance. In many cases resistance is specified by dominant genes for resistance. Many of these race-specific or gene-for-gene resistance genes have been identified that mediate pathogen recognition by directly or indirectly interacting with avirulence gene products or other molecules from the pathogen. This recognition leads to the activation of a wide range of plant defence responses that arrest pathogen growth.

In plant breeding there is a constant struggle to identify new sources of mostly monogenic dominant resistance genes. In cultivars with newly introduced single resistance genes, protection from disease is often rapidly broken, because pathogens evolve and adapt at a high frequency and regain the ability to successfully infect the host plant. Therefore, the availability of new sources of disease resistance is highly needed.

Alternative resistance mechanisms act for example through the modulation of the defence response in plants, such as the resistance mediated by the recessive m/o gene in barley to the powdery mildew pathogen *Blumeria graminis* fsp. *hordei*. Plants carrying mutated alleles of the wildtype MLO gene exhibit almost complete resistance coinciding with the abortion of attempted fungal penetration of the cell wall of single attacked epidermal cells. The wild type MLO gene thus acts as a negative regulator of the pathogen response. This is described in WO9804586.

Other examples are the recessive powdery mildew resistance genes, found in a screen for loss of susceptibility to *Erysiphe cichoracearum*. Three genes have been cloned so far, named PMR6, which encodes a pectate lyase-like protein, PMR4 which encodes a callose synthase, and PMR5 which encodes a protein of unknown function. Both mlo and pmr genes appear to specifically confer resistance to powdery mildew and not to oomycetes such as downy mildews.

Broad pathogen resistance, or systemic forms of resistance such as SAR, has been obtained by two main ways. The first is by mutation of negative regulators of plant defence and cell death, such as in the cpr, lsd and acd mutants of *Arabidopsis*. The second is by transgenic overexpression of inducers or regulators of plant defence, such as in NPR1 overexpressing plants.

The disadvantage of these known resistance mechanisms is that, besides pathogen resistance, these plants often show detectable additional and undesirable phenotypes, such as stunted growth or the spontaneous formation of cell death.

It is an object of the present invention to provide a form of resistance that is broad, durable and not associated with undesirable phenotypes.

In the research that led to the present invention, an *Arabidopsis thaliana* mutant screen was performed for reduced susceptibility to the downy mildew pathogen *Hyaloperonospora parasitica*. EMS-mutants were generated in the highly susceptible *Arabidopsis* line Ler eds 1-2. Eight downy mildew resistant (dmr) mutants were analysed in detail, corresponding to 6 different loci. Microscopic analysis showed that in all mutants *H. parasitica* growth was severely reduced. Resistance of dmr3, dmr4 and dmr5 was associated with constitutive activation of plant defence. Furthermore, dmr3 and dmr4, but not dmr5, were also resistant to *Pseudomonas syringae* and *Golovinomyces orontii*.

In contrast, enhanced activation of plant defense was not observed in the dmr1, dmr2, and dmr6 mutants. The results of this research have been described in Van Damme et al. (2005) Molecular Plant-Microbe Interactions 18(6) 583-592. This article does however not disclose the identification and characterization of the DMR genes.

BRIEF SUMMARY OF THE INVENTION

According to the present invention it was now found that DMR1 is the gene encoding homoserine kinase (HSK). For *Arabidopsis* five different mutant dmr1 alleles have been sequenced each leading to a different amino acid change in the HSK protein. HSK is a key enzyme in the biosynthesis of the amino acids methionine, threonine and isoleucine and is therefore believed to be essential. The various dmr1 mutants show defects in HSK causing the plants to accumulate homoserine. The five different alleles show different levels of resistance that correlate to different levels of homoserine accumulation in the mutants.

The present invention thus provides a plant, which is resistant to a pathogen of viral, bacterial, fungal or oomycete origin, characterized in that the plant has an altered homoserine level as compared to a plant that is not resistant to the said pathogen.

This form of resistance is in particular effective against pathogens of the phylum Oomycota, such as *Albugo, Aphanomyces, Basidiophora, Bremia, Hyaloperonospora, Pachymetra, Paraperonospora, Perofascia, Peronophythora, Peronospora, Peronosclerospora, Phytium, Phytophthora, Plasmopara, Protobremia, Pseudoperonospora, Sclerospora, Viennotia* species.

The resistance is based on an altered level of homoserine in planta. More in particular, the resistance is based on an increased level of homoserine in planta. Such increased levels can be achieved in various ways.

First, homoserine can be provided by an external source. Second, the endogenous homoserine level can be increased. This can be achieved by lowering the enzymatic activity of the homoserine kinase gene which leads to a lower conversion of homoserine and thus an accumulation thereof. Alternatively, the expression of the homoserine kinase enzyme can be reduced. This also leads to a lower conversion of homoserine and thus an accumulation thereof. Another way to increase the endogenous homoserine level is by increasing its biosynthesis via the aspartate pathway. Reducing the expression of the homoserine kinase gene can in itself be achieved in various ways, either directly, such as by gene silencing, or indirectly by modifying the regulatory sequences thereof or by stimulating repression of the gene.

Modulating the HSK gene to lower its activity or expression can be achieved at various levels. First, the endogenous gene can be directly mutated. This can be achieved by means of a mutagenic treatment. Alternatively, a modified HSK gene can be brought into the plant by means of transgenic techniques or by introgression, or the expression of HSK can be reduced at the regulatory level, for example by modifying the regulatory sequences or by gene silencing.

In one embodiment of the invention, an increase (accumulation) in homoserine level in the plant is achieved by administration of homoserine to the plant. This is suitably done by treating plants with L-homoserine, e.g. by spraying or infiltrating with a homoserine solution.

Treatment of a plant with exogenous homoserine is known from WO00/70016. This publication discloses how homoserine is applied to a plant resulting in an increase in the phenol concentration in the plant. The publication does not show that plants thus treated are resistant to pathogens. In fact, WO00/70016 does not disclose nor suggest that an increase in endogenous homoserine would lead to pathogen resistance.

Alternatively, endogenous homoserine is increased by modulating plant amino acid biosynthetic or metabolic pathways.

In one embodiment, the increased endogenous production is the result of a reduced endogenous HSK gene expression thus leading to a less efficient conversion of homoserine into phospho-homoserine and the subsequent biosynthesis of methionine and threonine. This reduced expression of HSK is for example the result of a mutation in the HSK gene leading to reduced mRNA or protein stability.

In another embodiment reduced expression can be achieved by downregulation of the HSK gene expression either at the transcriptional or the translational level, e.g. by gene silencing or by mutations in the regulatory sequences that affect the expression of the HSK gene. An example of a method of achieving gene silencing is by means of RNAi.

In a further embodiment the increase in endogenous homoserine level can be obtained by inducing changes in the biosynthesis or metabolism of homoserine. In a particular embodiment this is achieved by mutations in the HSK coding sequence that result in a HSK protein with a reduced enzymatic activity thus leading to a lower conversion of homoserine into phospho-homoserine. Another embodiment is the upregulation of genes in the aspartate pathway causing a higher production and thus accumulation of L-homoserine in planta.

BRIEF DESCRIPTION OF THE DRAWINGS

FIG. 1 shows orthologous HSK sequences that have been identified in publicly available databases and obtained by PCR amplification on cDNA and subsequent sequencing. FIG. 1 shows the alignment of the amino acid sequences of the HSK proteins of *Arabidopsis* thaliana and orthologs from *Citrus sinensis, Populus trichocarpa* (1), *Populus trichocarpa* (2), *Solanum tuberosum* (2), *Vitis vinifera, Lactuca sativa, Solanum tuberosum* (1), *Solanum lycopersicum, Nicotiana benthamiana, Ipomoea nil, Glycine max, Phaseolus vulgaris, Cucumis sativus, Spinacia oleracea, Pinus taeda, Zea mays*, and *Oryza sativa* using the CLUSTAL W (1.82) multiple sequence alignment programme (EBI). Below the sequences the conserved amino acids are indicated by the dots, and the identical amino acids are indicated by the asteriks. The black triangles and corresponding text indicate the amino acids that are substituted in the five *Arabidopsis* dmr mutants.

Table 2 shows the Genbank accession numbers and Gen-Info identifiers of the *Arabidopsis* HSK mRNA and orthologous sequences from other plant species.

Figure 2:
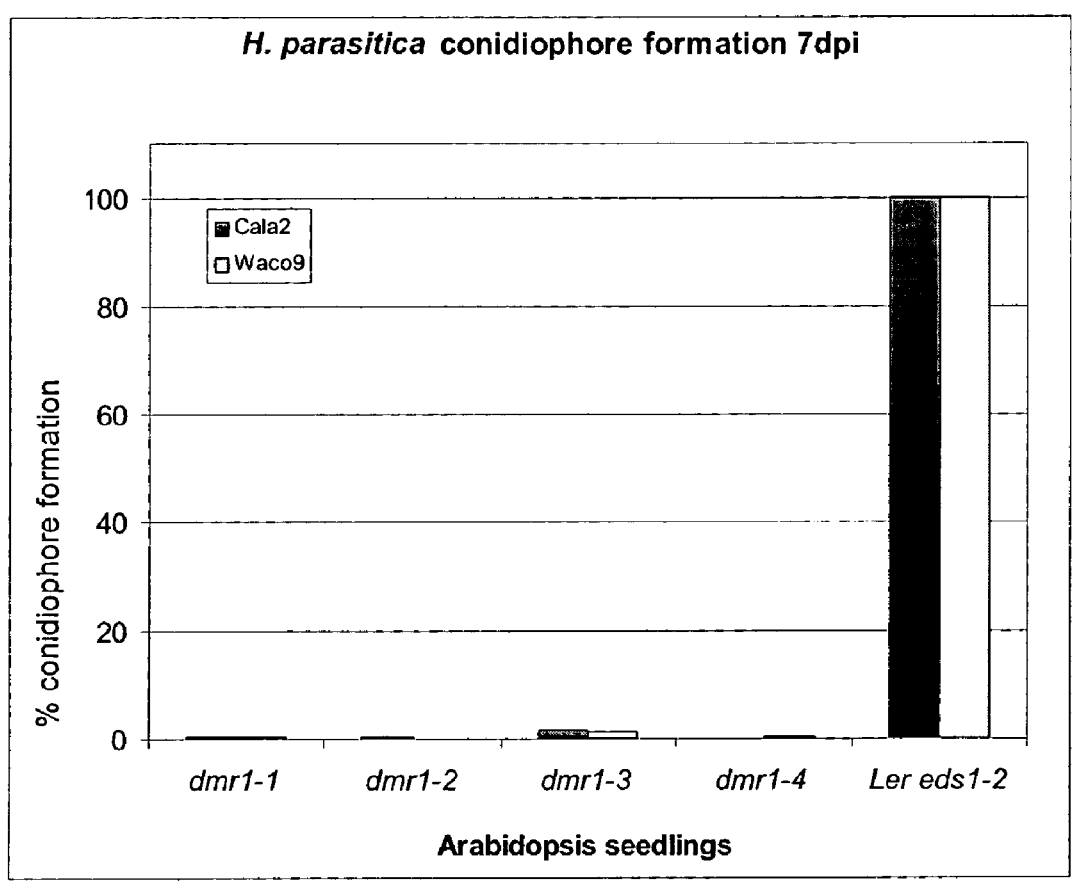

FIG. 2 shows the percentage of conidiophore formation by two *Hyaloperonospora parasitica* isolates, Cala2 and Waco9, on the mutants dmr1-1, dmr1-2, dmr1-3 and dmr1-4 and the parental line, Ler eds 1-2, 7 days post inoculation. The conidiophores formed on the parental line were set to 100%.

Figure 3:
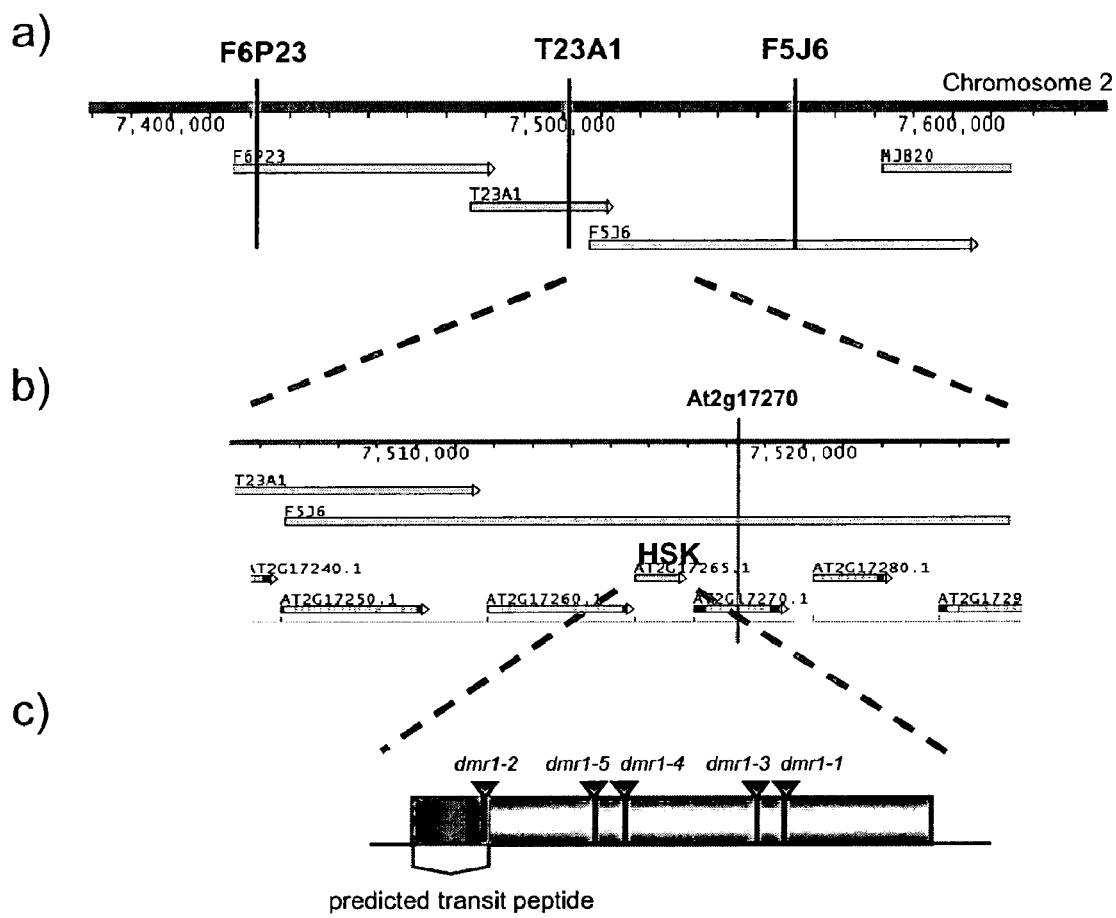

FIG. 3 is a graphic overview of the three major steps in the cloning of DMR1. a) Initial mapping of dmr1 resulted in positioning of the locus on the lower arm of chromosome 2 between positions 7.42 and 7.56 Mb. Three insert/deletion (INDEL) markers were designed (position of the markers F6P23, T23A1 and F5J6 is indicated by the black lines). These markers were used to identify recombinants from several 100 segregating F2 and F3 plants. Primer sequences of these INDEL markers and additional markers to identify the breakpoints in the collected recombinants is presented in table 3. b) One marker, At2g17270 (indicated by the grey line), showed the strongest linkage with resistance. The dmr1 locus could be further delimited to a region containing 8 genes, at2g17250-at2g17290. The eight genes were amplified and sequenced to look for mutations in the coding sequences using the primers described in table 4. DNA sequence analysis of all 8 candidate genes led to the discovery of point mutations in the At2g17265 gene in all 5 dmr1 mutants. c) Each dmr1 mutant has a point mutation at a different location in the At2g17265 gene, which encodes homoserine kinase.

Figure 4:
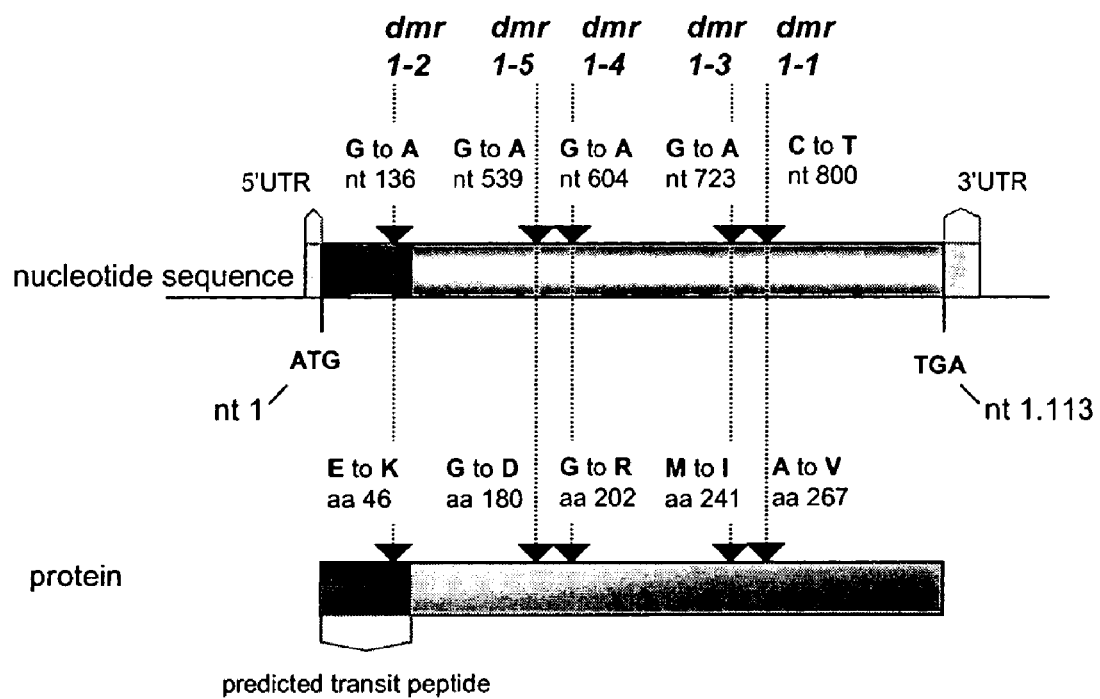

FIG. 4 shows a schematic drawing of the HSK coding sequence and the positions and nucleotide substitutions of the 5 different dmr1 mutations in the HSK coding sequence (the nucleotide positions, indicated by the black triangles, are relative to the ATG start codon which start on position 1). The 5'UTR and 3'UTR are shown by light grey boxes. Below the nucleotide sequence the protein sequence is shown. The HSK protein contains a putative transit sequence for chloroplast targeting (dark grey part). The amino acid changes resulting from the 5 dmr1 mutations are indicated at their amino acid (aa) position number (black triangles) in the HSK protein.

Figure 5:
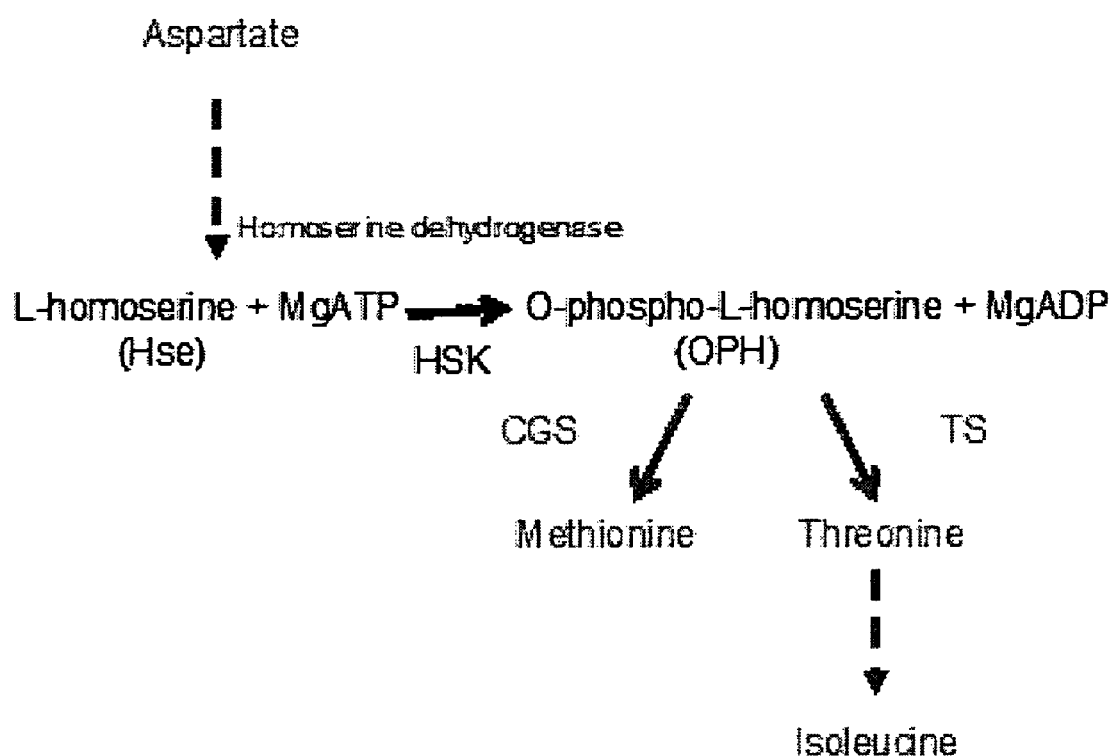

FIG. 5 shows the position of the homoserine kinase enzyme in the aspartate pathway for the biosynthesis of the amino acids threonine, methionine and isoleucine.

Figure 6:
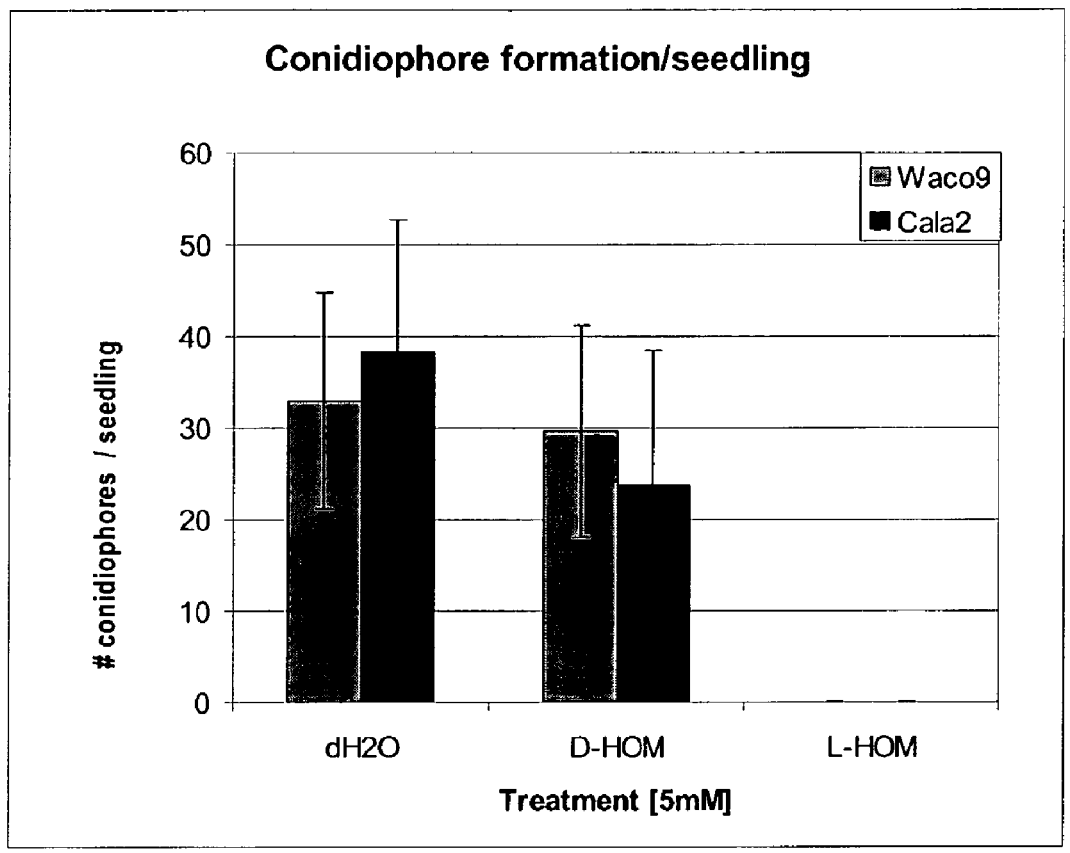

FIG. 6 shows the number of conidiophores per Ler eds 1-2 seedlings 5 days post inoculation with two different isolates of *H. parasitica*, Waco9 and Cala2. The inoculated seedlings were infiltrated with dH2O, D-homoserine (5 mM) or L-homoserine (5 mM) at 3 days post inoculation with the pathogen. Seedlings treated with L-homoserine show a complete absence of conidiophore formation and are thus resistant.

Figure 7:
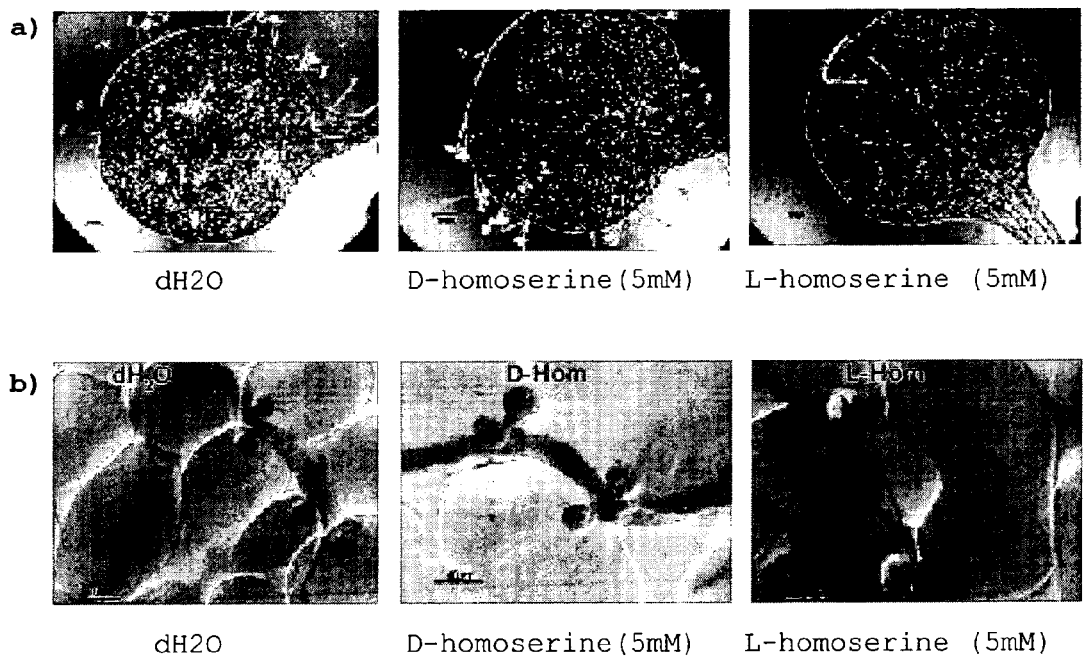

FIG. 7 shows the growth and development of *H. parasitica* in seedlings treated with water, D-homoserine (5 mM), or L-homoserine (5 mM) as analysed by microscopy of trypan blue stained seedlings.

a: Conidiophore formation after HS treatment on Ler eds 1-2 seedlings (10× magnification). No conidiophore formation was detected after L-homoserine infiltration, whereas control plants show abundant sporulation.

b: Haustorial development is affected by L-homoserine (5 mM) infiltration (40× magnification), but not in plants treated with water or D-homoserine.

FIGS. 8 and 9 show the nucleotide and amino acid sequence of the homoserine kinase gene (At2g17265, NM 127281, GI:18398362) and protein (At2g17265, NP_179318, GI:15227800) of *Arabidopsis thaliana*, respectively (SEQ ID NOs: 99-100).

FIG. 10 shows the nucleotide and the predicted amino acid sequence of the homoserine kinase coding sequence (CDS) and protein, respectively, of *Lactuca sativa* (SEQ ID NOs. 101-102)

FIG. 11 shows the nucleotide and the predicted amino acid sequence of the homoserine kinase coding sequence (CDS) and protein, respectively, of *Vitis vinifera* (SEQ ID NOs: 103-104)

FIG. 12 shows the nucleotide and the predicted amino acid sequence of the homoserine kinase coding sequence (CDS) and protein, respectively, of *Cucumis sativus* (SEQ ID NOs: 105-106)

FIG. 13 shows the nucleotide and the predicted amino acid sequence of the homoserine kinase coding sequence (CDS) and protein, respectively, of *Spinacia oleracea* (SEQ ID NOs: 107-108)

FIG. 14 shows the nucleotide and the predicted amino acid sequence of the homoserine kinase coding sequence (CDS) and protein, respectively, of *Solanum lycopersicum* (SEQ ID NOs: 109-110)

DETAILED DESCRIPTION

This invention is based on research performed on resistance to *Hyaloperonospora parasitica* in *Arabidopsis* but is a general concept that can be more generally applied in plants, in particular in crop plants that are susceptible to infections with pathogens, such as Oomycota.

The invention is suitable for a large number of plant diseases caused by oomycetes such as, but not limited to, *Bremia lactucae* on lettuce, *Peronospora farinosa* on spinach, *Pseudoperonospora cubensis* on members of the Cucurbitaceae family, e.g. cucumber, *Peronospora destructor* on onion, *Hyaloperonospora parasitica* on members of the Brasicaceae family, e.g. cabbage, *Plasmopara viticola* on grape, *Phytophthora infestans* on tomato and potato, and *Phytophthora sojae* on soybean.

The homoserine level in these other plants can be increased with all techniques described above. However, when the modification of the HSK gene expression in a plant is to be achieved via genetic modification of the HSK gene or via the identification of mutations in the HSK gene, and the gene is not yet known it must first be identified. To generate pathogen-resistant plants, in particular crop plants, via genetic modification of the HSK gene or via the identification of mutations in the HSK gene, the orthologous HSK genes must be isolated from these plant species. Orthologs are defined as the genes or proteins from other organisms that have the same function.

Various methods are available for the identification of orthologous sequences in other plants.

A method for the identification of HSK orthologous sequences in a plant species, may for example comprise identification of homoserine kinase ESTs of the plant species in a database; designing primers for amplification of the complete homoserine kinase transcript or cDNA; performing amplification experiments with the primers to obtain the corresponding complete transcript or cDNA; and determining the nucleotide sequence of the transcript or cDNA.

Suitable methods for amplifying the complete transcript or cDNA in situations where only part of the coding sequence is known are the advanced PCR techniques 5'RACE, 3'RACE, TAIL-PCR, RLM-RACE and vectorette PCR.

Alternatively, if no nucleotide sequences are available for the plant species of interest, primers are designed on the HSK gene of a plant species closely related to the plant of interest, based on conserved domains as determined by multiple nucleotide sequence alignment, and used to PCR amplify the orthologous sequence. Such primers are suitably degenerate primers.

Another reliable method to assess a given sequence as being a HSK ortholog is by identification of the reciprocal best hit. A candidate orthologous HSK sequence of a given plant species is identified as the best hit from DNA databases when searching with the *Arabidopsis* HSK protein or DNA sequence, or that of another plant species, using a Blast programme. The obtained candidate orthologous nucleotide sequence of the given plant species is used to search for homology to all *Arabidopsis* proteins present in the DNA databases (e.g. at NCBI or TAIR) using the BlastX search method. If the best hit and score is to the *Arabidopsis* HSK protein, the given DNA sequence can be described as being n ortholog, or orthologous sequence.

HSK is encoded by a single gene in *Arabidopsis* and rice as deduced from the complete genome sequences that are publicly available for these plant species. In most other plant species tested so far, HSK appears to be encoded by a single gene, as determined by the analysis of mRNA sequences and EST data from public DNA databases, except for potato, tobacco and poplar for which two HSK homologs have been identified. The orthologous genes and proteins are identified in these plants by nucleotide and amino acid comparisons with the information that is present in public databases.

Alternatively, if no DNA sequences are available for the desired plant species, orthologous sequences are isolated by heterologous hybridization using DNA probes of the HSK gene of *Arabidopsis* or another plant or by PCR methods, making use of conserved domains in the HSK coding sequence to define the primers. For many crop species, partial HSK mRNA sequences are available that can be used to design primers to subsequently PCR amplify the complete mRNA or genomic sequences for DNA sequence analysis.

In a specific embodiment the ortholog is a gene of which the encoded protein shows at least 50% identity with the *Arabidopsis* HSK protein or that of other plant HSK proteins. In a more specific embodiment the homology is at least 55%, more specifically at least 60%, even more specifically at least 65%, at least 70%, at least 75%, at least 80%, at least 85%, at least 90%, at least 95% or at least 99%.

After orthologous HSK sequences are identified, the complete nucleotide sequence of the regulatory and coding sequence of the gene is identified by standard molecular biological techniques. For this, genomic libraries of the plant species are screened by DNA hybridization or PCR with probes or primers derived from a known homoserine kinase gene, such as the above described probes and primers, to identify the genomic clones containing the HSK gene. Alternatively, advanced PCR methods, such as RNA Ligase Mediated RACE (RLM-RACE), can be used to directly amplify gene and cDNA sequences from genomic DNA or reverse-transcribed mRNA. DNA sequencing subsequently results in the characterization of the complete gene or coding sequence.

Once the DNA sequence of the gene is known this information is used to prepare the means to modulate the expression of the homoserine kinase gene in anyone of the ways described above.

More in particular, to achieve a reduced HSK activity the expression of the HSK gene can be down-regulated or the enzymatic activity of the HSK protein can be reduced by amino acid substitutions resulting from nucleotide changes in the HSK coding sequence.

In a particular embodiment of the invention, downregulation of HSK gene expression is achieved by gene-silencing using RNAi. For this, transgenic plants are generated expressing a HSK anti-sense construct, an optimized micro-RNA construct, an inverted repeat construct, or a combined sense-anti-sense construct, so as to generate dsRNA corresponding to HSK that leads to gene silencing.

In an alternative embodiment, one or more regulators of the HSK gene are downregulated (in case of transcriptional activators) by RNAi.

In another embodiment regulators are upregulated (in case of repressor proteins) by transgenic overexpression. Overexpression is achieved in a particular embodiment by expressing repressor proteins of the HSK gene from a strong promoter, e.g. the 35S promoter that is commonly used in plant biotechnology.

The downregulation of the HSK gene can also be achieved by mutagenesis of the regulatory elements in the promoter, terminator region, or potential introns. Mutations in the HSK coding sequence in many cases lead to amino acid substitutions or premature stop codons that negatively affect the expression or activity of the encoded HSK enzyme.

These and other mutations that affect expression of HSK are induced in plants by using mutagenic chemicals such as ethyl methane sulfonate (EMS), by irradiation of plant material with gamma rays or fast neutrons, or by other means. The resulting nucleotide changes are random, but in a large collection of mutagenized plants the mutations in the HSK gene can be readily identified by using the TILLING (Targeting Induced Local Lesions IN Genomes) method (McCallum et al. (2000) Targeted screening for induced mutations. Nat. Biotechnol. 18,455-457, and Henikoff et al. (2004) TILLING. Traditional mutagenesis meets functional genomics. Plant Physiol. 135, 630-636). The principle of this method is based on the PCR amplification of the gene of interest from genomic DNA of a large collection of mutagenized plants in the M2 generation. By DNA sequencing or by looking for point mutations using a single-strand specific nuclease, such as the CEL-I nuclease (Till et al. (2004) Mismatch cleavage by single-strand specific nucleases. Nucleic Acids Res. 32, 2632-2641) the individual plants that have a mutation in the gene of interest are identified.

By screening many plants, a large collection of mutant alleles is obtained, each giving a different effect on gene expression or enzyme activity. The gene expression or enzyme activity can be tested by analysis of HSK transcript levels (e.g. by RT-PCR), quantification of HSK protein levels with antibodies or by amino acid analysis, measuring homoserine accumulation as a result of reduced HSK activity. These methods are known to the person skilled in the art.

The skilled person can use the usual pathogen tests to see if the homoserine accumulation is sufficient to induce pathogen resistance.

Plants with the desired reduced HSK activity or expression are then back-crossed or crossed to other breeding lines to transfer only the desired new allele into the background of the crop wanted.

The invention further relates to mutated HSK genes encoding HSK proteins with a reduced enzymatic activity. In a particular embodiment, the invention relates to the dmr1 alleles dmr1-1, dmr1-2, dmr1-3, dmr1-4 and dmr1-S.

In another embodiment, the invention relates to mutated versions of the HSK genes of *Lactuca sativa, Vitis vinifera, Cucumis sativus, Spinacia oleracea* and *Solanum lycopersicum* as shown in FIGS. 10-14 (SEQ ID NOs: 101-110).

The present invention demonstrates that plants having an increased homoserine level show resistance to pathogens, in particular of oomycete origin. With this knowledge the skilled person can actively modify the HSK gene by means of mutagenesis or transgenic approaches, but also identify so far unknown natural variants in a given plant species that accumulate homoserine or that have variants of the HSK gene that lead to an increase in homoserine, and to use these natural variants according to the invention.

In the present application the terms "homoserine kinase" and "HSK" are used interchangeably.

The present invention is illustrated in the following examples that are not intended to limit the invention in any way. In the examples reference is made to the following figures.

EXAMPLES

Example 1

Characterization of the Gene Responsible for Pathogen Resistance in dmr Mutants

Van Damme et al., 2005, supra disclose four mutants, dmr1-1, dmr1-2, dmr1-3 and dmr1-4 that are resistant to *H. parasitica*. The level of resistance can be examined by counting conidiophores per seedling leaf seven day post inoculation with the *H. parasitica* Cala2 isolate (obtainable from Dr. E. Holub (Warwick HRT, Wellesbourne, UK or Dr. G. Van den Ackerveken, Department of Biology, University of Utrecht, Utrecht, NL). For the parental line, Ler eds 1-2 (Parker et al., 1996, Plant Cell 8:2033-2046), which is highly susceptible, the number of conidiophores is set at 100%. The reduction in conidiophore formation on the infected dmr1 mutants compared to seedlings of the parental line is shown in FIG. 2.

According to the invention, the gene responsible for resistance to *H. parasitica* in the dmr1 mutants of van Damme et al., 2005, supra has been cloned by a combination of mapping and sequencing of candidate genes.

DMR1 was isolated by map-based cloning. The dmr1 mutants were crossed to the FN2 Col-0 mutant to generate a mapping population. The FN2 mutant is susceptible to the *H. parasitica* isolate Cala2, due to a fast neutron mutation in the RPP2A gene (Sinapidou et al., 2004, Plant J. 38:898-909). All 5 dmr1 mutants carry single recessive mutations as the F1 plants were susceptible, and approximately a quarter of the F2 plants displayed *H. parasitica* resistance.

The DMR1 cloning procedure is illustrated in FIG. 3 and described in more detail below. The map location of the dmr1 locus was first determined by genotyping 48 resistant F2 plants to be located on the lower arm of chromosome 2. From an additional screen for new recombinants on 650 F2 plants ~90 F2 recombinant plants between two INDEL (insertion/deletion) markers on BAC T24112 at 7.2 Mb and BAC F5J6 at 7.56 Mb (according to the TIGR *Arabidopsis* genome release Version 5.0 of January 2004) were identified, which allowed to map the gene to a region containing a contig of 5 BACs.

The F2 plants were genotyped and the F3 generation was phenotyped in order to fine map the dmr1 locus. The dmr1 mutation could be mapped to a ~130 kb region (encompassing 3 overlapping BAC clones: F6P23, T23A1, and F5J6) between two INDEL markers located on BAC F6P23, at 7.42 Mb and F5J6 at 7.56 Mb (according to the TIGR *Arabidopsis* genome release Version 5.0 of January 2004). This resulted in an area of 30 putative gene candidates for the dmr1 locus, between the *Arabidopsis* genes with the TAIR codes AT2g17060 and AT2g17380. Additionally cleaved amplified polymorphic sequences (CAPS) markers were designed based on SNPs linked to genes AT2g17190, AT2g17200, AT2g17270, At2g17300, At2g17310 and At2g17360 genes.

Analyses of 5 remaining recombinants in this region with these CAPS marker data left 8 candidate genes, At2g17230 (NM_127277, GI:30679913), At2g17240 (N_127278, GI:30679916), At2g17250 (N_127279, GI:22325730), At2g17260 (NM_127280, GI:30679922), At2g17265 (NM_127281, GI:18398362), At2g17270 (NM_127282, GI:30679927), At2g17280 (NM_127283, GI:42569096), At2g17290 (N_127284, GI:30679934). Sequencing of all the 8 genes resulted in the finding of point mutations in the AT2g17265 coding gene in the five dmr1 alleles; dmr1-1, dmr1-2, dmr1-3, dmr1-4 and dmr1-5, clearly demonstrating that AT2g17265 is DMR1. FIG. 3 shows a scheme of dmr1 with point mutations of different alleles.

At2g17265 encodes the homoserine kinase (HSK) enzyme, so far the only *Arabidopsis* gene exhibiting this function.

In *Arabidopsis*, HSK is encoded by a single gene, At2g17265 (Lee & Leustek, 1999, Arch. Biochem. Biophys. 372: 135-142). HSK is the fourth enzyme in the aspartate pathway required for the biosynthesis of the amino acids methionine, threonine and isoleucine. HSK catalyzes the phosphorylation of homoserine to homoserine phosphate (FIG. 5).

Example 2

Amino Acid Analysis

Homoserine phosphate is an intermediate in the production of methionine, isoleucine and threonine in *Arabidopsis*. Since homoserine kinase has a key role in the production of amino acids, free amino acid levels were determined in the parental line Ler eds 1-2 and the four different dmr1 mutants. For this amino acids from total leaves were extracted with 80% methanol, followed by a second extraction with 20% methanol. The combined extracts were dried and dissolved in water. After addition of the internal standard, S-amino-ethyl-cysteine (SAEC) amino acids were detected by automated ion-exchange chromatography with post column ninhydrin derivatization on a JOEL AminoTac JLC-500/V (Tokyo, Japan).

Amino acid analysis of four different dmr1 mutants and the parental line, Ler eds 1-2 showed an accumulation of homoserine in the dmr1 mutants, whereas this intermediate amino acid was not detectable in the parental line Ler eds 1-2. There was no reduction in the level of methionine, isoleucine and threonine in the dmr1 mutants (Table 1).

TABLE 1

Concentration (in pmol/mg fresh weight) of homoserine, methionine, threonine and isoleucine in above-ground parts of 2-week old seedlings of the parental line Ler eds1-2 and the mutants dmr1-1, dmr1-2, dmr1-3 and dmr1-4.

|  | Homoserine | Methionine | Isoleucine | Threonine |
| --- | --- | --- | --- | --- |
| dmr1-1 | 964 | 29 | 12 | 264 |
| dmr1-2 | 7128 | 14 | 29 | 368 |
| dmr1-3 | 466 | 11 | 16 | 212 |
| dmr1-4 | 6597 | 11 | 32 | 597 |
| Ler eds 1-2 | 0 | 7 | 10 | 185 |

Due to the reduced activity of the HSK in the dmr1 mutants, homoserine accumulates. This effect could be further enhanced by a stronger influx of aspartate into the pathway leading to an even higher level of homoserine. The high concentration of the substrate homoserine would still allow sufficient phosphorylation by the mutated HSK so that the levels of methionine, isoleucine and threonine are not reduced in the dmr1 mutants and the parental line, Ler eds1-2 (Table 1).

Example 3

Pathogen Resistance is Achieved by Application of L-Homoserine

To test if the effect is specific for homoserine the stereoisomer D-homoserine was tested. Whole seedlings were infiltrated with water, 5 mM D-homoserine and 5 mM L-homoserine. Only treatment with the natural amino acid L-homoserine resulted in resistance to *H. parasitica*. Seedlings treated with water or D-homoserine did not show a large reduction in pathogen growth and were susceptible to *H. parasitica*. The infiltration was applied to two *Arabidopsis* accessions, Ler eds 1-2 and Ws eds 1-1, susceptible to Cala2 and Waco9, respectively. Conidiophore formation was determined as an indicator for *H. parsitica* susceptibility. Conidiophores were counted 5 days post inoculation with *H. parasitica* and 2 days post infiltration with water, D-homoserine or L-homoserine. (FIG. 6). L-homoserine infiltration clearly results in reduction of conidiophore formation and *H. parasitica* resistance. This was further confirmed by studying pathogen growth in planta by trypan blue staining of *Arabidopsis* seedlings. Plants were inoculated with isolate Cala2. Two days later the plants were treated by infiltration with water, 5 mM D-homoserine, and 5 mM L-homoserine. Symptoms were scored at 5 days post inoculation and clearly showed that only the L-homoserine-infiltrated seedlings showed a strongly reduced pathogen growth and no conidiophore formation (FIG. 7).

Microscopic analysis showed that only in L-homoserine treated leaves the haustoria, feeding structures that are made by *H. parasitica* during the infection process, are disturbed. Again it is shown that increased levels of homoserine in planta lead to pathogen resistance.

Example 4

Identification of HSK Orthologs in Crops

1. Screening of Libraries on the Basis of Sequence Homology

The nucleotide and amino acid sequences of the homoserine kinase gene and protein of *Arabidopsis thaliana* are shown in FIGS. 8 and 9 (SEQ ID NOs: 99-100).

Public libraries of nucleotide and amino acid sequences were compared with the sequences of FIGS. 8 and 9 (SEQ ID NOs: 99-100).

This comparison resulted in identification of the complete HSK coding sequences and predicted amino acid sequences in *Citrus sinensis*, *Populus trichocarpa* (1), *Populus tri-* chocarpa (2), *Solanum tuberosum* (2), *Solanum tuberosum* (1), *Nicotiana benthamiana, Ipomoea nil, Glycine max, Phaseolus vulgaris, Pinus taeda, Zea mays*, and *Oryza sativa*. The sequence information of the orthologous proteins thus identified is given in FIG. 1. For many other plant species orthologous DNA fragments could be identified by BlastX as reciprocal best hits to the *Arabidopsis* or other plant HSK protein sequences.

2. Identification of Orthologs by Means of Heterologous Hybridisation

The HSK DNA sequence of *Arabidopsis thaliana* as shown in FIG. 8 (SEQ ID NO: 99) is used as a probe to search for homologous sequences by hybridization to DNA on any plant species using standard molecular biological methods. Using this method orthologous genes are detected by southern hybridization on restriction enzyme-digested DNA or by hybridization to genomic or cDNA libraries. These techniques are well known to the person skilled in the art. As an alternative probe the HSK DNA sequence of any other more closely related plant species can be used as a probe.

3. Identification of Orthologs by Means of PCR

For many crop species, partial HSK mRNA or gene sequences are available that are used to design primers to subsequently PCR amplify the complete cDNA or genomic sequence. When 5' and 3' sequences are available the missing internal sequence is PCR amplified by a HSK specific 5' forward primer and 3' reverse primer. In cases where only 5', internal or 3' sequences are available, both forward and reverse primers are designed. In combination with available plasmid polylinker primers, inserts are amplified from genomic and cDNA libraries of the plant species of interest. In a similar way, missing 5' or 3' sequences are amplified by advanced PCR techniques; 5'RACE, 3' RACE, TAIL-PCR, RLM-RACE or vectorette PCR.

As an example the sequencing of the *Lactuca sativa* (lettuce) HSK cDNA is provided. From the Genbank EST database at NCBI several Lactuca HSK ESTs were identified using the tblastn tool starting with the *Arabidopsis* HSK amino acid sequence. Clustering and alignment of the ESTs resulted in a consensus sequence for a 5' HSK fragment and one for a 3' HSK fragment. To obtain the complete lettuce HSK cDNA the RLM-RACE kit (Ambion) was used on mRNA from lettuce seedlings. The 5' mRNA sequence was obtained by using a primer that was designed in the 3' HSK consensus sequence derived from ESTs (R1S1a: GCCTTCT-TCACAGCATCCATTCC—SEQ ID NO: 1) and the 5' RACE primers from the kit. The 3' cDNA sequence was obtained by using two primers designed on the 5'RACE fragment (Let3RACEOut: CCGTTGCGGTTAATGAGATT—SEQ ID NO: 2, and Let3RACEInn: TCGTGTTGGTGAATCCT-GAA—SEQ ID NO: 3) and the 3' RACE primers from the kit. Based on the assembled sequence new primers were designed to amplify the complete HSK coding from cDNA to provide the nucleotide sequence and derived protein sequence as presented in FIG. 10 (SEQ ID NOs: 101-102). A similar approach was a used for *Solanum lycopersicum* (FIG. 14—SEQ ID NOs: 109-110) and *Vitis vinifera* (FIG. 11—SEQ ID NOs: 103-104).

The complete HSK coding sequences from more than 10 different plants species have been identified from genomic and EST databases. From the alignment of the DNA sequences, conserved regions in the coding sequence were selected for the design of degenerate oligonucleotide primers (for the degenerate nucleotides the abbreviations are according to the IUB nucleotide symbols that are standard codes used by all companies synthesizing oligonucleotides; G=Guanine, A=Adenine, T=Thymine, C=Cytosine, R=A or G, Y=C or T, M=A or C, K=G or T, S=C or G, W=A or T, B=C or G or T, D=G or A or T, H=A or C or T, V=A or C or G, N=A or C or G or T).

The procedure for obtaining internal HSK cDNA sequences of a given plant species is as follows:

1. mRNA is isolated using standard methods,
2. cDNA is synthesized using an oligo dT primer and standard methods,
3. using degenerate forward and reverse oligonucleotides a PCR reaction is carried out,
4. PCR fragments are separated by standard agarose gel electrophoresis and fragments of the expected size are isolated from the gel,
5. isolated PCR fragments are cloned in a plasmid vector using standard methods,
6. plasmids with correct insert sizes, as determined by PCR, are analyzed by DNA sequencing,
7. Sequence analysis using blastX reveals which fragments contain the correct internal HSK sequences,
8. The internal DNA sequence can then be used to design gene- and species-specific primers for 5' and 3' RACE to obtain the complete HSK coding sequence by RLM-RACE (as described above).

As an example the sequencing of the *Cucumis sativus* (cucumber) HSK cDNA is provided. For cucumber two primer combinations were successful in amplifying a stretch of internal coding sequence from cDNA; combination 1: primer F1Kom (GAYTTCYTHGGMTGYGCCGT—SEQ ID NO: 4) and M1RC (GCRGCGATKCCRGCRCAGTT—SEQ ID NO: 5), and combination 2: primer M1Kom (AACT-GYGCYGGMATCGCYGC—SEQ ID NO: 6) and R1Kom (CCATDCCVGGAATCAANGGVGC—SEQ ID NO: 7). After cloning and sequencing of the amplified fragments cucumber HSK-specific primers were designed for 5' RACE (Cuc5RACEOut: AGAGGATTTTTACTAAGTTTAT-TCGTG—SEQ ID NO: 8 and Cuc5RACEInn: AGACAT-AATCTCCAAGCCATCA—SEQ ID NO: 9) and 3' RACE (Cuc3RACEOut: TGATGGCTTGGGAGATTATGTCT—SEQ ID NO: 10 and Cuc3RACETnn: CACGAATAAACT-TAGTAAAAATCCTCT—SEQ ID NO: 11). Finally the complete cucumber HSK cDNA sequence was amplified and sequenced (FIG. 12—SEQ ID NOs: 105-106). A similar approach was a used for spinach, *Spinacia oleracea* (FIG. 13—SEQ ID NOs: 107-108).

Orthologs identified as described in this example can be modified using well-known techniques to induce mutations that reduce the HSK expression or activity. Alternatively, the genetic information of the orthologs can be used to design vehicles for gene silencing. All these sequences are then used to transform the corresponding crop plants to obtain plants that are resistant to Oomycota.

Example 5

Reduction of Homoserine Kinase Expression in *Arabidopsis* by Means of RNAi

The production of HSK silenced lines has been achieved in *Arabidopsis* by RNAi. A construct containing two ~750 bp fragments of the HSK exon in opposite directions was successfully transformed into the *Arabidopsis* Col-0 accession. The transformants were analysed for resistance to *H. parasitica*, isolate Waco9. Several transgenic lines were obtained that confer resistance to *H. parasitica*. Analysis of HSK expression and homoserine accumulation confirm that in the transformed lines the HSK gene is silenced, resulting in resistance to *H. parasitica*.

Example 6

Mutation of Seeds

Seeds of the plant species of interest are treated with a mutagen in order to introduce random point mutations in the genome. Mutated plants are grown to produce seeds and the next generation is screened for increased accumulation of homoserine. This is achieved by measuring levels of the amino acid homoserine, by monitoring the level of HSK gene expression, or by searching for missense mutations in the HSK gene by the TILLING method, by DNA sequencing, or by any other method to identify nucleotide changes.

The selected plants are homozygous or are made homozygous by selfing or inter-crossing. The selected homozygous plants with increased homoserine levels are tested for increased resistance to the pathogen of interest to confirm the increased disease resistance.

Example 7

Transfer of a Mutated Allele into the Background of a Desired Crop

Introgression of the desired mutant allele into a crop is achieved by crossing and genotypic screening of the mutant allele. This is a standard procedure in current-day marker assistant breeding of crops.

Tables

TABLE 2

GI numbers (GenInfo identifier) and Genbank accession number for Expressed Sequence Tags (ESTs) and mRNA sequences of the *Arabidopsis* HSK mRNA and orthologous sequences from other plant species.

A GI number (genInfo identifier, sometimes written in lower case, "gi") is a unique integer which identifies a particular sequence. The GI number is a series of digits that are assigned consecutively to each sequence record processed by NCBI. The GI number will thus change every time the sequence changes. The NCBI assigns GI numbers to all sequences processed into Entrez, including nucleotide sequences from DDBJ/EMBL/GenBank, protein sequences from SWISS-PROT, PIR and many others. The GI number thus provides a unique sequence identifier which is independent of the database source that specifies an exact sequence. If a sequence in GenBank is modified, even by a single base pair, a new GI number is assigned to the updated sequence. The accession number stays the same. The GI number is always stable and retrievable. Thus, the reference to GI numbers in the table provides a clear and unambiguous identification of the corresponding sequence.

| Species | Common name | Detail | GI number | Genbank |
|---|---|---|---|---|
| *Arabidopsis thaliana* | Thale cress | mRNA | 39104571 | AK117871 |
| *Citrus sinensis* | Sweet Orange | ESTs | 55935768 | CV886642 |
| | | | 28618675 | CB293218 |
| | | | 55935770 | CV886643 |
| | | | 28619455 | CB293998 |
| *Glycine max* | Soybean | ESTs | 10846810 | BF069552 |
| | | | 17401269 | BM178051 |
| | | | 8283472 | BE021031 |
| | | | 16348965 | BI974560 |
| | | | 7285286 | AW597773 |
| | | | 58024665 | CX711406 |
| | | | 58017647 | CX704389 |
| | | | 20449357 | BQ253481 |
| | | | 16105339 | BI893079 |
| | | | 37996979 | CF808568 |
| | | | 37996460 | CF808049 |

TABLE 2-continued

GI numbers (GenInfo identifier) and Genbank accession number for Expressed Sequence Tags (ESTs) and mRNA sequences of the *Arabidopsis* HSK mRNA and orthologous sequences from other plant species.

A GI number (genInfo identifier, sometimes written in lower case, "gi") is a unique integer which identifies a particular sequence. The GI number is a series of digits that are assigned consecutively to each sequence record processed by NCBI. The GI number will thus change every time the sequence changes. The NCBI assigns GI numbers to all sequences processed into Entrez, including nucleotide sequences from DDBJ/EMBL/GenBank, protein sequences from SWISS-PROT, PIR and many others. The GI number thus provides a unique sequence identifier which is independent of the database source that specifies an exact sequence. If a sequence in GenBank is modified, even by a single base pair, a new GI number is assigned to the updated sequence. The accession number stays the same. The GI number is always stable and retrievable. Thus, the reference to GI numbers in the table provides a clear and unambiguous identification of the corresponding sequence.

| Species | Common name | Detail | GI number | Genbank |
|---|---|---|---|---|
| | | | 6072786 | AW102173 |
| | | | 26057235 | CA800149 |
| | | | 6455775 | AW186458 |
| | | | 6072724 | AW102111 |
| | | | 9203587 | BE329811 |
| *Ipomoea nil* | Japanese morning glory | ESTs | 74407098 | CJ761918 |
| | | | 74402449 | CJ757269 |
| | | | 74402115 | CJ756935 |
| | | | 74388670 | CJ743490 |
| *Nicotiana Benthamiana* | Tobacco | ESTs | 39880685 | CK295868 |
| | | | 39859026 | CK284950 |
| | | | 39864851 | CK287885 |
| | | | 39864855 | CK287887 |
| | | | 39859024 | CK284949 |
| | | | 39864853 | CK287886 |
| | | | 39880683 | CK295867 |
| | | | 39864849 | CK287884 |
| *Oryza sativa* | Rice | mRNA | 50916171 | XM_468550 |
| | | | 32970537 | AK060519 |
| *Phaseolus vulgaris* | Common Bean | ESTs | 62708660 | CV535256 |
| | | | 62710636 | CV537232 |
| | | | 62708052 | CV534648 |
| | | | 62709395 | CV535991 |
| | | | 62710761 | CV537357 |
| | | | 62708535 | CV535131 |
| | | | 62708534 | CV535130 |
| | | | 62711318 | CV537914 |
| | | | 62707924 | CV534520 |
| | | | 62710733 | CV537329 |
| | | | 62709601 | CV536197 |
| | | | 62709064 | CV535660 |
| | | | 62708834 | CV535430 |
| *Pinus taeda* | Loblolly Pine | ESTs | 70780626 | DR690274 |
| | | | 67490638 | DR092267 |
| | | | 48933532 | CO162991 |
| | | | 34354980 | CF396563 |
| | | | 67706241 | DR117931 |
| | | | 17243465 | BM158115 |
| | | | 34349136 | CF390719 |
| | | | 66981484 | DR057917 |
| | | | 48932595 | CO162054 |
| | | | 66689208 | DR011702 |
| | | | 48933450 | CO162909 |
| | | | 34350236 | CF391819 |
| | | | 67706323 | DR118013 |
| | | | 48932678 | CO162137 |
| | | | 66981399 | DR057832 |
| | | | 34354850 | CF396433 |
| *Populus trichocarpa* 1 | Poplar | Genome v1.0, LG_IX, 149339-148242 Expression confirmed by ESTs | | |
| *Populus trichocarpa* 2 | Poplar | Genome v1.0, scaffold_66, 1415935-1417032 Expression confirmed by ESTs | | |
| *Solanum tuberosum* 1 | Potato | ESTs | 66838966 | DR037071 |
| | | | 61238361 | DN588007 |
| | | | 39804315 | CK251362 |
| | | | 39801776 | CK250065 |

TABLE 2-continued

GI numbers (GenInfo identifier) and Genbank accession number for Expressed Sequence Tags (ESTs) and mRNA sequences of the *Arabidopsis* HSK mRNA and orthologous sequences from other plant species.
A GI number (genInfo identifier, sometimes written in lower case, "gi") is a unique integer which identifies a particular sequence. The GI number is a series of digits that are assigned consecutively to each sequence record processed by NCBI. The GI number will thus change every time the sequence changes. The NCBI assigns GI numbers to all sequences processed into Entrez, including nucleotide sequences from DDBJ/EMBL/GenBank, protein sequences from SWISS-PROT, PIR and many others. The GI number thus provides a unique sequence identifier which is independent of the database source that specifies an exact sequence. If a sequence in GenBank is modified, even by a single base pair, a new GI number is assigned to the updated sequence. The accession number stays the same. The GI number is always stable and retrievable. Thus, the reference to GI numbers in the table provides a clear and unambiguous identification of the corresponding sequence.

| Species | Common name | Detail | GI number | Genbank |
|---|---|---|---|---|
| | | | 9250052 | BE340521 |
| | | | 39832341 | CK275363 |
| | | | 21917848 | BQ116921 |
| | | | 9249876 | BE340345 |
| | | | 39815050 | CK258070 |
| | | | 39804985 | CK251702 |
| | | | 39804987 | CK251703 |
| | | | 39825384 | CK268406 |
| | | | 39832342 | CK275364 |
| | | | 66838967 | DR037072 |
| | | | 9250394 | BE340863 |
| | | | 39804317 | CK251363 |
| | | | 39825385 | CK268407 |
| | | | 21375072 | BQ516203 |
| *Solanum tuberosum 2* | Potato | ESTs | 39813353 | CK256373 |
| | | | 39793361 | CK246131 |
| | | | 39793359 | CK246130 |
| | | | 39813352 | CK256372 |
| *Zea Mays* | Maize | ESTs | 76021237 | DT948407 |
| | | | 76913306 | DV165065 |
| | | | 71446162 | DR827212 |
| | | | 71449720 | DR830770 |
| | | | 78117576 | DV535963 |
| | | | 91048486 | EB158904 |
| | | | 71439095 | DR820145 |
| | | | 76936546 | DV174774 |
| | | | 76012246 | DT939416 |
| | | | 78085419 | DV513812 |
| | | | 71766843 | DR964780 |
| | | | 76924795 | DV170131 |
| | | | 71449067 | DR830117 |
| | | | 91875652 | EB405609 |
| | | | 71450175 | DR831225 |
| | | | 78103551 | DV521979 |
| | | | 78090555 | DV518929 |
| | | | 78104654 | DV523072 |
| | | | 76926251 | DV170768 |
| | | | 78111568 | DV529965 |
| | | | 71773353 | DR971257 |
| | | | 71425952 | DR807002 |
| | | | 93282458 | EB674722 |
| | | | 78074199 | DV502633 |
| | | | 76293328 | DV032896 |
| | | | 78075462 | DV503896 |
| | | | 91054750 | EB165168 |
| | | | 86469295 | DY235665 |
| | | | 74243218 | DT651132 |
| | | | 74242899 | DT650813 |
| | | | 101384764 | EB814428 |
| | | | 91054750 | EB165168 |
| | | | 71440426 | DR821476 |
| | | | 78121780 | DV540164 |
| | | | 78103550 | DV521978 |
| | | | 86469294 | DY235664 |
| | | | 91877777 | EB407734 |
| | | | 67014441 | CO443190 |
| | | | 76924794 | DV170130 |
| | | | 76021236 | DT948406 |
| | | | 71446161 | DR827211 |
| | | | 78110960 | DV529358 |
| | | | 78074736 | DV503170 |
| | | | 71428043 | DR809093 |
| | | | 86469052 | DY235422 |
| | | | 71440425 | DR821475 |
| | | | 78121779 | DV540163 |
| | | | 78104653 | DV523071 |
| | | | 37400920 | CF637820 |
| | | | 78074198 | DV502632 |
| | | | 71449719 | DR830769 |
| *Solanum lycopersicum* | Tomato | | 58213736 | BP877213 |
| | | | 7333245 | AW621598 |
| | | | 4386685 | AI482761 |
| Unigene SGN-U223239 from Sol Genomics Network | | | Sequence described in this patent application | |
| *Lactuca sativa* | Lettuce | | Sequence described in this patent application | |
| *Vitis vinifera* | Grape vine | | Sequence described in this patent application | |
| *Spinacia oleracea* | Spinach | | Sequence described in this patent application | |
| *Cucumis sativus* | Cucumber | | Sequence described in this patent application | |

TABLE 3

Primer sequences of insertion/deletion (INDEL, size difference indicated in brackets) markers and cleaved amplified polymorphics sequences (CAP, polymorphic restriction site indicated in brackets) used in the mapping of the DMR1 locus.

| Primer name: BAC and/or TAIR At code | Forward primer sequence | SEQ ID NO: | Reverse primer sequence | SEQ ID NO: | TYPE (size/enzyme) | GI number of TAIR At code |
|---|---|---|---|---|---|---|
| T24112 | AATCCAAATTTCTT | 12 | AAACGAAGAGTGAC | 13 | INDEL | 18398180 |
| (At2g16670) | GCGAGAACACA | 14 | AATGGTTGGAG | 15 | (33) | |

TABLE 3-continued

Primer sequences of insertion/deletion (INDEL, size difference indicated in brackets) markers and cleaved amplified polymorphics sequences (CAP, polymorphic restriction site indicated in brackets) used in the mapping of the DMR1 locus.

| Primer name: BAC and/or TAIR At code | Forward primer sequence | SEQ ID NO: | Reverse primer sequence | SEQ ID NO: | TYPE (size/enzyme) | GI number of TAIR At code |
|---|---|---|---|---|---|---|
| F5J6 | CCGTCAGATCAGTC | 16 | CAGAAGCTGATGAT | 17 | INDEL | 23506018 |
| (AT2g17370-80) | CTCATCTTGTT | 18 | CGTGGAAAGTA | 19 | (30) | 30679966 |
| F6P23 | CGGTTTCATGTCGA | 20 | AAGAAGAGAACTGC | 21 | INDEL | 22325728 |
| (AT2g17060) | GGAAGATCATA | 22 | GTCAACCTTCC | 23 | (37) | |
| T23A1 | TCCTTCCATGTCCG | 24 | AACAAATTTGCTTC | 25 | INDEL | 42570808 |
| (AT2g17220-30) | AAACCA | 26 | CAGCCTTT | 27 | (26) | |
| AT2g17190 | GAATAGAGGTTGAT | 28 | CTCTTGTATGTTTT | 29 | CAP | 30679898 |
| | GGAAATCAAGA | 30 | ACTGGGCTGAT | 31 | (MseI) | |
| AT2g17200 | CCTCTCCACCCATT | 32 | CGATCCATTTCGTC | 33 | CAP | 30679902 |
| | TCTAATTTCG | 34 | AAGCAATCTAC | 35 | (MboII) | |
| AT2g17270 | GATGCAGCTAAATT | 36 | ACGAAAATATCAAA | 37 | CAP | 30679927 |
| | ATCAGTGTGAA | 38 | AAGCTCCTTC | 39 | (NlaIII) | |
| AT2g17300-05 | AGGTAGGATGGTAT | 40 | GCATGTTTTCTCTA | 41 | CAP | 30679937 |
| | TATGTTTGAACT | 42 | AGCGATAGAAG | 43 | (EcoRI) | 22325732 |
| AT2g17310 | ATGGGTAACGAAAG | 44 | CACATGTATAAGGT | 45 | CAP | 42569097 |
| | AGAGGATTAGT | 46 | CTTCCCATAGA | 47 | (MseI) | |
| AT2g17360 | CCAACAAGTATCCT | 48 | CCACATCAAACTTA | 49 | CAP | 30679959 |
| | CTTTTGTTGTT | 50 | ATGAACTCCAC | 51 | (MaeIII) | |

TABLE 4

Primer sequences used for amplifying and sequencing of eight candidate DMR1 genes for which the TAIR and GI codes are indicated

| Primer name | Primer sequence | SEQ ID NO: | TAIR codes | GI codes |
|---|---|---|---|---|
| MvD17230_F | TTCCCGAAGTGTACATTAAAAGCTC | 52 | At2g17230 | 30679913 |
| MvD17230_R | TATGTCATCCCCAAGAGAAGAAGAC | 53 | At2g17230 | 30679913 |
| MvD17240-F | CAATAAAAGCCTTTAAAAGCCCACT | 54 | At2g17240 | 30679916 |
| MvD17240_R | TAGCTTCTGAAACTGTGGCATTACA | 55 | At2g17240 | 30679916 |
| MvD17250_1F | CATGATTTGAGGGGTATATCCAAAA | 56 | At2g17250 | 22325730 |
| MvD17250_1R | GGAGGTGGGATTTGAGATAAAACTT | 57 | At2g17250 | 22325730 |
| MvD17250_2F | TAGCCTAGAACTCTCTGTTCGCAAG | 58 | At2g17250 | 22325730 |
| MvD17250_2R | CATTATTTTGCGTAGTTGTGAGTGG | 59 | At2g17250 | 22325730 |
| MvD17250_3F | CGAAGAAATCCTACAATCAACCATC | 60 | At2g17250 | 22325730 |
| MvD17250_3R | TCTCACAATTCCCATCTCTTACTCC | 61 | At2g17250 | 22325730 |
| MvD17260_1F | TTACTCATTTGGGTGAACAGAACAA | 62 | At2g17260 | 30679922 |
| MvD17260_1R | ATCATCCCTAATCTCTCTGCTTCCT | 63 | At2g17260 | 30679922 |
| MvD17260_2F | GATTAAGATACGGGGAATGGAGTCT | 64 | At2g17260 | 30679922 |

TABLE 4-continued

Primer sequences used for amplifying and sequencing of eight candidate
DMR1 genes for which the TAIR and GI codes are indicated

| Primer name | Primer sequence | SEQ ID NO: | TAIR codes | GI codes |
|---|---|---|---|---|
| MvD17260_2R | ATGCAGACAAATAAGATGGCTCTTG | 65 | At2g17260 | 30679922 |
| MvD17260_3F | GTTGTTGCTCCTGTCACAAGACTTA | 66 | At2g17260 | 30679922 |
| MvD17260_3R | GAACAAAGACGAAGCCTTTAAACAA | 67 | At2g17260 | 30679922 |
| MvD17265_F | GAGGACTGCATCTAGAAGACCCATA | 68 | At2g17265 | 18398362 |
| MvD17265_R | TGGGCTCTCAACTATAAAGTTTGCT | 69 | At2g17265 | 18398362 |
| MvD17270_F1 | TAACGGTAAAGCAACGAATCTATCC | 70 | At2g17270 | 30679927 |
| MvD17270_R1 | TCAAACTGATAACGAGAGACGTTGA | 71 | At2g17270 | 30679927 |
| MvD17270_F2 | TTGCGTTCGTTTTTGAGTCTTTTAT | 72 | At2g17270 | 30679927 |
| MvD17270_R2 | AAACCAGACTCATTCCTTTGACATC | 73 | At2g17270 | 30679927 |
| MvD17280_F1 | TTTAGGATCTCTGCCTTTTCTCAAC | 74 | At2g17280 | 42569096 |
| MvD17280_R1 | GAGAAATCAATAGCGGGAAAGAGAG | 75 | At2g17280 | 42569096 |
| MvD17280_F2 | GCTTAAATAGTCCTCCTTTCCTTGC | 76 | At2g17280 | 42569096 |
| MvD17280_R2 | TCTGCTGGTTCTCATGTTGATAGAG | 77 | At2g17280 | 42569096 |
| MvD17290_F1 | CTCTCCTTCATCATTTCACAAATCC | 78 | At2g17290 | 30679934 |
| MvD17290_R1 | TTCCTCTCGCTGTAATGACCTCTAT | 79 | At2g17290 | 30679934 |
| MvD17290_F2 | TGCCACAGGTGTTGACTATGC | 80 | At2g17290 | 30679934 |
| MvD17290_R2 | TGCTCTTAAACCCGCAATCTC | 81 | At2g17290 | 30679934 |
| MvD17290_F3 | GAAGATGGCTTTAAAGGTCAGTTTGT | 82 | At2g17290 | 30679934 |
| MvD17290_R3 | AGCAACAACAACTAAAAGGTGGAAG | 83 | At2g17290 | 30679934 |

---

The invention claimed is:

1. An isolated plant which is resistant to a pathogen, wherein the plant has an increased endogenous L-homoserine level as compared to a plant that is not resistant to said pathogen, wherein said plant is selected from the group consisting of potato, soybean, rice, and maize, and
   wherein when said plant is potato and said pathogen is *Phytophthora infestans*, said potato plant has a mutation in its homoserine kinase gene lowering the homoserine kinase activity of SEQ ID NO: 87 or SEQ ID NO: 90;
   wherein when said plant is soybean and said pathogen is *Phytophthora sojae*, said soybean plant has a mutation in its homoserine kinase gene lowering the homoserine kinase activity of SEQ ID NO: 94;
   wherein when said plant is rice and said pathogen is *Sclerospora*, said rice plant has a mutation in its homoserine kinase gene lowering the homoserine kinase activity of SEQ ID NO: 98; and
   wherein when said plant is maize and said pathogen is *Peronosclerospora*, said maize plant has a mutation in its homoserine kinase gene lowering the homoserine kinase activity of SEQ ID NO: 97.

2. The plant of claim 1, wherein the mutation in the homoserine kinase gene leads to an amino acid substitution in the encoded protein.

3. A method for obtaining a plant which is resistant to a pathogen, wherein the plant has an increased endogenous L-homoserine level as compared to a plant that is not resistant to said pathogen, wherein said plant is selected from the group consisting of potato, soybean, rice and maize, the method comprising:

increasing the endogenous L-homoserine level in a potato plant by a mutation in its homoserine kinase gene, thus lowering the homoserine kinase activity of SEQ ID NO: 87 or SEQ ID NO: 90 to produce a potato plant which is resistant to *Phytophthora infestans*; or
   increasing the endogenous L-homoserine level in a soybean plant by a mutation in its homoserine kinase gene, thus lowering the homoserine kinase activity of SEQ ID NO: 94 to produce a soybean plant which is resistant to *Phytophthora sojae*; or
   increasing the endogenous L-homoserine level in a rice plant by a mutation in its homoserine kinase gene, thus lowering the homoserine kinase activity of SEQ ID NO: 98 to produce a rice plant which is resistant to *Sclerospora*; or
   increasing the endogenous L-homoserine level in a maize plant by a mutation in its homoserine kinase gene, thus lowering the homoserine kinase activity of SEQ ID NO: 97 to produce a maize plant which is resistant to *Peronosclerospora*.

4. The method of claim 3, wherein the mutation results in one or more amino acid changes that lead to a lower homoserine kinase activity.

5. The method of claim 3, wherein the mutation is effected by mutagenic treatment of the potato plant, soybean plant, rice plant, or maize plant.

6. The method of claim 5, wherein the mutagenic treatment is effected with a mutagen or radiation.

\* \* \* \* \*

UNITED STATES PATENT AND TRADEMARK OFFICE
CERTIFICATE OF CORRECTION

PATENT NO. : 8,796,511 B2  Page 1 of 1
APPLICATION NO. : 13/969951
DATED : August 5, 2014
INVENTOR(S) : Augustinus Franciscus J. M. Van Den Ackerveken It is certified that error appears in the above-identified patent and that said Letters Patent is hereby corrected as shown below:

Title Page, Column 1, Item (62) Related U.S. Application Data, line 7, please insert
-- PCT/EP2005/011718 11/01/2005 --

Signed and Sealed this
Sixth Day of January, 2015

Michelle K. Lee
*Deputy Director of the United States Patent and Trademark Office*

SEQUENCE LISTING

<160> NUMBER OF SEQ ID NOS: 110

<210> SEQ ID NO 1
<211> LENGTH: 23
<212> TYPE: DNA
<213> ORGANISM: Lactuca sativa

<400> SEQUENCE: 1
gccttcttca cagcatccat tcc                                           23

<210> SEQ ID NO 2
<211> LENGTH: 20
<212> TYPE: DNA
<213> ORGANISM: Lactuca sativa

<400> SEQUENCE: 2
ccgttgcggt taatgagatt                                               20

<210> SEQ ID NO 3
<211> LENGTH: 20
<212> TYPE: DNA
<213> ORGANISM: Lactuca sativa

<400> SEQUENCE: 3
tcgtgttggt gaatcctgaa                                               20

```
<210> SEQ ID NO 4
<211> LENGTH: 20
<212> TYPE: DNA
<213> ORGANISM: Cucumis sativus

<400> SEQUENCE: 4
gayttcythg gmtgygccgt                                                   20

<210> SEQ ID NO 5
<211> LENGTH: 20
<212> TYPE: DNA
<213> ORGANISM: Cucumis sativus

<400> SEQUENCE: 5
gcrgcgatkc crgcrcagtt                                                   20

<210> SEQ ID NO 6
<211> LENGTH: 20
<212> TYPE: DNA
<213> ORGANISM: Cucumis sativus

<400> SEQUENCE: 6
aactgygcyg gmatcgcygc                                                   20

<210> SEQ ID NO 7
<211> LENGTH: 22
<212> TYPE: DNA
<213> ORGANISM: Cucumis sativus
<220> FEATURE:
<221> NAME/KEY: misc_feature
<222> LOCATION: (17)..(17)
<223> OTHER INFORMATION: n is a, c, g, or t

<400> SEQUENCE: 7
ccatdccvgg aatcaanggv gc                                                22

<210> SEQ ID NO 8
<211> LENGTH: 27
<212> TYPE: DNA
<213> ORGANISM: Cucumis sativus

<400> SEQUENCE: 8
agaggatttt tactaagttt attcgtg                                           27

<210> SEQ ID NO 9
<211> LENGTH: 23
<212> TYPE: DNA
<213> ORGANISM: Cucumis sativus

<400> SEQUENCE: 9
agacataatc tcccaagcca tca                                               23

<210> SEQ ID NO 10
<211> LENGTH: 23
<212> TYPE: DNA
<213> ORGANISM: Cucumis sativus

<400> SEQUENCE: 10
tgatggcttg ggagattatg tct                                               23

<210> SEQ ID NO 11
<211> LENGTH: 27
<212> TYPE: DNA
```

<213> ORGANISM: Cucumis sativus

<400> SEQUENCE: 11
cacgaataaa cttagtaaaa atcctct        27

<210> SEQ ID NO 12
<211> LENGTH: 14
<212> TYPE: DNA
<213> ORGANISM: Artificial
<220> FEATURE:
<223> OTHER INFORMATION: Fw primer T24I12

<400> SEQUENCE: 12
aatccaaatt tctt        14

<210> SEQ ID NO 13
<211> LENGTH: 14
<212> TYPE: DNA
<213> ORGANISM: Artificial
<220> FEATURE:
<223> OTHER INFORMATION: Bw primer T24I12

<400> SEQUENCE: 13
aaacgaagag tgac        14

<210> SEQ ID NO 14
<211> LENGTH: 11
<212> TYPE: DNA
<213> ORGANISM: Artificial
<220> FEATURE:
<223> OTHER INFORMATION: Fw primer At2g16670

<400> SEQUENCE: 14
gcgagaacac a        11

<210> SEQ ID NO 15
<211> LENGTH: 11
<212> TYPE: DNA
<213> ORGANISM: Artificial
<220> FEATURE:
<223> OTHER INFORMATION: BW primer At2g16670

<400> SEQUENCE: 15
aatggttgga g        11

<210> SEQ ID NO 16
<211> LENGTH: 14
<212> TYPE: DNA
<213> ORGANISM: Artificial
<220> FEATURE:
<223> OTHER INFORMATION: Fw primer F5J6

<400> SEQUENCE: 16
ccgtcagatc agtc        14

<210> SEQ ID NO 17
<211> LENGTH: 14
<212> TYPE: DNA
<213> ORGANISM: Artificial
<220> FEATURE:
<223> OTHER INFORMATION: Bw primer F5J6

<400> SEQUENCE: 17
cagaagctga tgat        14

```
<210> SEQ ID NO 18
<211> LENGTH: 11
<212> TYPE: DNA
<213> ORGANISM: Artificial
<220> FEATURE:
<223> OTHER INFORMATION: Fw primer AT2g17370-80

<400> SEQUENCE: 18
ctcatcttgt t                                                          11

<210> SEQ ID NO 19
<211> LENGTH: 11
<212> TYPE: DNA
<213> ORGANISM: Artificial
<220> FEATURE:
<223> OTHER INFORMATION: Bw primer AT2g17370-80

<400> SEQUENCE: 19
cgtggaaagt a                                                          11

<210> SEQ ID NO 20
<211> LENGTH: 14
<212> TYPE: DNA
<213> ORGANISM: Artificial
<220> FEATURE:
<223> OTHER INFORMATION: Fw primer F6P23

<400> SEQUENCE: 20
cggtttcatg tcga                                                       14

<210> SEQ ID NO 21
<211> LENGTH: 14
<212> TYPE: DNA
<213> ORGANISM: Artificial
<220> FEATURE:
<223> OTHER INFORMATION: Bw primer F6P23

<400> SEQUENCE: 21
aagaagagaa ctgc                                                       14

<210> SEQ ID NO 22
<211> LENGTH: 11
<212> TYPE: DNA
<213> ORGANISM: Artificial
<220> FEATURE:
<223> OTHER INFORMATION: Fw primer AT2g17220-30

<400> SEQUENCE: 22
ggaagatcat a                                                          11

<210> SEQ ID NO 23
<211> LENGTH: 11
<212> TYPE: DNA
<213> ORGANISM: Artificial
<220> FEATURE:
<223> OTHER INFORMATION: Bw primer AT2g17220-30

<400> SEQUENCE: 23
gtcaaccttc c                                                          11

<210> SEQ ID NO 24
<211> LENGTH: 14
<212> TYPE: DNA
<213> ORGANISM: Artificial
<220> FEATURE:
<223> OTHER INFORMATION: FW primer T23A1
```

-continued

<400> SEQUENCE: 24
tccttccatg tccg                                                14

<210> SEQ ID NO 25
<211> LENGTH: 14
<212> TYPE: DNA
<213> ORGANISM: Artificial
<220> FEATURE:
<223> OTHER INFORMATION: Bw primer T23A1

<400> SEQUENCE: 25
aacaaatttg cttc                                                14

<210> SEQ ID NO 26
<211> LENGTH: 6
<212> TYPE: DNA
<213> ORGANISM: Artificial
<220> FEATURE:
<223> OTHER INFORMATION: Fw primer AT2g17220-30

<400> SEQUENCE: 26 aaacca                                                         6

<210> SEQ ID NO 27
<211> LENGTH: 8
<212> TYPE: DNA
<213> ORGANISM: Artificial
<220> FEATURE:
<223> OTHER INFORMATION: Bw primer AT2g17220-30

<400> SEQUENCE: 27 cagccttt                                                       8

<210> SEQ ID NO 28
<211> LENGTH: 14
<212> TYPE: DNA
<213> ORGANISM: Artificial
<220> FEATURE:
<223> OTHER INFORMATION: Fw primer AT2g17190

<400> SEQUENCE: 28
gaatagaggt tgat                                                14

<210> SEQ ID NO 29
<211> LENGTH: 14
<212> TYPE: DNA
<213> ORGANISM: Artificial
<220> FEATURE:
<223> OTHER INFORMATION: Bw primer AT2g17190

<400> SEQUENCE: 29
ctcttgtatg tttt                                                14

<210> SEQ ID NO 30
<211> LENGTH: 11
<212> TYPE: DNA
<213> ORGANISM: Artificial
<220> FEATURE:
<223> OTHER INFORMATION: Fw primer AT2g17190

<400> SEQUENCE: 30
ggaaatcaag a                                                   11

<210> SEQ ID NO 31
<211> LENGTH: 11

```
<212> TYPE: DNA
<213> ORGANISM: Artificial
<220> FEATURE:
<223> OTHER INFORMATION: Bw primer AT2g17190

<400> SEQUENCE: 31
actgggctga t                                                          11

<210> SEQ ID NO 32
<211> LENGTH: 14
<212> TYPE: DNA
<213> ORGANISM: Artificial
<220> FEATURE:
<223> OTHER INFORMATION: Fw primer AT2g17200

<400> SEQUENCE: 32
cctctccacc catt                                                       14

<210> SEQ ID NO 33
<211> LENGTH: 14
<212> TYPE: DNA
<213> ORGANISM: Artificial
<220> FEATURE:
<223> OTHER INFORMATION: Bw primer AT2g17200

<400> SEQUENCE: 33
cgatccattt cgtc                                                       14

<210> SEQ ID NO 34
<211> LENGTH: 10
<212> TYPE: DNA
<213> ORGANISM: Artificial
<220> FEATURE:
<223> OTHER INFORMATION: Fw primer AT2g17200

<400> SEQUENCE: 34
tctaatttcg                                                            10

<210> SEQ ID NO 35
<211> LENGTH: 11
<212> TYPE: DNA
<213> ORGANISM: Artificial
<220> FEATURE:
<223> OTHER INFORMATION: Bw primer AT2g17200

<400> SEQUENCE: 35
aagcaatcta c                                                          11

<210> SEQ ID NO 36
<211> LENGTH: 14
<212> TYPE: DNA
<213> ORGANISM: Artificial
<220> FEATURE:
<223> OTHER INFORMATION: Fw primer AT2g17270

<400> SEQUENCE: 36
gatgcagcta aatt                                                       14

<210> SEQ ID NO 37
<211> LENGTH: 14
<212> TYPE: DNA
<213> ORGANISM: Artificial
<220> FEATURE:
<223> OTHER INFORMATION: Bw primer AT2g17270

<400> SEQUENCE: 37
```

```
acgaaaatat caaa                                                      14

<210> SEQ ID NO 38
<211> LENGTH: 11
<212> TYPE: DNA
<213> ORGANISM: Artificial
<220> FEATURE:
<223> OTHER INFORMATION: Fw primer AT2g17270

<400> SEQUENCE: 38
atcagtgtga a                                                         11

<210> SEQ ID NO 39
<211> LENGTH: 10
<212> TYPE: DNA
<213> ORGANISM: Artificial
<220> FEATURE:
<223> OTHER INFORMATION: Bw primer AT2g17270

<400> SEQUENCE: 39
aagctccttc                                                           10

<210> SEQ ID NO 40
<211> LENGTH: 14
<212> TYPE: DNA
<213> ORGANISM: Artificial
<220> FEATURE:
<223> OTHER INFORMATION: Fw primer AT2g17300-05

<400> SEQUENCE: 40
aggtaggatg gtat                                                      14

<210> SEQ ID NO 41
<211> LENGTH: 14
<212> TYPE: DNA
<213> ORGANISM: Artificial
<220> FEATURE:
<223> OTHER INFORMATION: Bw primer AT2g17300-05

<400> SEQUENCE: 41
gcatgttttc tcta                                                      14

<210> SEQ ID NO 42
<211> LENGTH: 12
<212> TYPE: DNA
<213> ORGANISM: Artificial
<220> FEATURE:
<223> OTHER INFORMATION: Fw primer AT2g17300-05

<400> SEQUENCE: 42
tatgtttgaa ct                                                        12

<210> SEQ ID NO 43
<211> LENGTH: 11
<212> TYPE: DNA
<213> ORGANISM: Artificial
<220> FEATURE:
<223> OTHER INFORMATION: Bw primer AT2g17300-05

<400> SEQUENCE: 43
agcgatagaa g                                                         11

<210> SEQ ID NO 44
<211> LENGTH: 14
<212> TYPE: DNA
<213> ORGANISM: Artificial
```

```
<220> FEATURE:
<223> OTHER INFORMATION: Fw primer AT2g17310

<400> SEQUENCE: 44
atgggtaacg aaag                                              14

<210> SEQ ID NO 45
<211> LENGTH: 14
<212> TYPE: DNA
<213> ORGANISM: Artificial
<220> FEATURE:
<223> OTHER INFORMATION: Bw primer AT2g17310

<400> SEQUENCE: 45
cacatgtata aggt                                              14

<210> SEQ ID NO 46
<211> LENGTH: 11
<212> TYPE: DNA
<213> ORGANISM: Artificial
<220> FEATURE:
<223> OTHER INFORMATION: Fw primer AT2g17310

<400> SEQUENCE: 46
agaggattag t                                                 11

<210> SEQ ID NO 47
<211> LENGTH: 11
<212> TYPE: DNA
<213> ORGANISM: Artificial
<220> FEATURE:
<223> OTHER INFORMATION: Bw primer AT2g17310

<400> SEQUENCE: 47
cttcccatag a                                                 11

<210> SEQ ID NO 48
<211> LENGTH: 14
<212> TYPE: DNA
<213> ORGANISM: Artificial
<220> FEATURE:
<223> OTHER INFORMATION: Fw primer AT2g17360

<400> SEQUENCE: 48
ccaacaagta tcct                                              14

<210> SEQ ID NO 49
<211> LENGTH: 14
<212> TYPE: DNA
<213> ORGANISM: Artificial
<220> FEATURE:
<223> OTHER INFORMATION: Bw primer AT2g17360

<400> SEQUENCE: 49
ccacatcaaa ctta                                              14

<210> SEQ ID NO 50
<211> LENGTH: 11
<212> TYPE: DNA
<213> ORGANISM: Artificial
<220> FEATURE:
<223> OTHER INFORMATION: Fw primer AT2g17360

<400> SEQUENCE: 50
cttttgttgt t                                                 11
```

<210> SEQ ID NO 51
<211> LENGTH: 11
<212> TYPE: DNA
<213> ORGANISM: Artificial
<220> FEATURE:
<223> OTHER INFORMATION: Bw primer AT2g17360

<400> SEQUENCE: 51
atgaactcca c                                                              11

<210> SEQ ID NO 52
<211> LENGTH: 25
<212> TYPE: DNA
<213> ORGANISM: Artificial
<220> FEATURE:
<223> OTHER INFORMATION: Primer MvD17230_F

<400> SEQUENCE: 52
ttcccgaagt gtacattaaa agctc                                               25

<210> SEQ ID NO 53
<211> LENGTH: 25
<212> TYPE: DNA
<213> ORGANISM: Artificial
<220> FEATURE:
<223> OTHER INFORMATION: Primer MvD17230_R

<400> SEQUENCE: 53
tatgtcatcc ccaagagaag aagac                                               25

<210> SEQ ID NO 54
<211> LENGTH: 25
<212> TYPE: DNA
<213> ORGANISM: Artificial
<220> FEATURE:
<223> OTHER INFORMATION: Primer MvD17240_F

<400> SEQUENCE: 54
caataaaagc ctttaaaagc ccact                                               25

<210> SEQ ID NO 55
<211> LENGTH: 25
<212> TYPE: DNA
<213> ORGANISM: Artificial
<220> FEATURE:
<223> OTHER INFORMATION: Primer MvD17240_R

<400> SEQUENCE: 55
tagcttctga aactgtggca ttaca                                               25

<210> SEQ ID NO 56
<211> LENGTH: 25
<212> TYPE: DNA
<213> ORGANISM: Artificial
<220> FEATURE:
<223> OTHER INFORMATION: Primer MvD17250_1F

<400> SEQUENCE: 56
catgatttga ggggtatatc caaaa                                               25

<210> SEQ ID NO 57
<211> LENGTH: 25
<212> TYPE: DNA
<213> ORGANISM: Artificial
<220> FEATURE:
<223> OTHER INFORMATION: Primer MvD17250_1R -continued

<400> SEQUENCE: 57
ggaggtggga tttgagataa aactt                                              25

<210> SEQ ID NO 58
<211> LENGTH: 25
<212> TYPE: DNA
<213> ORGANISM: Artificial
<220> FEATURE:
<223> OTHER INFORMATION: Primer MvD17250_2F

<400> SEQUENCE: 58
tagcctagaa ctctctgttc gcaag                                              25

<210> SEQ ID NO 59
<211> LENGTH: 25
<212> TYPE: DNA
<213> ORGANISM: Artificial
<220> FEATURE:
<223> OTHER INFORMATION: Primer MvD17250_2R

<400> SEQUENCE: 59
cattattttg cgtagttgtg agtgg                                              25

<210> SEQ ID NO 60
<211> LENGTH: 25
<212> TYPE: DNA
<213> ORGANISM: Artificial
<220> FEATURE:
<223> OTHER INFORMATION: Primer MvD17250_3F

<400> SEQUENCE: 60
cgaagaaatc ctacaatcaa ccatc                                              25

<210> SEQ ID NO 61
<211> LENGTH: 25
<212> TYPE: DNA
<213> ORGANISM: Artificial
<220> FEATURE:
<223> OTHER INFORMATION: Primer MvD17250_3R

<400> SEQUENCE: 61
tctcacaatt cccatctctt actcc                                              25

<210> SEQ ID NO 62
<211> LENGTH: 25
<212> TYPE: DNA
<213> ORGANISM: Artificial
<220> FEATURE:
<223> OTHER INFORMATION: Primer MvD17260_1F

<400> SEQUENCE: 62
ttactcattt gggtgaacag aacaa                                              25

<210> SEQ ID NO 63
<211> LENGTH: 25
<212> TYPE: DNA
<213> ORGANISM: Artificial
<220> FEATURE:
<223> OTHER INFORMATION: Primer MvD17260_1R

<400> SEQUENCE: 63
atcatcccta atctctctgc ttcct                                              25

<210> SEQ ID NO 64

```
<211> LENGTH: 25
<212> TYPE: DNA
<213> ORGANISM: Artificial
<220> FEATURE:
<223> OTHER INFORMATION: Primer MvD17260_2F

<400> SEQUENCE: 64
gattaagata cggggaatgg agtct                                    25

<210> SEQ ID NO 65
<211> LENGTH: 25
<212> TYPE: DNA
<213> ORGANISM: Artificial
<220> FEATURE:
<223> OTHER INFORMATION: Primer MvD17260_2R

<400> SEQUENCE: 65
atgcagacaa ataagatggc tcttg                                    25

<210> SEQ ID NO 66
<211> LENGTH: 25
<212> TYPE: DNA
<213> ORGANISM: Artificial
<220> FEATURE:
<223> OTHER INFORMATION: Primer MvD17260_3F

<400> SEQUENCE: 66
gttgttgctc ctgtcacaag actta                                    25

<210> SEQ ID NO 67
<211> LENGTH: 25
<212> TYPE: DNA
<213> ORGANISM: Artificial
<220> FEATURE:
<223> OTHER INFORMATION: Primer MvD17260_3R

<400> SEQUENCE: 67
gaacaaagac gaagccttta aacaa                                    25

<210> SEQ ID NO 68
<211> LENGTH: 25
<212> TYPE: DNA
<213> ORGANISM: Artificial
<220> FEATURE:
<223> OTHER INFORMATION: Primer MvD17265_F

<400> SEQUENCE: 68
gaggactgca tctagaagac ccata                                    25

<210> SEQ ID NO 69
<211> LENGTH: 25
<212> TYPE: DNA
<213> ORGANISM: Artificial
<220> FEATURE:
<223> OTHER INFORMATION: Primer MvD17265_R

<400> SEQUENCE: 69
tgggctctca actataaagt ttgct                                    25

<210> SEQ ID NO 70
<211> LENGTH: 25
<212> TYPE: DNA
<213> ORGANISM: Artificial
<220> FEATURE:
<223> OTHER INFORMATION: Primer MvD17270_1F

<400> SEQUENCE: 70
```
taacggtaaa gcaacgaatc tatcc                                              25

<210> SEQ ID NO 71
<211> LENGTH: 25
<212> TYPE: DNA
<213> ORGANISM: Artificial
<220> FEATURE:
<223> OTHER INFORMATION: Primer MvD17270_1R

<400> SEQUENCE: 71
tcaaactgat aacgagagac gttga                                              25

<210> SEQ ID NO 72
<211> LENGTH: 25
<212> TYPE: DNA
<213> ORGANISM: Artificial
<220> FEATURE:
<223> OTHER INFORMATION: Primer MvD17270_2F

<400> SEQUENCE: 72
ttgcgttcgt ttttgagtct tttat                                              25

<210> SEQ ID NO 73
<211> LENGTH: 25
<212> TYPE: DNA
<213> ORGANISM: Artificial
<220> FEATURE:
<223> OTHER INFORMATION: Primer MvD17270_2R

<400> SEQUENCE: 73
aaaccagact cattcctttg acatc                                              25

<210> SEQ ID NO 74
<211> LENGTH: 25
<212> TYPE: DNA
<213> ORGANISM: Artificial
<220> FEATURE:
<223> OTHER INFORMATION: Primer MvD17280_1F

<400> SEQUENCE: 74
tttaggatct ctgccttttc tcaac                                              25

<210> SEQ ID NO 75
<211> LENGTH: 25
<212> TYPE: DNA
<213> ORGANISM: Artificial
<220> FEATURE:
<223> OTHER INFORMATION: Primer MvD17280_1R

<400> SEQUENCE: 75
gagaaatcaa tagcgggaaa gagag                                              25

<210> SEQ ID NO 76
<211> LENGTH: 25
<212> TYPE: DNA
<213> ORGANISM: Artificial
<220> FEATURE:
<223> OTHER INFORMATION: Primer MvD17280_2F

<400> SEQUENCE: 76
gcttaaatag tcctcctttc cttgc                                              25

<210> SEQ ID NO 77
<211> LENGTH: 25
<212> TYPE: DNA

<213> ORGANISM: Artificial
<220> FEATURE:
<223> OTHER INFORMATION: Primer MvD17280_2R

<400> SEQUENCE: 77
tctgctggtt ctcatgttga tagag                                    25

<210> SEQ ID NO 78
<211> LENGTH: 25
<212> TYPE: DNA
<213> ORGANISM: Artificial
<220> FEATURE:
<223> OTHER INFORMATION: Primer MvD17290_1F

<400> SEQUENCE: 78
ctctccttca tcatttcaca aatcc                                    25

<210> SEQ ID NO 79
<211> LENGTH: 25
<212> TYPE: DNA
<213> ORGANISM: Artificial
<220> FEATURE:
<223> OTHER INFORMATION: Primer MvD17290_1R

<400> SEQUENCE: 79
ttcctctcgc tgtaatgacc tctat                                    25

<210> SEQ ID NO 80
<211> LENGTH: 21
<212> TYPE: DNA
<213> ORGANISM: Artificial
<220> FEATURE:
<223> OTHER INFORMATION: Primer MvD17290_2F

<400> SEQUENCE: 80
tgccacaggt gttgactatg c                                        21

<210> SEQ ID NO 81
<211> LENGTH: 21
<212> TYPE: DNA
<213> ORGANISM: Artificial
<220> FEATURE:
<223> OTHER INFORMATION: Primer MvD17290_2R

<400> SEQUENCE: 81
tgctcttaaa cccgcaatct c                                        21

<210> SEQ ID NO 82
<211> LENGTH: 26
<212> TYPE: DNA
<213> ORGANISM: Artificial
<220> FEATURE:
<223> OTHER INFORMATION: Primer MvD17290_3F

<400> SEQUENCE: 82
gaagatggct ttaaaggtca gtttgt                                   26

<210> SEQ ID NO 83
<211> LENGTH: 25
<212> TYPE: DNA
<213> ORGANISM: Artificial
<220> FEATURE:
<223> OTHER INFORMATION: Primer MvD17290_3R

<400> SEQUENCE: 83
agcaacaaca actaaaaggt ggaag                                    25

<210> SEQ ID NO 84
<211> LENGTH: 370
<212> TYPE: PRT
<213> ORGANISM: Arabidopsis thaliana

<400> SEQUENCE: 84

Met Ala Ser Leu Cys Phe Gln Ser Pro Ser Lys Pro Ile Ser Tyr Phe
1               5                   10                  15

Gln Pro Lys Ser Asn Pro Ser Pro Leu Phe Ala Lys Val Ser Val
            20                  25                  30

Phe Arg Cys Arg Ala Ser Val Gln Thr Leu Val Ala Val Glu Pro Glu
        35                  40                  45

Pro Val Phe Val Ser Val Lys Thr Phe Ala Pro Ala Thr Val Ala Asn
    50                  55                  60

Leu Gly Pro Gly Phe Asp Phe Leu Gly Cys Ala Val Asp Gly Leu Gly
65                  70                  75                  80

Asp His Val Thr Leu Arg Val Asp Pro Ser Val Arg Ala Gly Glu Val
                85                  90                  95

Ser Ile Ser Glu Ile Thr Gly Thr Thr Thr Lys Leu Ser Thr Asn Pro
            100                 105                 110

Leu Arg Asn Cys Ala Gly Ile Ala Ala Ile Ala Thr Met Lys Met Leu
        115                 120                 125

Gly Ile Arg Ser Val Gly Leu Ser Leu Asp Leu His Lys Gly Leu Pro
130                 135                 140

Leu Gly Ser Gly Leu Gly Ser Ser Ala Ala Ser Ala Ala Ala Ala Ala
145                 150                 155                 160

Val Ala Val Asn Glu Ile Phe Gly Arg Lys Leu Gly Ser Asp Gln Leu
                165                 170                 175

Val Leu Ala Gly Leu Glu Ser Glu Ala Lys Val Ser Gly Tyr His Ala
            180                 185                 190

Asp Asn Ile Ala Pro Ala Ile Met Gly Gly Phe Val Leu Ile Arg Asn
        195                 200                 205

Tyr Glu Pro Leu Asp Leu Lys Pro Leu Arg Phe Pro Ser Asp Lys Asp
    210                 215                 220

Leu Phe Phe Val Leu Val Ser Pro Asp Phe Glu Ala Pro Thr Lys Lys
225                 230                 235                 240

Met Arg Ala Ala Leu Pro Thr Glu Ile Pro Met Val His His Val Trp
                245                 250                 255

Asn Ser Ser Gln Ala Ala Ala Leu Val Ala Ala Val Leu Glu Gly Asp
            260                 265                 270

Ala Val Met Leu Gly Lys Ala Leu Ser Ser Asp Lys Ile Val Glu Pro
        275                 280                 285

Thr Arg Ala Pro Leu Ile Pro Gly Met Glu Ala Val Lys Lys Ala Ala
    290                 295                 300

Leu Glu Ala Gly Ala Phe Gly Cys Thr Ile Ser Gly Ala Gly Pro Thr
305                 310                 315                 320

Ala Val Ala Val Ile Asp Ser Glu Glu Lys Gly Gln Val Ile Gly Glu
                325                 330                 335

Lys Met Val Glu Ala Phe Trp Lys Val Gly His Leu Lys Ser Val Ala
            340                 345                 350

Ser Val Lys Lys Leu Asp Asn Val Gly Ala Arg Leu Val Asn Ser Val
        355                 360                 365

Ser Arg

<210> SEQ ID NO 85
<211> LENGTH: 366
<212> TYPE: PRT
<213> ORGANISM: Citrus sinensis

<400> SEQUENCE: 85

```
Met Ala Ile Cys Phe Ser Ser Ala Val Lys Pro Ala Asn His Phe Thr
 1               5                  10                  15

Val Phe Phe Asn Pro Ala Pro Lys Lys Pro Ile Phe Lys Cys Ser Cys
                20                  25                  30

Ser Leu Pro Thr Val Thr Thr Glu Pro Glu Pro Val Phe Thr Ser
             35                  40                  45

Val Lys Thr Phe Ala Pro Ala Thr Val Ala Asn Leu Gly Pro Cys Phe
 50                  55                  60

Asp Phe Leu Gly Cys Ala Val Asp Gly Leu Gly Asp Tyr Val Ser Leu
 65                  70                  75                  80

Lys Val Asp Pro Ser Val His Pro Gly Glu Val Ser Ile Ser Glu Val
                 85                  90                  95

Ile Gly Pro Ser Lys Leu Ser Lys Asn Pro Leu Trp Asn Cys Ala Gly
            100                 105                 110

Ile Ala Ala Ile Ser Ala Met Lys Met Leu Gly Val Arg Ser Val Gly
            115                 120                 125

Leu Ser Leu Ser Leu Glu Lys Gly Leu Pro Leu Gly Ser Gly Leu Gly
        130                 135                 140

Ser Ser Ala Ala Ser Ala Ala Ala Ala Val Ala Val Asn Glu Met
145                 150                 155                 160

Phe Gly Asn Lys Leu Leu Pro Asp Glu Leu Val Leu Ala Gly Leu Glu
                165                 170                 175

Ser Glu Ala Lys Val Ser Gly Tyr His Ala Asp Asn Ile Ala Pro Ala
            180                 185                 190

Ile Met Gly Gly Phe Val Leu Ile Arg Ser Tyr Glu Pro Leu Asp Leu
        195                 200                 205

Met Arg Leu Asn Phe Pro Glu Lys Lys Gln Leu Leu Phe Val Leu Val
210                 215                 220

Thr Pro Glu Phe Glu Ala Pro Thr Lys Lys Met Arg Ala Ala Leu Pro
225                 230                 235                 240

Ala Glu Val Gly Met Pro His His Ile Trp Asn Cys Ser Gln Ala Gly
                245                 250                 255

Ala Leu Val Ala Ala Val Leu Asn Gly Asp Pro Val Gly Leu Gly Lys
            260                 265                 270

Ala Leu Ser Ser Asp Lys Ile Val Glu Pro Asn Arg Ala Pro Leu Ile
        275                 280                 285

Pro Gly Met Glu Ala Val Lys Lys Val Ala Val Glu Ala Gly Ala Tyr
290                 295                 300

Gly Cys Thr Ile Ser Gly Ala Gly Pro Thr Ala Val Ala Val Val Asp
305                 310                 315                 320

Asn Glu Glu Lys Gly Lys Val Ile Gly Glu Lys Met Val Glu Ala Phe
                325                 330                 335

Trp Lys Glu Gly Asn Leu Lys Ala Val Ser Met Val Lys Arg Leu Asp
            340                 345                 350

Arg Val Gly Ala Arg Leu Val Gly Ser Val Arg Ala Pro Arg
        355                 360                 365
```

<210> SEQ ID NO 86
<211> LENGTH: 366
<212> TYPE: PRT
<213> ORGANISM: Populus trichocarpa

<400> SEQUENCE: 86

```
Met Ala Ile Cys Cys Phe Pro Ser Pro Leu Lys Pro Met Thr Pro Ala
1               5                   10                  15

Thr Pro Leu Thr Asn Leu Lys Pro Lys Arg Pro Asp Ile Leu Arg Cys
            20                  25                  30

Asn Phe Ser Leu Pro Thr Ile Thr Thr Glu Pro Glu Pro Val Phe
        35                  40                  45

Thr Ser Val Arg Ser Phe Ala Pro Ala Thr Val Ala Asn Leu Gly Pro
    50                  55                  60

Gly Phe Asp Phe Leu Gly Cys Ala Val Asp Gly Leu Gly Asp Phe Val
65                  70                  75                  80

Ser Leu Arg Val Asp Pro Ser Val His Pro Gly Glu Leu Ser Ile Ser
                85                  90                  95

Asp Ile Ser Gly Pro Lys Lys Leu Ser Lys Asn Pro Leu Tyr Asn Cys
            100                 105                 110

Ala Gly Ile Ala Ala Ile Ala Thr Met Lys Met Leu Asn Ile Arg Ser
        115                 120                 125

Val Gly Leu Ser Leu Ser Leu Glu Lys Gly Leu Pro Leu Gly Ser Gly
    130                 135                 140

Leu Gly Ser Ser Ala Ala Ser Ala Ala Ala Ala Val Ala Val Asn
145                 150                 155                 160

Glu Leu Phe Gly Arg Lys Leu Glu Val Lys Asp Leu Val Leu Ala Gly
                165                 170                 175

Leu Glu Ser Glu Ala Lys Val Ser Gly Tyr His Ala Asp Asn Ile Ala
            180                 185                 190

Pro Ala Ile Met Gly Gly Phe Val Leu Ile Arg Ser Tyr Asp Pro Leu
        195                 200                 205

Glu Leu Met Ser Leu Gln Phe Pro Val Glu Lys Asp Leu Ile Phe Val
    210                 215                 220

Leu Val Ser Pro Asp Phe Glu Ala Pro Thr Lys Lys Met Arg Ala Ala
225                 230                 235                 240

Leu Pro Ala Glu Ile Gly Met Ser His His Val Trp Asn Cys Ser Gln
                245                 250                 255

Ala Gly Ala Phe Val Ala Ser Val Leu Gln Gly Asp Leu Val Gly Leu
            260                 265                 270

Gly Lys Ala Leu Ser Ser Asp Lys Ile Val Glu Pro Lys Arg Ala Pro
        275                 280                 285

Leu Ile Pro Gly Met Val Gly Val Lys Lys Ala Leu Glu Ala Gly
    290                 295                 300

Ala Phe Gly Cys Thr Ile Ser Gly Ala Gly Pro Thr Ala Val Ala Val
305                 310                 315                 320

Val Gly Ser Glu Asp Arg Gly Val Glu Val Gly Glu Arg Met Val Glu
                325                 330                 335

Ala Phe Trp Lys Glu Gly Asn Leu Lys Ala Val Ala Met Val Lys Arg
            340                 345                 350

Leu Asp Arg Val Gly Ala Arg Leu Val Gly Ser Val Pro Arg
        355                 360                 365
```

<210> SEQ ID NO 87

<211> LENGTH: 365
<212> TYPE: PRT
<213> ORGANISM: Solanum tuberosum

<400> SEQUENCE: 87

```
Met Ala Val Leu Cys Gln Ser Pro Leu Asn Leu Lys Leu Ile Thr Ser
 1               5                   10                  15

Ser Ser Ser Ser Ser Arg Asn Arg Thr Ala Asn Pro Ser Phe Arg Leu
            20                  25                  30

Asn Leu Ser Ala His Ser Arg Ser Glu Pro Ser Pro Val Phe Thr Ser
        35                  40                  45

Val Lys Ser Phe Ala Pro Ala Thr Val Ala Asn Leu Gly Pro Gly Phe
 50                  55                  60

Asp Phe Leu Gly Cys Ala Val Asp Gly Ile Gly Asp Phe Val Thr Leu
 65                  70                  75                  80

Arg Leu Asp Pro Asn Val His Pro Gly Glu Val Ser Ile Ser Asp Ile
                85                  90                  95

Ser Gly Ala Gly Lys Lys Leu Arg Arg Asn Pro Arg Trp Asn Cys Ala
            100                 105                 110

Gly Ile Ala Ala Ile Ser Val Met Lys Met Leu Asn Ile Arg Ser Val
        115                 120                 125

Gly Leu Thr Leu Ser Leu His Lys Gly Leu Pro Leu Gly Ser Gly Leu
    130                 135                 140

Gly Ser Ser Ala Ala Ser Ala Ala Ala Ala Val Ala Val Asn Glu
145                 150                 155                 160

Leu Phe Gly His Pro Leu Thr Leu Thr Asp Leu Val Leu Ala Gly Leu
                165                 170                 175

Asp Ser Glu Ser Lys Val Ser Gly Tyr His Ala Asp Asn Val Ala Pro
            180                 185                 190

Ala Ile Met Gly Gly Phe Val Leu Ile Arg Ser Tyr His Pro Leu Glu
        195                 200                 205

Leu Ile Gln Leu Asn Phe Pro His Glu Lys Asp Leu Phe Phe Val Leu
    210                 215                 220

Ala Asn Pro Glu Phe Glu Ala Pro Thr Lys Lys Met Arg Glu Ala Leu
225                 230                 235                 240

Pro Gln Glu Ile Thr Met Ser His His Ile Trp Asn Cys Ser Gln Ala
                245                 250                 255

Gly Ala Leu Val Ala Ser Val Leu Leu Gly Asp Val Ser Gly Phe Gly
            260                 265                 270

Lys Ala Leu Ser Ser Asp Lys Ile Val Glu Pro Arg Arg Thr Pro Leu
        275                 280                 285

Ile Pro Gly Met Glu Gly Val Lys Lys Ala Ala Met Glu Ala Gly Ala
    290                 295                 300

Phe Gly Cys Thr Ile Ser Gly Ala Gly Pro Thr Val Ala Val Thr
305                 310                 315                 320

Asp Asn Glu Glu Thr Gly Arg Glu Ile Gly Arg Met Val Glu Ala
                325                 330                 335

Phe Leu Glu His Gly Lys Leu Lys Ala Leu Ala Met Val Lys Lys Leu
            340                 345                 350

Asp Arg Ile Gly Ala Arg Leu Val Ser Ser Gln Pro Ile
        355                 360                 365
```

<210> SEQ ID NO 88
<211> LENGTH: 266
<212> TYPE: PRT

<213> ORGANISM: Vitis vinifera

<400> SEQUENCE: 88

Met Ala Ile Cys Phe His Ser Pro Ser Lys Pro Thr Cys Ile Ser Pro
1               5                   10                  15

Ser Ser Asn His Tyr Arg Pro Asn Leu His Ala Arg Ser Phe Arg Cys
            20                  25                  30

Asn Phe Ser Lys Thr Leu Thr Ala Asp Pro Gln Pro Val Phe Thr Ser
        35                  40                  45

Val Lys Ser Phe Ala Pro Ala Thr Val Ala Asn Leu Gly Pro Gly Phe
    50                  55                  60

Asp Phe Leu Gly Ala Ala Val Asp Gly Ile Gly Asp Phe Val Ser Leu
65                  70                  75                  80

Arg Val Asp Pro Asp Val Arg Pro Gly Glu Ile Ala Ile Val Asp Ile
                85                  90                  95

Asp Gly Val Gly Asn Ser Ala Lys Lys Leu Ser Lys Asn Pro Leu Trp
            100                 105                 110

Asn Cys Ala Gly Ile Ala Ala Ile Ser Val Met Lys Met Leu Gly Val
        115                 120                 125

Arg Ser Val Gly Leu Ser Leu Ser Leu Glu Lys Gly Leu Pro Leu Gly
    130                 135                 140

Ser Gly Leu Gly Ser Ser Ala Ala Ser Ala Ala Ala Ala Val Ala
145                 150                 155                 160

Val Asn Glu Ile Phe Gly Arg Lys Leu Gly Val Asp Asp Leu Val Leu
                165                 170                 175

Ala Gly Leu Asp Ser Glu Gly Pro Arg Arg Ala Pro Leu Ile Pro Gly
            180                 185                 190

Met Glu Gly Val Lys Lys Ala Ala Leu Glu Ala Gly Ala Phe Gly Cys
        195                 200                 205

Thr Ile Ser Gly Ala Gly Pro Thr Ala Val Ala Ile Thr Asp Asp Glu
    210                 215                 220

Glu Lys Gly Arg Glu Ile Gly Glu Arg Met Val Glu Ala Phe Leu Glu
225                 230                 235                 240

Glu Gly Lys Leu Lys Ala Val Ala Met Val Lys Gln Leu Asp Arg Val
                245                 250                 255

Gly Ala Arg Leu Met Ser Ser Asn Leu Arg
            260                 265

<210> SEQ ID NO 89
<211> LENGTH: 226
<212> TYPE: PRT
<213> ORGANISM: Lactuca sativa
<220> FEATURE:
<221> NAME/KEY: misc_feature
<222> LOCATION: (16)..(16)
<223> OTHER INFORMATION: Xaa can be any naturally occurring amino acid

<400> SEQUENCE: 89

Met Ala Ile Arg His Tyr Gln Pro Pro Phe Ala Ser Thr Ser Ser Xaa
1               5                   10                  15

Ile Phe Ser Thr Asp Leu Phe Lys Pro Pro Lys Leu Tyr Leu Ser Ser
            20                  25                  30

Ser Val Arg Cys Asn Ile Ser Val Ala Ser Lys Leu Glu Pro Glu Pro
        35                  40                  45

His Pro Val Phe Thr Ser Val Lys Ser Phe Ala Pro Ala Thr Val Ala
    50                  55                  60

```
Asn Leu Gly Pro Gly Phe Asp Phe Leu Gly Cys Ala Ile Asp Gly Ile
 65                  70                  75                  80

Gly Asp Tyr Val Thr Leu Thr Val Asp Pro Gln Val Gln Pro Gly Arg
                 85                  90                  95

Leu Ser Ile Ala Glu Ile Asn Gly Val Asp Lys Ser Ser Lys Arg Leu
            100                 105                 110

Ser Arg Asn Pro Leu Trp Asn Cys Ala Gly Ile Ala Ala Ile Ser Val
        115                 120                 125

Met Lys Met Leu Lys Ile Arg Ser Val Gly Leu Ser Leu Ser Glu Pro
130                 135                 140

Arg Arg Ala Pro Leu Ile Pro Gly Met Asp Ala Val Lys Lys Ala Ala
145                 150                 155                 160

Leu Glu Ala Gly Ala Tyr Gly Cys Thr Ile Ser Gly Ala Gly Pro Thr
                165                 170                 175

Ala Val Ala Val Thr Asp Asn Glu Glu Lys Gly Arg Glu Ile Gly Glu
            180                 185                 190

Lys Met Val Glu Ala Phe Met Ala Glu Gly Asn Leu Lys Ala Val Ala
        195                 200                 205

Met Val Lys Gln Leu Asp Arg Val Gly Ala Arg Leu Val Ser Ser Ile
210                 215                 220

Ser Arg
225

<210> SEQ ID NO 90
<211> LENGTH: 376
<212> TYPE: PRT
<213> ORGANISM: Solanum tuberosum

<400> SEQUENCE: 90

Met Ala Ile Thr Tyr Gln Ser Pro Met Lys Leu Asn Phe Ile Thr Ser
  1               5                  10                  15

Asn Gly Phe Ser Asn Pro Pro Ser Leu Tyr Pro Ile Asn Thr His Phe
                 20                  25                  30

Ser Phe Gly Phe Asn Leu Ser Ser Val Ser Ser Lys Thr Gln Thr His
            35                  40                  45

Ile Thr Ile Pro Glu Pro Glu Pro Val Phe Thr Ser Val Lys Ser Phe
 50                  55                  60

Ala Pro Ala Thr Val Ala Asn Leu Gly Pro Gly Phe Asp Phe Leu Gly
 65                  70                  75                  80

Cys Ala Val Asp Gly Ile Gly Asp Phe Val Thr Leu Arg Val Asp Pro
                 85                  90                  95

Asn Val Lys Ala Gly Glu Val Ser Ile Ser Asp Ile Ser Gly Ala Gly
            100                 105                 110

Asn Arg Leu Ser Lys Asp Pro Leu Ser Asn Cys Ala Gly Ile Ala Ala
        115                 120                 125

Ile Ser Val Met Lys Met Leu Asn Ile Gln Ser Val Gly Leu Ser Ile
130                 135                 140

Ser Leu Glu Lys Gly Leu Pro Leu Gly Ser Gly Leu Gly Ser Ser Ala
145                 150                 155                 160

Ala Ser Ala Ala Ala Ala Val Ala Val Asn Glu Ile Phe Gly Arg
                165                 170                 175

Lys Leu Ser Val Asp Asp Leu Val Leu Ala Gly Leu Glu Ser Glu Thr
            180                 185                 190

Lys Val Ser Gly Tyr His Ala Asp Asn Ile Ala Pro Ser Ile Met Gly
        195                 200                 205
```

```
Gly Phe Val Leu Val Arg Ser Tyr Asp Pro Leu Glu Leu Ile Ser Leu
        210                 215                 220

Lys Phe Pro Phe Glu Lys Asp Leu Phe Phe Val Leu Val Asn Pro Glu
225                 230                 235                 240

Phe Glu Ala Pro Thr Lys Lys Met Arg Ala Val Leu Pro Ser Glu Val
                245                 250                 255

Thr Met Ser His His Ile Trp Asn Cys Ser Gln Ala Gly Ala Leu Val
                260                 265                 270

Ala Ala Ile Leu Gln Gly Asp Ser Arg Gly Leu Gly Lys Ala Leu Ser
            275                 280                 285

Ser Asp Lys Ile Val Glu Pro Arg Arg Gly Pro Leu Ile Pro Gly Met
290                 295                 300

Glu Gly Val Lys Lys Ala Ala Leu Lys Ala Gly Ala Phe Gly Cys Thr
305                 310                 315                 320

Ile Ser Gly Ala Gly Pro Thr Leu Val Ala Val Thr Asp Asp Glu Glu
                325                 330                 335

Arg Gly Arg Glu Ile Gly Glu Arg Met Val Asp Ala Phe Met Lys Glu
            340                 345                 350

Gly Asn Leu Lys Ala Leu Ala Met Val Lys Lys Leu Asp Arg Val Gly
355                 360                 365

Ala Arg Leu Val Ser Ser Asn Ser
        370                 375

<210> SEQ ID NO 91
<211> LENGTH: 376
<212> TYPE: PRT
<213> ORGANISM: solanum lycopersicum

<400> SEQUENCE: 91

Met Ala Ile Thr Tyr Gln Ser Pro Met Lys Leu Asn Phe Ile Thr Ser
1               5                   10                  15

Asn Gly Phe Ser Asn Pro Pro Ser Leu Tyr Pro Ile Asn Thr His Phe
            20                  25                  30

Ser Phe Gly Phe Asn Leu Ser Ser Val Ser Ser Lys Thr Gln Thr His
        35                  40                  45

Ile Thr Ile Pro Glu Pro Glu Pro Val Phe Thr Ser Val Lys Ser Phe
    50                  55                  60

Ala Pro Ala Thr Val Ala Asn Leu Gly Pro Gly Phe Asp Phe Leu Gly
65                  70                  75                  80

Cys Ala Val Asp Gly Val Gly Asp Phe Val Thr Leu Arg Val Asp Pro
                85                  90                  95

Asn Val Lys Ala Gly Glu Val Ser Ile Ser Asp Ile Ser Gly Ala Gly
            100                 105                 110

Asn Arg Leu Ser Lys Asp Pro Leu Ser Asn Cys Ala Gly Ile Ala Ala
        115                 120                 125

Ile Ser Val Met Lys Met Leu Asn Ile Gln Ser Val Gly Leu Ser Ile
    130                 135                 140

Ser Leu Glu Lys Gly Leu Pro Leu Gly Ser Gly Leu Gly Ser Ser Ala
145                 150                 155                 160

Ala Ser Ala Ala Ala Ala Val Ala Val Asn Glu Ile Phe Gly Arg
                165                 170                 175

Lys Leu Ser Val Asp Asp Leu Val Leu Ala Gly Leu Glu Ser Glu Thr
            180                 185                 190

Lys Val Ser Gly Tyr His Ala Asp Asn Ile Ala Pro Ser Ile Met Gly
```

```
            195                 200                 205
Gly Phe Val Leu Val Arg Ser Tyr Asp Pro Leu Glu Leu Ile Ser Leu
210                 215                 220

Lys Phe Pro Phe Glu Lys Asp Leu Phe Phe Val Leu Val Asn Pro Glu
225                 230                 235                 240

Phe Glu Ala Pro Thr Lys Lys Met Arg Ala Val Leu Pro Ser Glu Val
                245                 250                 255

Thr Met Ser His His Ile Trp Asn Cys Ser Gln Ala Gly Ala Leu Val
                260                 265                 270

Ala Ala Ile Leu Gln Gly Asp Ser Arg Gly Leu Gly Lys Ala Leu Ser
            275                 280                 285

Ser Asp Lys Ile Val Glu Pro Arg Arg Gly Pro Leu Ile Pro Gly Met
290                 295                 300

Glu Gly Val Lys Lys Ala Leu Lys Ala Gly Ala Phe Gly Cys Thr
305                 310                 315                 320

Ile Ser Gly Ala Gly Pro Thr Leu Val Ala Val Thr Asp Asp Glu Glu
                325                 330                 335

Arg Gly Arg Glu Ile Gly Glu Arg Met Val Asp Ala Phe Met Lys Glu
                340                 345                 350

Gly Asn Leu Lys Ala Leu Ala Met Val Lys Leu Asp Arg Val Gly
            355                 360                 365

Ala Arg Leu Val Ser Ser Asn Ser
370                 375

<210> SEQ ID NO 92
<211> LENGTH: 384
<212> TYPE: PRT
<213> ORGANISM: Nicotiana benthamiana

<400> SEQUENCE: 92

Met Ala Ala Ile Cys Tyr Gln Ser Pro Val Lys Leu Asn Phe Thr Thr
1               5                   10                  15

Ser Asn Ala Phe Ser Asn Pro Ile Pro Asn Asn Pro Pro Pro Leu Tyr
                20                  25                  30

Pro Ile Lys Thr Arg Phe Ser Ser Gly Phe Asn Leu Ser Ala Val Pro
            35                  40                  45

Ser Lys Thr Gln Thr Thr His Ile Thr Ile Pro Glu Pro Glu Pro Val
50                  55                  60

Phe Ala Ser Val Lys Ser Phe Ala Pro Ala Thr Val Ala Asn Leu Gly
65                  70                  75                  80

Pro Gly Phe Asp Phe Leu Gly Cys Ala Val Asp Gly Ile Gly Asp Phe
                85                  90                  95

Ile Thr Leu Arg Val Asp Ser Lys Val Lys Pro Gly Glu Val Ser Ile
            100                 105                 110

Ser Asp Ile Ser Gly Ala Gly Gly Lys Leu Ser Lys Asp Pro Leu Ser
            115                 120                 125

Asn Cys Ala Gly Ile Ala Ala Ile Ser Val Met Lys Met Leu Asn Ile
            130                 135                 140

Gln Ser Val Gly Leu Ser Ile Ser Leu Glu Lys Gly Leu Pro Leu Gly
145                 150                 155                 160

Ser Gly Leu Gly Ser Ser Ala Ala Ser Ala Ala Ala Ala Val Ala
                165                 170                 175

Val Asn Glu Leu Phe Gly Gly Lys Leu Ser Val Ser Asp Leu Val Leu
                180                 185                 190
```

```
Ala Gly Leu Glu Ser Glu Thr Lys Val Ser Gly Tyr His Ala Asp Asn
            195                 200                 205

Ile Ala Pro Ala Ile Met Gly Gly Phe Val Leu Ile Arg Ser Tyr Asp
    210                 215                 220

Pro Leu Glu Leu Ile Glu Leu Lys Phe Pro Leu Glu Lys Asp Leu Phe
225                 230                 235                 240

Phe Val Leu Val Asn Pro Glu Phe Glu Ala Pro Thr Lys Lys Met Arg
                245                 250                 255

Ala Ala Leu Pro Asn Glu Val Thr Met Ser His His Ile Trp Asn Ser
            260                 265                 270

Ser Gln Ala Gly Ala Leu Val Ala Ala Ile Leu Gln Gly Asp Ser Arg
        275                 280                 285

Gly Leu Gly Lys Ala Leu Ser Ser Asp Lys Ile Val Glu Pro Lys Arg
    290                 295                 300

Gly Pro Leu Ile Pro Gly Met Glu Gly Val Lys Lys Ala Ala Leu Glu
305                 310                 315                 320

Ala Gly Ala Phe Gly Cys Thr Ile Ser Gly Ala Gly Pro Thr Leu Val
                325                 330                 335

Ala Val Thr Asp Gly Glu Glu Arg Gly Arg Glu Ile Gly Glu Arg Met
            340                 345                 350

Val Glu Ala Phe Met Lys Glu Gly Lys Leu Lys Ala Leu Ala Met Val
        355                 360                 365

Lys Gln Leu Asp Arg Val Gly Ala Arg Leu Val Ser Ser Asn Pro Arg
    370                 375                 380

<210> SEQ ID NO 93
<211> LENGTH: 366
<212> TYPE: PRT
<213> ORGANISM: Ipomoea nil

<400> SEQUENCE: 93

Ala Ser Ile Ser Ser Thr Arg His Pro Asn Pro Pro Leu Cys Leu Pro
1               5                   10                  15

Ala Leu Asn Ile Ser Arg Cys Gly Pro Leu Phe Ser Ala Val Thr Ser
            20                  25                  30

Ser Thr Leu Ala Val Ser Asp Pro Glu Pro Val Tyr Ala Ser Val Lys
        35                  40                  45

Ser Phe Ala Pro Ala Thr Val Ala Asn Leu Gly Pro Gly Phe Asp Phe
    50                  55                  60

Leu Gly Cys Ala Val Asp Gly Ile Gly Asp Phe Val Thr Val Arg Val
65                  70                  75                  80

Asp Pro Asp Val Pro Pro Gly Gln Val Ser Ile Ser Glu Ile Ser Gly
                85                  90                  95

Ala Gly Asn Lys Leu Ser Lys Asn Pro Leu Trp Asn Cys Ala Gly Ile
            100                 105                 110

Ala Ala Ile Ala Val Met Lys Met Leu Arg Ile Gln Ser Val Gly Leu
        115                 120                 125

Ser Leu Ser Leu Glu Lys Gly Leu Pro Leu Gly Ser Gly Leu Gly Ser
    130                 135                 140

Ser Ala Ala Ser Ala Ala Ala Ala Val Ala Val Asn Glu Leu Phe
145                 150                 155                 160

Gly Ser Arg Leu Ser Val Ser Asp Leu Val Phe Ala Gly Leu Glu Ser
                165                 170                 175

Glu Ser Lys Val Ser Gly Tyr His Ala Asp Asn Val Ala Pro Ser Ile
            180                 185                 190
```

Met Gly Gly Phe Val Leu Ile Arg Ser Tyr Asp Pro Leu Glu Leu Ile
            195                 200                 205

Gln Leu Lys Phe Pro Gln Glu Lys Ser Leu Phe Phe Val Leu Val Asn
        210                 215                 220

Pro Glu Phe Glu Ala Pro Thr Lys Lys Met Arg Ala Ala Leu Pro Ala
225                 230                 235                 240

Glu Ile Thr Met Ser Ser His Val Trp Asn Cys Ser Gln Ala Gly Ala
                245                 250                 255

Leu Val Ala Ser Val Leu Gln Gly Asp Leu Pro Gly Leu Gly Lys Ala
            260                 265                 270

Leu Ser Ser Asp Lys Ile Val Glu Pro Arg Arg Ala Pro Leu Ile Pro
        275                 280                 285

Gly Met Glu Ala Val Lys Lys Ala Ala Ile Gln Ala Gly Ala Phe Gly
    290                 295                 300

Cys Thr Ile Ser Gly Ala Gly Pro Thr Ala Val Ala Val Thr Asp Asp
305                 310                 315                 320

Glu Glu Lys Gly Met Glu Ile Gly Lys Arg Met Val Glu Ala Phe Ile
                325                 330                 335

Gln Glu Gly Asn Leu Lys Ala Leu Ala Met Val Lys Arg Leu Asp Arg
            340                 345                 350

Val Gly Ala Arg Leu Val Ser Lys Asn Gly Ser Ile Cys Asn
        355                 360                 365

<210> SEQ ID NO 94
<211> LENGTH: 360
<212> TYPE: PRT
<213> ORGANISM: Glycine max

<400> SEQUENCE: 94

Met Ala Thr Ser Thr Cys Phe Leu Cys Pro Ser Thr Ala Ser Leu Lys
1               5                   10                  15

Gly Arg Ala Arg Phe Arg Ile Arg Ile Arg Cys Ser Ser Ser Val Ser
            20                  25                  30

Val Asn Ile Arg Arg Glu Pro Glu Pro Val Thr Thr Leu Val Lys Ala
        35                  40                  45

Phe Ala Pro Ala Thr Val Ala Asn Leu Gly Pro Gly Phe Asp Phe Leu
    50                  55                  60

Gly Cys Ala Val Asp Gly Leu Gly Asp Ile Val Ser Val Lys Val Asp
65                  70                  75                  80

Pro Gln Val His Pro Gly Glu Ile Cys Ile Ser Asp Ile Ser Gly His
                85                  90                  95

Ala Pro Asn Lys Leu Ser Lys Asn Pro Leu Trp Asn Cys Ala Gly Ile
            100                 105                 110

Ala Ala Ile Glu Val Met Lys Met Leu Ser Ile Arg Ser Val Gly Leu
        115                 120                 125

Ser Leu Ser Leu Glu Lys Gly Leu Pro Leu Gly Ser Gly Leu Gly Ser
    130                 135                 140

Ser Ala Ala Ser Ala Ala Ala Ala Val Ala Val Asn Glu Leu Phe
145                 150                 155                 160

Gly Lys Lys Leu Ser Val Glu Glu Leu Val Leu Ala Ser Leu Lys Ser
                165                 170                 175

Glu Glu Lys Val Ser Gly Tyr His Ala Asp Asn Val Ala Pro Ser Ile
            180                 185                 190

Met Gly Gly Phe Val Leu Ile Gly Ser Tyr Ser Pro Leu Glu Leu Met

```
                195                 200                 205
Pro Leu Lys Phe Pro Ala Glu Lys Glu Leu Tyr Phe Val Leu Val Thr
    210                 215                 220

Pro Glu Ile Glu Ala Pro Thr Lys Lys Met Arg Ala Ala Leu Pro Thr
225                 230                 235                 240

Glu Ile Gly Met Pro His His Val Trp Asn Cys Ser Gln Ala Gly Ala
                245                 250                 255

Leu Val Ala Ser Val Leu Gln Gly Asp Val Val Gly Leu Gly Lys Ala
            260                 265                 270

Leu Ser Ser Asp Lys Ile Val Glu Pro Arg Arg Ala Pro Leu Ile Pro
        275                 280                 285

Gly Met Glu Ala Val Lys Arg Ala Ala Ile Gln Ala Gly Ala Leu Gly
    290                 295                 300

Cys Thr Ile Ser Gly Ala Gly Pro Thr Ala Val Ala Val Ile Asp Asp
305                 310                 315                 320

Glu Gln Thr Gly His Leu Ile Ala Lys His Met Ile Asp Ala Phe Leu
                325                 330                 335

His Val Gly Asn Leu Lys Ala Ser Ala Asn Val Lys Gln Leu Asp Arg
            340                 345                 350

Leu Gly Ala Arg Arg Ile Pro Asn
        355                 360

<210> SEQ ID NO 95
<211> LENGTH: 364
<212> TYPE: PRT
<213> ORGANISM: Phaseolus vulgaris

<400> SEQUENCE: 95

Met Ala Thr Ala Met Ser Phe Leu Cys Pro Ser Pro Ala Thr Phe Lys
1               5                   10                  15

Gly Thr Glu Met Pro Ile Ala Arg Phe Arg Cys Cys Ser Ser Asn Thr
            20                  25                  30

Asn Ser Val Ser Leu Asn Thr Arg Thr Glu Pro Gln Pro Val Thr Thr
        35                  40                  45

Phe Val Lys Ala Phe Ala Pro Thr Val Ala Asn Leu Gly Pro Gly
    50                  55                  60

Phe Asp Phe Leu Gly Cys Ala Val Asp Gly Ile Gly Asp Ile Val Ser
65                  70                  75                  80

Val Arg Val Asp Pro Glu Val Arg Pro Gly Glu Ile Arg Ile Ser Asp
                85                  90                  95

Ile Thr Gly His Ala Pro Asn Lys Leu Ser Thr Asn Pro Leu Trp Asn
            100                 105                 110

Cys Ala Gly Ile Ala Ala Ile Glu Val Met Lys Met Leu Ala Ile Arg
        115                 120                 125

Ser Val Gly Leu Ser Leu Ser Leu Gln Lys Gly Leu Pro Leu Gly Ser
    130                 135                 140

Gly Leu Gly Ser Ser Ala Ala Ser Ala Ala Ala Val Ala Val
145                 150                 155                 160

Asn Glu Met Phe Gly Lys Arg Leu Ser Val Glu Asp Leu Val Val Ala
                165                 170                 175

Ser Leu Lys Ser Glu Glu Lys Val Ser Gly Tyr His Ala Asp Asn Val
            180                 185                 190

Ala Pro Ala Ile Met Gly Gly Phe Val Leu Ile Gln Ser Tyr Glu Pro
        195                 200                 205
```

```
Leu Arg Leu Ile Glu Leu Lys Phe Pro Ala Glu Lys Glu Leu Tyr Phe
    210                 215                 220

Val Leu Val Ser Pro Glu Phe Glu Ala Pro Thr Lys Lys Met Arg Ala
225                 230                 235                 240

Ala Leu Pro Gly Glu Ile Ala Met Ala His His Val Trp Asn Cys Ser
                245                 250                 255

Gln Ala Gly Ala Leu Val Ala Ala Val Leu Gln Gly Asp Val Val Gly
            260                 265                 270

Leu Gly Lys Ala Leu Ser Ser Asp Lys Ile Val Glu Pro Arg Arg Ala
        275                 280                 285

Pro Leu Ile Pro Gly Met Glu Ala Val Lys Lys Ala Leu Gln Ala
290                 295                 300

Gly Ala Phe Gly Cys Thr Ile Ser Gly Ala Gly Pro Thr Ala Val Ala
305                 310                 315                 320

Val Ile Asp Asp Glu Leu Ala Gly Asn Ala Ile Ala Glu His Met Ile
                325                 330                 335

His Ala Phe Leu His His Gly Asn Leu Lys Ala Ser Ala Lys Val Leu
            340                 345                 350

Gln Leu Asp Arg Leu Gly Ala Arg Arg Ile Leu Asp
        355                 360

<210> SEQ ID NO 96
<211> LENGTH: 381
<212> TYPE: PRT
<213> ORGANISM: Pinus taeda

<400> SEQUENCE: 96

Met Glu Ser Val Phe Ala Gln Thr Lys Asn His Cys Phe Tyr Leu Glu
1               5                   10                  15

Pro Asp Leu Gly Leu Ile Asn Ser Cys Phe Gly Leu Ser Arg Phe Arg
            20                  25                  30

Thr Lys Phe Ser Arg Gly His Leu Pro His Val Phe Asn Val Arg Cys
        35                  40                  45

Asn Ala Gln Gln Val Ser Leu Lys Pro Val Ile Gln Phe Glu Ala Thr
    50                  55                  60

Pro Ile Leu Gln Ser Val Lys Ala Phe Ala Pro Ala Thr Ile Ala Asn
65                  70                  75                  80

Leu Gly Pro Gly Phe Asp Phe Leu Gly Cys Ala Val Glu Gly Leu Gly
                85                  90                  95

Asp His Val Thr Val Glu Val Asn Glu Asp Val Glu Pro Gly Lys Ile
            100                 105                 110

Val Ile Ser Phe Ile Asp Gly Asp Asn Asn Arg Leu Ser Leu Asn Pro
        115                 120                 125

Met Lys Asn Cys Ala Gly Ile Ala Ala Lys Ala Thr Met Glu Leu Leu
    130                 135                 140

Gly Val Arg Ser Val Gly Leu Ser Leu Gly Leu His Lys Gly Leu Pro
145                 150                 155                 160

Leu Gly Ser Gly Leu Gly Ser Ser Ala Ala Ser Ala Ala Ala Ala
                165                 170                 175

Val Ala Val Asn Gly Leu Phe Gly Asn Lys Leu Thr Lys Ser Asp Leu
            180                 185                 190

Val Leu Ala Gly Leu Glu Ser Glu Ala Val Ser Gly Tyr His Ala
        195                 200                 205

Asp Asn Val Ala Pro Ser Leu Met Gly Gly Phe Val Leu Val Arg Ser
    210                 215                 220
```

```
Tyr Ser Pro Leu Asp Leu Ile His Leu Pro Phe Pro Ser Glu Lys Glu
225                 230                 235                 240

Leu Phe Phe Val Leu Val Thr Pro Ala Phe Glu Ala Pro Thr Lys Glu
                245                 250                 255

Met Arg Ala Val Leu Pro Lys Asn Ile Thr Met Lys Asp His Ile Gln
            260                 265                 270

Asn Cys Ser Gln Ala Ala Ala Leu Val Ala Ala Ile Leu Gln Gly Asp
        275                 280                 285

Pro Cys Leu Leu Gly Ala Ala Leu Ser Ser Asp Ser Ile Val Glu Pro
    290                 295                 300

Lys Arg Gly Pro Phe Ile Pro Gly Met Met Ala Val Lys Ala Ala Ala
305                 310                 315                 320

Leu Glu Thr Gly Ala Phe Gly Cys Thr Ile Ser Gly Ala Gly Pro Thr
                325                 330                 335

Ala Val Ala Ile Thr Asp Thr Ala Glu Lys Gly Lys Ala Ile Ala Val
            340                 345                 350

Ala Met Val Asp Met Phe Gln Lys Gly Gln Leu Glu Ala Thr Ala
        355                 360                 365

Ser Val Gln Lys Leu Asp Arg Ile Gly Ala Arg Val Val
    370                 375                 380

<210> SEQ ID NO 97
<211> LENGTH: 380
<212> TYPE: PRT
<213> ORGANISM: Zea mays

<400> SEQUENCE: 97

Met Ala Pro Ala Ala Thr Ser Thr Ala Ser Ala Pro Ser Ser Phe His
1               5                   10                  15

Ser Thr Gly Arg His Arg Ala Arg Val Gly Ala Arg Pro Ser Leu Val
            20                  25                  30

Ser Leu Arg Val Arg Ala Ala Asn Pro Asn Val Thr Ala Asp Pro Ala
        35                  40                  45

Pro Ala Phe Gln Ser Val Thr Thr Phe Ala Pro Ala Thr Val Ala Asn
    50                  55                  60

Leu Gly Pro Gly Phe Asp Phe Leu Gly Cys Ala Val Ala Asp Ala Ser
65                  70                  75                  80

Leu Ser Leu Gly Asp Thr Val Thr Ala Thr Leu Asp Pro Ser Leu Pro
                85                  90                  95

Pro Ala Thr Val Ser Ile Ala Ser Val Thr Ser Pro Ser Arg Pro Asn
            100                 105                 110

Leu Ala Glu Arg Leu Ser Arg Asp Pro Leu Arg Asn Cys Ala Gly Val
        115                 120                 125

Ala Ala Ile Ala Ala Leu Arg Ala Leu Gly Val Arg Ser His Ala Val
    130                 135                 140

Ser Ile His Leu Thr Lys Gly Leu Pro Leu Gly Ser Gly Leu Gly Ser
145                 150                 155                 160

Ser Ala Ala Ser Ala Ala Ala Ala Lys Ala Val Asp Ala Leu Phe
                165                 170                 175

Gly Ser Arg Leu Gly Arg Asp Asp Leu Val Leu Ala Gly Leu Glu Ser
            180                 185                 190

Glu Lys Ala Val Ser Gly Phe His Ala Asp Asn Ile Ala Pro Ala Ile
        195                 200                 205

Leu Gly Gly Phe Val Leu Val Arg Ser Tyr Asp Pro Phe His Leu Val
```

```
                210               215               220
Pro Leu Ser Phe Pro Ala Leu Arg Leu His Phe Val Leu Val Thr
225               230               235               240

Pro Asp Phe Glu Ala Pro Thr Ser Lys Met Arg Ala Ala Leu Pro Arg
                245               250               255

Gln Val Asp Val Gln His Val Arg Asn Ser Ser Gln Ala Ala Ala
            260               265               270

Leu Val Ala Ala Val Leu Gln Gly Asp Ala Gly Leu Ile Gly Ser Ala
            275               280               285

Met Ser Ser Asp Gly Ile Val Glu Pro Thr Arg Ala Pro Leu Ile Pro
290               295               300

Gly Met Ala Ala Val Lys Ala Ala Leu Gln Ala Gly Ala Leu Gly
305               310               315               320

Cys Thr Ile Ser Gly Ala Gly Pro Thr Val Ala Val Ile Gln Gly
                325               330               335

Glu Glu Arg Gly Glu Glu Val Ala Arg Lys Met Val Asp Ala Phe Trp
                340               345               350

Ser Ala Gly Lys Leu Lys Ala Thr Ala Thr Val Ala Gln Leu Asp Thr
            355               360               365

Leu Gly Ala Arg Val Ile Ala Thr Ser Ser Leu Asn
370               375               380

<210> SEQ ID NO 98
<211> LENGTH: 378
<212> TYPE: PRT
<213> ORGANISM: Oryza sativa

<400> SEQUENCE: 98

Met Ala Ala Ala Ala Ala Ala Ala Pro Ser Pro Ala Pro Cys
1               5               10              15

Phe Pro Ser Thr Arg His Thr Leu Pro Gly Leu Val Ser Val Arg Val
                20              25              30

Ser Arg Arg Val Lys Val Ala Val Ala Ile Ala Asp Pro Ala Pro Ala
            35              40              45

Phe Asn Ser Val Thr Ala Phe Ala Pro Ala Thr Val Ala Asn Leu Gly
        50              55              60

Pro Gly Phe Asp Phe Leu Gly Cys Ala Val Ala Asp Ala Ser Leu Ser
65              70              75              80

Leu Gly Asp Thr Val Thr Ala Thr Leu Asp Pro Ser Leu Pro Pro Gly
                85              90              95

Thr Val Ala Ile Ala Ser Val Thr Ser Pro Ser Arg Pro Thr Leu Ala
                100             105             110

Asp Arg Leu Ser Arg Asp Pro Leu Arg Asn Cys Ala Gly Val Ala Ala
            115             120             125

Ile Ala Ala Leu Arg Ala Leu Asp Val Lys Ser His Ala Val Ser Ile
130             135             140

His Leu Thr Lys Gly Leu Pro Leu Gly Ser Gly Leu Gly Ser Ser Ala
145             150             155             160

Ala Ser Ala Ala Ala Ala Lys Ala Val Asp Ala Leu Phe Gly Ser
            165             170             175

Leu Leu His Gln Asp Asp Leu Val Leu Ala Gly Leu Glu Ser Glu Lys
            180             185             190

Ala Val Ser Gly Phe His Ala Asp Asn Ile Ala Pro Ala Ile Leu Gly
            195             200             205
```

```
Gly Phe Val Leu Val Arg Ser Tyr Asp Pro Phe His Leu Ile Pro Leu
    210                 215                 220

Ser Ser Pro Pro Ala Leu Arg Leu His Phe Val Leu Val Thr Pro Asp
225                 230                 235                 240

Phe Glu Ala Pro Thr Ser Lys Met Arg Ala Ala Leu Pro Lys Gln Val
                245                 250                 255

Ala Val His Gln His Val Arg Asn Ser Ser Gln Ala Ala Leu Val
                260                 265                 270

Ala Ala Val Leu Gln Gly Asp Ala Thr Leu Ile Gly Ser Ala Met Ser
            275                 280                 285

Ser Asp Gly Ile Val Glu Pro Thr Arg Ala Pro Leu Ile Pro Gly Met
    290                 295                 300

Ala Ala Val Lys Ala Ala Ala Leu Glu Ala Gly Ala Leu Gly Cys Thr
305                 310                 315                 320

Ile Ser Gly Ala Gly Pro Thr Ala Val Ala Val Ile Asp Gly Glu Glu
                325                 330                 335

Lys Gly Glu Glu Val Gly Arg Arg Met Val Glu Ala Phe Ala Asn Ala
            340                 345                 350

Gly Asn Leu Lys Ala Thr Ala Thr Val Ala Gln Leu Asp Arg Val Gly
    355                 360                 365

Ala Arg Val Ile Ser Thr Ser Thr Leu Glu
370                 375

<210> SEQ ID NO 99
<211> LENGTH: 1225
<212> TYPE: DNA
<213> ORGANISM: Arabidopsis thaliana

<400> SEQUENCE: 99
ctcattactt gttcatcaat ggcaagtctt tgtttccaat ctccttccaa acccatttcc      60
tatttccaac ccaaatccaa tccatcgcca ccgttattcg ccaaagtctc cgtctttcga     120
tgcagagctt ccgtacaaac cctcgtcgcc gttgagccgg agccagtttt cgtctccgtc     180
aagactttttg cgccagccac cgtcgctaat ttgggaccag ggtttgattt cttaggatgt     240
gccgtcgatg gtctcggaga ccatgtgact ctccgtgtag atccctctgt acgagccgga     300
gaggtctcaa tctcggagat caccggaacc acaacaaaac tcagcacgaa ccctctccgg     360
aactgcgccg gaatcgctgc tattgctacg atgaagatgt tagggatcag atcggttggt     420
ttatcattag atttgcataa aggtcttcct ttaggtagcg gtttaggttc tagtgcagct     480
agtgccgccg cagctgctgt ggcggttaat gagatctttg gccggaaatt agggagtgat     540
caattggtat tagccggttt agaatcggaa gcgaaagtct ccggttatca cgctgataat     600
atcgcaccag cgatcatggg tggattcgtt ttgattagaa actacgaacc acttgatttg     660
aaaccattga ggttcccatc tgataaagat ctcttctttg ttctagtaag ccctgacttt     720
gaagctccaa ctaagaaaat gagagctgca ttgcctacag agattccaat ggttcatcat     780
gtttggaaca gtagccaagc agctgcttta gtcgctgctg tgttagaagg tgacgcagtg     840
atgcttggga aggcattgtc gtcggataag attgtggagc cgactagagc gccgttgatt     900
ccgggaatgg aagctgtgaa gaaggcggct ttagaagctg gagcatttgg atgtactatt     960
agcggagctg gaccaacagc ggttgcggtg attgattcgg aggagaaggg tcaagtcatt    1020
ggagagaaga tggtggaagc gttttggaaa gttggtcatt tgaaatctgt tgcttctgtg    1080
aagaagcttg ataatgttgg tgctaggctt gtcaacagcg tctccagatg atctttgtgt    1140
```

```
gctgtttgat tatgctaaga ttggaacaaa tcttcctttg tactgtaatt tctagatgat    1200
aataaagttg tttgttttct acact                                          1225
```

<210> SEQ ID NO 100
<211> LENGTH: 370
<212> TYPE: PRT
<213> ORGANISM: Arabidopsis thaliana

<400> SEQUENCE: 100

```
Met Ala Ser Leu Cys Phe Gln Ser Pro Ser Lys Pro Ile Ser Tyr Phe
1               5                   10                  15

Gln Pro Lys Ser Asn Pro Ser Pro Leu Phe Ala Lys Val Ser Val
            20                  25                  30

Phe Arg Cys Arg Ala Ser Val Gln Thr Leu Val Ala Val Glu Pro Glu
        35                  40                  45

Pro Val Phe Val Ser Val Lys Thr Phe Ala Pro Ala Thr Val Ala Asn
    50                  55                  60

Leu Gly Pro Gly Phe Asp Phe Leu Gly Cys Ala Val Asp Gly Leu Gly
65                  70                  75                  80

Asp His Val Thr Leu Arg Val Asp Pro Ser Val Arg Ala Gly Glu Val
                85                  90                  95

Ser Ile Ser Glu Ile Thr Gly Thr Thr Thr Lys Leu Ser Thr Asn Pro
            100                 105                 110

Leu Arg Asn Cys Ala Gly Ile Ala Ala Ile Ala Thr Met Lys Met Leu
        115                 120                 125

Gly Ile Arg Ser Val Gly Leu Ser Leu Asp Leu His Lys Gly Leu Pro
    130                 135                 140

Leu Gly Ser Gly Leu Gly Ser Ser Ala Ala Ser Ala Ala Ala Ala Ala
145                 150                 155                 160

Val Ala Val Asn Glu Ile Phe Gly Arg Lys Leu Gly Ser Asp Gln Leu
                165                 170                 175

Val Leu Ala Gly Leu Glu Ser Glu Ala Lys Val Ser Gly Tyr His Ala
            180                 185                 190

Asp Asn Ile Ala Pro Ala Ile Met Gly Gly Phe Val Leu Ile Arg Asn
        195                 200                 205

Tyr Glu Pro Leu Asp Leu Lys Pro Leu Arg Phe Pro Ser Asp Lys Asp
    210                 215                 220

Leu Phe Phe Val Leu Val Ser Pro Asp Phe Glu Ala Pro Thr Lys Lys
225                 230                 235                 240

Met Arg Ala Ala Leu Pro Thr Glu Ile Pro Met Val His His Val Trp
                245                 250                 255

Asn Ser Ser Gln Ala Ala Ala Leu Val Ala Ala Val Leu Glu Gly Asp
            260                 265                 270

Ala Val Met Leu Gly Lys Ala Leu Ser Ser Asp Lys Ile Val Glu Pro
        275                 280                 285

Thr Arg Ala Pro Leu Ile Pro Gly Met Glu Ala Val Lys Lys Ala Ala
    290                 295                 300

Leu Glu Ala Gly Ala Phe Gly Cys Thr Ile Ser Gly Ala Gly Pro Thr
305                 310                 315                 320

Ala Val Ala Val Ile Asp Ser Glu Glu Lys Gly Gln Val Ile Gly Glu
                325                 330                 335

Lys Met Val Glu Ala Phe Trp Lys Val Gly His Leu Lys Ser Val Ala
            340                 345                 350

Ser Val Lys Lys Leu Asp Asn Val Gly Ala Arg Leu Val Asn Ser Val
```

Ser Arg
    370

<210> SEQ ID NO 101
<211> LENGTH: 1128
<212> TYPE: DNA
<213> ORGANISM: Lactuca sativa

<400> SEQUENCE: 101

| | | | | | |
|---|---|---|---|---|---|
| atggcaattc | gccattatca | acctccattc | gcctccactt | cttcttctat | ctctagtaca | 60 |
| gatttattca | aacccctaa | actttatctt | tcatcgtctg | tccggtgcaa | catctccgtc | 120 |
| gcttccaaac | tggaacccga | acctcatcca | gttttcacct | ccgttaagtc | attcgccccc | 180 |
| gccaccgtag | ccaacctcgg | gcctggtttc | gacttcctcg | gctgcgcaat | cgacggcatc | 240 |
| ggagattacg | ttaccctcac | agtcgacccc | caagtccaac | ccggcagatt | atcaattgca | 300 |
| gaaatcaacg | gcgttgacaa | gtcttccaag | aggctcagca | gaaaccctct | atggaattgc | 360 |
| gccggaattg | ctgcaatctc | cgtcatgaag | atgctcaaga | tccgatccgt | tggtctctct | 420 |
| ttatccatca | atacatgtct | ccccttcga | ggcggcctag | gctccagcgc | cgctagcgct | 480 |
| gccgccgccg | ccgttgcggt | taatgagatt | tccgaggga | agttacatga | ttccgatttg | 540 |
| atactcgcgg | ggctcgaagc | tgaagcgaag | ttatccggtt | atcacgccga | taacattgct | 600 |
| ccggcgatca | tgggcgggtt | tgtgttgatc | agaagctacg | atccattaga | gttgatctcc | 660 |
| ttgaagtttc | caccggaaaa | gaatctgttt | tcgtgttgg | tgaatcctga | attccaagca | 720 |
| caaacgaaga | agatgagggc | ggttctaccg | acggagataa | caatgtcgga | tcatgtatgg | 780 |
| aattgtagtc | aggcggcggc | gttggtggca | ggcgtattgc | aggggatt | ggtgggttt | 840 |
| gggaaggcat | tgtcatcgga | tagaatagtg | gagccacggc | gggcgccatt | gcttccggga | 900 |
| atggaagatg | tgaagaaggc | agcaatgaa | gcagggcat | atgggtgtac | gataagtggg | 960 |
| tcagggccga | cggtggtggc | ggtgacggat | gatgaagata | gagggaggga | gatcggggag | 1020 |
| aagatggtgg | aagctttgt | agagaaggga | aagttgaaag | ctttggctat | ggtgaagaaa | 1080 |
| ctggacagag | ttggtgctag | agttatcagt | cgtatctcca | gccaatga | | 1128 |

<210> SEQ ID NO 102
<211> LENGTH: 375
<212> TYPE: PRT
<213> ORGANISM: Lactuca sativa

<400> SEQUENCE: 102

Met Ala Ile Arg His Tyr Gln Pro Pro Phe Ala Ser Thr Ser Ser Ser
1               5                   10                  15

Ile Ser Ser Thr Asp Leu Phe Lys Pro Lys Leu Tyr Leu Ser Ser
            20                  25                  30

Ser Val Arg Cys Asn Ile Ser Val Ala Ser Lys Leu Glu Pro Glu Pro
        35                  40                  45

His Pro Val Phe Thr Ser Val Lys Ser Phe Ala Pro Ala Thr Val Ala
    50                  55                  60

Asn Leu Gly Pro Gly Phe Asp Phe Leu Gly Cys Ala Ile Asp Gly Ile
65                  70                  75                  80

Gly Asp Tyr Val Thr Leu Thr Val Asp Pro Gln Val Gln Pro Gly Arg
                85                  90                  95

Leu Ser Ile Ala Glu Ile Asn Gly Val Asp Lys Ser Ser Lys Arg Leu
            100                 105                 110

```
Ser Arg Asn Pro Leu Trp Asn Cys Ala Gly Ile Ala Ala Ile Ser Val
        115                 120                 125
Met Lys Met Leu Lys Ile Arg Ser Val Gly Leu Ser Leu Ser Ile Asn
    130                 135                 140
Thr Cys Leu Pro Leu Arg Gly Gly Leu Gly Ser Ser Ala Ala Ser Ala
145                 150                 155                 160
Ala Ala Ala Ala Val Ala Val Asn Glu Ile Phe Gly Gly Lys Leu His
                165                 170                 175
Asp Ser Asp Leu Ile Leu Ala Gly Leu Glu Ala Glu Ala Lys Leu Ser
            180                 185                 190
Gly Tyr His Ala Asp Asn Ile Ala Pro Ala Ile Met Gly Gly Phe Val
        195                 200                 205
Leu Ile Arg Ser Tyr Asp Pro Leu Glu Leu Ile Ser Leu Lys Phe Pro
    210                 215                 220
Pro Glu Lys Asn Leu Phe Phe Val Leu Val Asn Pro Glu Phe Gln Ala
225                 230                 235                 240
Gln Thr Lys Lys Met Arg Ala Val Leu Pro Thr Glu Ile Thr Met Ser
                245                 250                 255
Asp His Val Trp Asn Cys Ser Gln Ala Ala Ala Leu Val Ala Gly Val
            260                 265                 270
Leu Gln Gly Asp Leu Val Gly Phe Gly Lys Ala Leu Ser Ser Asp Arg
        275                 280                 285
Ile Val Glu Pro Arg Arg Ala Pro Leu Leu Pro Gly Met Glu Asp Val
    290                 295                 300
Lys Lys Ala Ala Met Glu Ala Gly Ala Tyr Gly Cys Thr Ile Ser Gly
305                 310                 315                 320
Ser Gly Pro Thr Val Val Ala Val Thr Asp Asp Glu Asp Arg Gly Arg
                325                 330                 335
Glu Ile Gly Glu Lys Met Val Glu Ala Phe Val Glu Lys Gly Lys Leu
            340                 345                 350
Lys Ala Leu Ala Met Val Lys Lys Leu Asp Arg Val Gly Ala Arg Val
        355                 360                 365
Ile Ser Arg Ile Ser Ser Gln
    370                 375

<210> SEQ ID NO 103
<211> LENGTH: 1106
<212> TYPE: DNA
<213> ORGANISM: Vitis vinifera

<400> SEQUENCE: 103
atggcgattt gcttccactc cccctcaaaa cccacttgca tttctccctc atcaaaccat      60
tacagaccca atcttcatgc tcggtccttc agatgcaact tctctaaaac attaactgct     120
gatcctcaac cagttttcac ctctgtgaag tccttcgcac ccgcaaccgt tgctaacctc     180
ggtcccggtt tcgatttcct cggtgctgct gttgatggta taggcgattt cgtctccctt     240
cgcgtggatc ctgatgttcg gcccggggag atttcgattg tcgatatcga tggtgttggg     300
aatagcgcca gaagctcag taaaaatccc tctggaact cgccggcat tgccgctatc       360 tccgtcatga aaatgctcgg agtccgatcg gtggggctgt cccttttcct cgagaagggg     420
ttgccattgg aagtggact tgggtcgagc gctgccagtg ccgccgcggc tgctgtggcg     480
gtgaatgaga ttttgggcg gaaattggga gttgatgacc ttgtccttgc tgggcttgac     540
tcggaagcta agtttcggg ttatcacgcg aacaatgtgg cgccggctct tatgggagga     600
```

```
ttcgtgttga ttcggagtta tgatcctttg gagttgattc ctttgacgtt tccgagcgac    660
aaggagttgt tttttgtgtt ggtgaatccg gaatttgaag ctcccaccaa gaaaatgcgg    720
gcggcattgc cgtcggagat cgggatgtct gatcacgtgt ggaattgtag ccaggccgct    780
gcattggtag cctcgatttt gcaaggagat tgagggggtt gggcaaggca ttgtcctccg    840
acagaattgt ggagccaagg agggcaccct tgatccctgg gatggaagga gtgaaaaagg    900
ctgctcttga ggctggtgca tttggctgta caattagtgg agcagggccg actgcagttg    960
caattacaga tgacgaagag aagggaaggg agattggaga acggatggta gaagctttct   1020
tggaggaagg gaagttgaag gctgtagcaa tggtgaagca actcgatagg gttggtgcta   1080
ggcttatgag tagcatcctc agatga                                        1106
```

<210> SEQ ID NO 104
<211> LENGTH: 368
<212> TYPE: PRT
<213> ORGANISM: Vitis vinifera

<400> SEQUENCE: 104

```
Met Ala Ile Cys Phe His Ser Pro Ser Lys Pro Thr Cys Ile Ser Pro
1               5                   10                  15

Ser Ser Asn His Tyr Arg Pro Asn Leu His Ala Arg Ser Phe Arg Cys
            20                  25                  30

Asn Phe Ser Lys Thr Leu Thr Ala Asp Pro Gln Pro Val Phe Thr Ser
        35                  40                  45

Val Lys Ser Phe Ala Pro Ala Thr Val Ala Asn Leu Gly Pro Gly Phe
    50                  55                  60

Asp Phe Leu Gly Ala Ala Val Asp Gly Ile Gly Asp Phe Val Ser Leu
65                  70                  75                  80

Arg Val Asp Pro Asp Val Arg Pro Gly Glu Ile Ser Ile Val Asp Ile
                85                  90                  95

Asp Gly Val Gly Asn Ser Ala Lys Lys Leu Ser Lys Asn Pro Leu Trp
            100                 105                 110

Asn Cys Ala Gly Leu Ala Ala Ile Ser Val Met Lys Met Leu Gly Val
        115                 120                 125

Arg Ser Val Gly Leu Ser Leu Ser Leu Glu Lys Gly Leu Pro Leu Gly
    130                 135                 140

Ser Gly Leu Gly Ser Ser Ala Ala Ser Ala Ala Ala Ala Val Ala
145                 150                 155                 160

Val Asn Glu Ile Phe Gly Arg Lys Leu Gly Val Asp Asp Leu Val Leu
                165                 170                 175

Ala Gly Leu Asp Ser Glu Ala Lys Val Ser Gly Tyr His Ala Asn Asn
            180                 185                 190

Val Ala Pro Ala Leu Met Gly Gly Phe Val Leu Ile Arg Ser Tyr Asp
        195                 200                 205

Pro Leu Glu Leu Ile Pro Leu Thr Phe Pro Ser Asp Lys Glu Leu Phe
    210                 215                 220

Phe Val Leu Val Asn Pro Glu Phe Glu Ala Pro Thr Lys Lys Met Arg
225                 230                 235                 240

Ala Ala Leu Pro Ser Glu Ile Gly Met Ser Asp His Val Trp Asn Cys
                245                 250                 255

Ser Gln Ala Ala Ala Leu Val Ala Ser Ile Leu Gln Gly Asp Leu Arg
            260                 265                 270

Gly Leu Gly Lys Ala Leu Ser Ser Asp Arg Ile Val Glu Pro Arg Arg
```

|                              |                              | 275                          |                              |                              | 280                          |                              |                              | 285                          |                              |
|------------------------------|------------------------------|------------------------------|------------------------------|------------------------------|------------------------------|------------------------------|------------------------------|------------------------------|------------------------------|

Ala Pro Leu Ile Pro Gly Met Glu Gly Val Lys Lys Ala Ala Leu Glu
    290              295              300

Ala Gly Ala Phe Gly Cys Thr Ile Ser Gly Ala Gly Pro Thr Ala Val
305              310              315              320

Ala Ile Thr Asp Asp Glu Glu Lys Gly Arg Glu Ile Gly Glu Arg Met
        325              330              335

Val Glu Ala Phe Leu Glu Glu Gly Lys Leu Lys Ala Val Ala Met Val
        340              345              350

Lys Gln Leu Asp Arg Val Gly Ala Arg Leu Met Ser Ser Ile Leu Arg
        355              360              365

<210> SEQ ID NO 105
<211> LENGTH: 1120
<212> TYPE: DNA
<213> ORGANISM: Cucumis sativus

<400> SEQUENCE: 105

| atggctatgc tctcctatca accgccattg aagtcgttga ccattcctcc agtttcttta | 60 |
|---|---|
| tctaaccctc aacctgttct cttcaggtgc agtttgtctc ttccatctag aaccgccgtc | 120 |
| acttccgtcg aacctcaacc cgttttctct tccgtcaagg cgtttgctcc tgcaaccgtc | 180 |
| gctaatttag gtcctgggtt tgatttcctt ggctgcgctg ttgatggctt gggagattat | 240 |
| gtctctctta gtgttgattc caatgttcat ccaggtgaag ttgcgatttc tgatattaca | 300 |
| gggaataaca cgaataaact tagtaaaaat cctctctata attgtgctgg tattgctgct | 360 |
| attgaagtta tgaaaatgct agggatccga tctgttggtc tttctctttc gcttgagaaa | 420 |
| ggtttgccgt tagggagtgg attgggatct agtgctgcga gtgcagctgc tgcggcgatt | 480 |
| gctgttaatg gattgttcgg tgggaaatta ggagtagagg aattggttct cgcggggttg | 540 |
| aaatcggaag agaaggtttc tgggtaccat gcggataagt cgcaccggct atcatggggg | 600 |
| gtttcattct gattcgaaat tacgaaccct tggaattgat tcgtttgaaa ttccccgtcg | 660 |
| agaaggagct gttcttcgtg ttggtcagcc cggaattcga agcaccgacg aagaaaatgc | 720 |
| gggctgcgtt acctgctgaa gttgggatgc cacaccatgt gtggaattcc agccaagccg | 780 |
| gggcgttggt ggctgcggtg ctgcagggta cacgatggga ttggggaaag cattgtcatc | 840 |
| agacaaaatt gtggaaccaa ggcgttcgcc gttgattcca ggtatggatg gtgttaagaa | 900 |
| ggcagccatt gctgctgggg catttgggtg cacgataagc ggagcagggc caacagcggt | 960 |
| ggcggtgatc gataacgaag agaaggggaa ggagattggt gagaggatgg ttatggcatt | 1020 |
| tctgaaggaa ggaaatttga aagctacggc atctgtaaag agactagatc gagttggtgc | 1080 |
| aaggcttatt ggatcaactc ctttagatag agttttatga | 1120 |

<210> SEQ ID NO 106
<211> LENGTH: 373
<212> TYPE: PRT
<213> ORGANISM: Cucumis sativus

<400> SEQUENCE: 106

Met Ala Met Leu Ser Tyr Gln Pro Pro Leu Lys Ser Leu Thr Ile Pro
1              5                    10                  15

Pro Val Ser Leu Ser Asn Pro Lys Pro Val Leu Phe Arg Cys Ser Leu
         20               25              30

Ser Leu Pro Ser Arg Thr Ala Val Thr Ser Val Glu Pro Gln Pro Val
        35                40              45

| | | | | | | | | | | | |
|---|---|---|---|---|---|---|---|---|---|---|---|
|Phe|Ser|Ser|Val|Lys|Ala|Phe|Ala|Pro|Ala|Thr|Val|Ala|Asn|Leu|Gly|
| |50| | | |55| | | |60| | | | | | |

Phe Ser Ser Val Lys Ala Phe Ala Pro Ala Thr Val Ala Asn Leu Gly
    50              55              60

Pro Gly Phe Asp Phe Leu Gly Cys Ala Val Asp Gly Leu Gly Asp Tyr
65          70              75              80

Val Ser Leu Ser Val Asp Ser Asn Val His Pro Gly Glu Val Ala Ile
                85              90              95

Ser Asp Ile Thr Gly Asn Asn Thr Asn Lys Leu Ser Lys Asn Pro Leu
            100             105             110

Tyr Asn Cys Ala Gly Ile Ala Ala Ile Glu Val Met Lys Met Leu Gly
        115             120             125

Ile Arg Ser Val Gly Leu Ser Leu Ser Leu Glu Lys Gly Leu Pro Leu
    130             135             140

Gly Ser Gly Leu Gly Ser Ser Ala Ala Ser Ala Ala Ala Ala Ala Ile
145             150             155             160

Ala Val Asn Gly Leu Phe Gly Gly Lys Leu Gly Val Glu Glu Leu Val
                165             170             175

Leu Ala Gly Leu Lys Ser Glu Glu Lys Val Ser Gly Tyr His Ala Asp
            180             185             190

Asn Val Ala Pro Ala Ile Met Gly Gly Phe Ile Leu Ile Arg Asn Tyr
        195             200             205

Glu Pro Leu Glu Leu Ile Arg Leu Lys Phe Pro Val Glu Lys Glu Leu
210             215             220

Phe Phe Val Leu Val Ser Pro Glu Phe Glu Ala Pro Thr Lys Lys Met
225             230             235             240

Arg Ala Ala Leu Pro Ala Glu Val Gly Met Pro His His Val Trp Asn
                245             250             255

Ser Ser Gln Ala Gly Ala Leu Val Ala Ala Val Leu Gln Gly Asp Thr
            260             265             270

Met Gly Leu Gly Lys Ala Leu Ser Ser Asp Lys Ile Val Glu Pro Arg
        275             280             285

Arg Ser Pro Leu Ile Pro Gly Met Asp Gly Val Lys Lys Ala Ala Ile
    290             295             300

Ala Ala Gly Ala Phe Gly Cys Thr Ile Ser Gly Ala Gly Pro Thr Ala
305             310             315             320

Val Ala Val Ile Asp Asn Glu Glu Lys Gly Lys Glu Ile Gly Glu Arg
                325             330             335

Met Val Met Ala Phe Leu Lys Glu Gly Asn Leu Lys Ala Thr Ala Ser
            340             345             350

Val Lys Arg Leu Asp Arg Val Gly Ala Arg Leu Ile Gly Ser Thr Pro
        355             360             365

Leu Asp Arg Val Leu
    370

<210> SEQ ID NO 107
<211> LENGTH: 1113
<212> TYPE: DNA
<213> ORGANISM: Spinacia oleracea

<400> SEQUENCE: 107
atggcaatct gcgcacaatc tccattcaaa cccgtcaatc tatcacctca ctccccttct      60
cccacccaca aatccccatt catctgtaaa ctttctctct cctcccactc aacccactca     120
cctctcacca ctgaaccaac accactcctc acctccgtca ccaccttcgc ccccgctacc     180
gtcgccaacc tcggcccagg gttcgacttc ctcggttgcg ctgtcgatgg cctcggtgac     240

```
ttcgtttctc tttccgttga cccctccgtt catcccggtc aactctccat ctcctccatt      300
tccggcgacg cttcttccaa actctccaaa gatccccttc ttaactgcgc cggtatctct      360
gccctagccg ccatgaagct ccttaacatt cgctccgtcg gcctttctct atctctccaa      420
aaagggctcc cacttggctc cggtctcgga tcttcagcag cttccgctgc tgctgccgct      480
gttgctgtga actccctatt tggctcccct ctctctccac tcgacctcgt acacgctgga      540
cttgagtcag aatctaaagt ttccggttac cacgctgaca acattgcacc ggcgataatg      600
ggtggtttta tcttaatcag gagttatgag ccattggatt tgatgaaatt ggagttccct      660
gagactaatg atttgtattt cgtattggtt agtccggaat ttgaagcccc aacgaagaag      720
atgagggcgg cattgccgaa ggagatcggg atgccgcacc acatatggaa ttctagccaa      780
gcggcagcat tggtggcggc agttttgatg ggtgacgtag aagggatagg aaaggcaatg      840
tcttccgata aagtggtgga gccaaggcgg gcaccattga ttgccgggat gatggcggtg      900
aagaaggcgg ctattgaagg gggagcgttc gggtgtacaa ttagcggggc agggcctacg      960
gctgtggcag taacggatag ggaggagaag ggaagagaga tcggagagag aatggtggaa     1020
gcgttttgga aggaaggagg gttaaaggct gccgctgtga ttcaaaagct agatagagtt     1080
ggtgctagag ttgttagcag tgttcccaga tga                                  1113
```

<210> SEQ ID NO 108
<211> LENGTH: 370
<212> TYPE: PRT
<213> ORGANISM: Spinacia oleracea

<400> SEQUENCE: 108

```
Met Ala Ile Cys Ala Gln Ser Pro Phe Lys Pro Val Asn Leu Ser Pro
1               5                   10                  15

His Ser Pro Ser Pro Thr His Lys Ser Pro Phe Ile Cys Lys Leu Ser
            20                  25                  30

Leu Ser Ser His Ser Thr His Ser Pro Leu Thr Thr Glu Pro Thr Pro
        35                  40                  45

Leu Leu Thr Ser Val Thr Thr Phe Ala Pro Ala Thr Val Ala Asn Leu
    50                  55                  60

Gly Pro Gly Phe Asp Phe Leu Gly Cys Ala Val Asp Gly Leu Gly Asp
65                  70                  75                  80

Phe Val Ser Leu Ser Val Asp Pro Ser Val His Pro Gly Gln Leu Ser
                85                  90                  95

Ile Ser Ser Ile Ser Gly Asp Ala Ser Ser Lys Leu Ser Lys Asp Pro
            100                 105                 110

Leu Leu Asn Cys Ala Gly Ile Ser Ala Leu Ala Met Lys Leu Leu
        115                 120                 125

Asn Ile Arg Ser Val Gly Leu Ser Leu Ser Leu Gln Lys Gly Leu Pro
    130                 135                 140

Leu Gly Ser Gly Leu Gly Ser Ser Ala Ala Ser Ala Ala Ala Ala
145                 150                 155                 160

Val Ala Val Asn Ser Leu Phe Gly Ser Pro Leu Ser Pro Leu Asp Leu
                165                 170                 175

Val His Ala Gly Leu Glu Ser Glu Ser Lys Val Ser Gly Tyr His Ala
            180                 185                 190

Asp Asn Ile Ala Pro Ala Ile Met Gly Gly Phe Ile Leu Ile Arg Ser
        195                 200                 205

Tyr Glu Pro Leu Asp Leu Met Lys Leu Glu Phe Pro Glu Thr Asn Asp
```

```
            210                215                220
Leu Tyr Phe Val Leu Val Ser Pro Glu Phe Glu Ala Pro Thr Lys Lys
225                230                235                240

Met Arg Ala Ala Leu Pro Lys Glu Ile Gly Met Pro His His Ile Trp
            245                250                255

Asn Ser Ser Gln Ala Ala Ala Leu Val Ala Ala Val Leu Met Gly Asp
                260                265                270

Val Glu Gly Ile Gly Lys Ala Met Ser Ser Asp Lys Val Val Glu Pro
            275                280                285

Arg Arg Ala Pro Leu Ile Pro Gly Met Met Ala Val Lys Lys Ala Ala
            290                295                300

Ile Glu Gly Gly Ala Phe Gly Cys Thr Ile Ser Gly Ala Gly Pro Thr
305                310                315                320

Ala Val Ala Val Thr Asp Arg Glu Glu Lys Gly Arg Glu Ile Gly Glu
                325                330                335

Arg Met Val Glu Ala Phe Trp Lys Glu Gly Gly Leu Lys Ala Ala Ala
                340                345                350

Val Ile Gln Lys Leu Asp Arg Val Gly Ala Arg Val Val Ser Ser Val
                355                360                365

Pro Arg
    370

<210> SEQ ID NO 109
<211> LENGTH: 1130
<212> TYPE: DNA
<213> ORGANISM: solanum lycopersicum

<400> SEQUENCE: 109
atggctataa cctttcaatc tcccatgaaa ctcagcttca tcacttctaa tggcttctca      60
aatcctcctt ctctttatcc catcaatacc catttctcat ttggattcaa tctctcatct     120
gtctcctcca aaacccaaac ccatatcacc atacccgaac ccgaaccggt attcacctcc     180
gtcaagtcgt tgctccggc cactgttgct aatctaggtc cgggttttga tttcctcgga      240
tgcgccgttg atggagtcgg agattttgtc actcttcggg ttgacccaaa tgttaaagct     300
ggggagggtt cgatttctga tatctccggt gctggaaata ggcttagtaa agacccttta     360
tcgaactgtg ctggaatagc tgctatttct gttatgaaga tgttgaatat acagtctgtt     420
ggtttatcga tttcgcttga aaaagggttg ccgttgggta gtggacttgg gtctagtgct     480
gctagtgctg cggcggcggc ggtggctgtg aatgagattt ttggacggaa gttgagtgtt     540
gatgatcttg tgcttgctgg gttggaatcg gaaacgaagg tttcgggtta tcatgctgta     600
atatagcacc ttcgattatg ggtggttttg tgttgataag aagttatgat ccgttggaat     660
tgatcccatt gaagtttcca tttgaaaaag atttgttttt tgtgcttgtg aatcccgaat     720
tcgaagctcc aacgaagaag atgagggcgg tattgccatc ggaggtgaca atgtcgcatc     780
atatatggaa ttgtagtcag gctggggcgt tggtggctgc gatattgcag ggggattcga     840
ggggtttagg gaaggcgttg tcgtctgata agattgtgga gccgaggaga gggccgttga     900
ttcctgggat ggagggagtg aagaaggcgc gttgaaggc tggggcattt ggttgcacga     960
taagcggagc tggacctact tggtcgcgg tgacggatga tgaagagaga gggagggaga    1020
ttggggagag aatggtggag gcgtttatga aggaagggaa cttgaaggct ttggctatgg    1080
tgaagaagct tgatcgagtt ggtgcccgcc ttgttagtag caattcatga                1130
```

```
<210> SEQ ID NO 110
<211> LENGTH: 376
<212> TYPE: PRT
<213> ORGANISM: solanum lycopersicum

<400> SEQUENCE: 110

Met Ala Ile Thr Phe Gln Ser Pro Met Lys Leu Ser Phe Ile Thr Ser
1               5                   10                  15

Asn Gly Phe Ser Asn Pro Pro Ser Leu Tyr Pro Ile Asn Thr His Phe
            20                  25                  30

Ser Phe Gly Phe Asn Leu Ser Ser Val Ser Ser Lys Thr Gln Thr His
        35                  40                  45

Ile Thr Ile Pro Glu Pro Glu Pro Val Phe Thr Ser Val Lys Ser Phe
    50                  55                  60

Ala Pro Ala Thr Val Ala Asn Leu Gly Pro Gly Phe Asp Phe Leu Gly
65                  70                  75                  80

Cys Ala Val Asp Gly Val Gly Asp Phe Val Thr Leu Arg Val Asp Pro
                85                  90                  95

Asn Val Lys Ala Gly Glu Val Ser Ile Ser Asp Ile Ser Gly Ala Gly
            100                 105                 110

Asn Arg Leu Ser Lys Asp Pro Leu Ser Asn Cys Ala Gly Leu Ala Ala
        115                 120                 125

Ile Ser Val Met Lys Met Leu Asn Ile Gln Ser Val Gly Leu Ser Ile
    130                 135                 140

Ser Leu Glu Lys Gly Leu Pro Leu Gly Ser Gly Leu Gly Ser Ser Ala
145                 150                 155                 160

Ala Ser Ala Ala Ala Ala Val Ala Val Asn Glu Ile Phe Gly Arg
                165                 170                 175

Lys Leu Ser Val Asp Asp Leu Val Leu Ala Gly Leu Glu Ser Glu Thr
                180                 185                 190

Lys Val Ser Gly Tyr His Ala Asp Asn Ile Ala Pro Ser Ile Met Gly
            195                 200                 205

Gly Phe Val Leu Ile Arg Ser Tyr Asp Pro Leu Glu Leu Ile Pro Leu
        210                 215                 220

Lys Phe Pro Phe Glu Lys Asp Leu Phe Phe Val Leu Val Asn Pro Glu
225                 230                 235                 240

Phe Glu Ala Pro Thr Lys Lys Met Arg Ala Val Leu Pro Ser Glu Val
                245                 250                 255

Thr Met Ser His His Ile Trp Asn Cys Ser Gln Ala Gly Ala Leu Val
                260                 265                 270

Ala Ala Ile Leu Gln Gly Asp Ser Arg Gly Leu Gly Lys Ala Leu Ser
            275                 280                 285

Ser Asp Lys Ile Val Glu Pro Arg Arg Gly Pro Leu Ile Pro Gly Met
        290                 295                 300

Glu Gly Val Lys Lys Ala Ala Leu Lys Ala Gly Ala Phe Gly Cys Thr
305                 310                 315                 320

Ile Ser Gly Ala Gly Pro Thr Leu Val Ala Val Thr Asp Asp Glu Glu
                325                 330                 335

Arg Gly Arg Glu Ile Gly Glu Arg Met Val Glu Ala Phe Met Lys Glu
            340                 345                 350

Gly Asn Leu Lys Ala Leu Ala Met Val Lys Lys Leu Asp Arg Val Gly
        355                 360                 365

Ala Arg Leu Val Ser Ser Asn Ser
    370                 375
```